(12) United States Patent
Webler et al.

(10) Patent No.: US 8,419,714 B2
(45) Date of Patent: Apr. 16, 2013

(54) FLEXIBLE LOW COMPLIANCE EXTENSION TUBING FOR BALLOON INFLATION

(75) Inventors: William E. Webler, Escondido, CA (US); August R. Yambao, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 12/705,556

(22) Filed: Feb. 12, 2010

(65) Prior Publication Data
US 2010/0191220 A1 Jul. 29, 2010

Related U.S. Application Data

(62) Division of application No. 11/313,477, filed on Dec. 20, 2005, now Pat. No. 7,674,240.

(51) Int. Cl.
*A61M 25/18* (2006.01)
*A61M 25/00* (2006.01)
*A61M 29/00* (2006.01)

(52) U.S. Cl.
USPC ......... 604/538; 604/97.02; 604/524; 604/533

(58) Field of Classification Search .... 604/96.01–97.02, 604/264, 523, 524, 533, 538
See application file for complete search history.

(56) References Cited

U.S. PATENT DOCUMENTS

| | | |
|---|---|---|
| 4,583,974 A | 4/1986 | Kokernak |
| 4,739,768 A * | 4/1988 | Engelson ............ 600/435 |
| 4,990,139 A | 2/1991 | Jang |
| 5,236,659 A | 8/1993 | Pinchuk et al. |
| 5,348,538 A | 9/1994 | Wang et al. |
| 5,389,070 A | 2/1995 | Morell |

(Continued)

FOREIGN PATENT DOCUMENTS

| | | |
|---|---|---|
| EP | 0261831 A2 | 3/1988 |
| WO | WO-2004/080508 A1 | 9/2004 |

OTHER PUBLICATIONS

Webler, et al., "PCT Search Report and Written Opinion of the International Searching Authority", mailed May 24, 2007; PCT/US2006/045205, filed Nov. 21, 2006.

(Continued)

*Primary Examiner* — Victoria P Shumate
(74) *Attorney, Agent, or Firm* — Randy Shen; Blakely, Sokoloff, Taylor & Zafman LLP

(57) ABSTRACT

A controlled volume inflation-deflation device to inflate a balloon to occlude a blood vessel by dialing a knob that locks at rotational positions to locate a plunger at equally spaced locations within a syringe of the inflation-deflation device. The inflation-deflation device includes a releasable latch to lock the proximal and distal housings together to hold the plunger forward for occlusion, and to separate and hold the proximal and distal housings to retract the plunger for perfusion. When the inflation-deflation device is returned to the latched position, the balloon is re-inflated to its previous occlusive diameter. Also, an extension tube made of a lower modulus outer material co-extruded over and miscible with a higher modulus inner material may be used to produce a suitably low compliance extension tube for the inflation-deflation device. The balloon may have tapered ends and a cylindrical center portion so that it increases by more equal increments in outer diameter in response to incremental equal increases in inflation volume.

22 Claims, 18 Drawing Sheets

U.S. PATENT DOCUMENTS

| | | | |
|---|---|---|---|
| 5,622,665 | A | 4/1997 | Wang |
| 5,634,910 | A | 6/1997 | Kanner et al. |
| 6,056,721 | A | 5/2000 | Shulze |
| 6,129,737 | A | 10/2000 | Hamilton et al. |
| 6,234,996 | B1 | 5/2001 | Bagaoisan et al. |
| 6,258,080 | B1 | 7/2001 | Samson |
| 6,277,093 | B1 | 8/2001 | Lee |
| 6,368,316 | B1 * | 4/2002 | Jansen et al. ............... 604/526 |
| 6,585,718 | B2 * | 7/2003 | Hayzelden et al. ........... 604/523 |
| 6,641,573 | B1 | 11/2003 | Parodi |
| 7,112,357 | B2 * | 9/2006 | Miller et al. ............... 428/36.92 |
| 7,169,170 | B2 * | 1/2007 | Widenhouse ................ 623/1.11 |
| 2003/0094736 | A1 | 5/2003 | Qin et al. |
| 2004/0133156 | A1 | 7/2004 | Diaz et al. |
| 2005/0015048 | A1 | 1/2005 | Chiu et al. |
| 2005/0256503 | A1 * | 11/2005 | Hall ............................. 604/523 |
| 2005/0256508 | A1 * | 11/2005 | Hall ............................. 604/529 |
| 2006/0100511 | A1 * | 5/2006 | Eriksen ......................... 600/431 |
| 2006/0149189 | A1 * | 7/2006 | Diamond et al. .............. 604/118 |
| 2007/0010787 | A1 * | 1/2007 | Hackett et al. ............. 604/96.01 |
| 2008/0114316 | A1 * | 5/2008 | Christensen et al. ......... 604/323 |
| 2010/0191220 | A1 * | 7/2010 | Webler et al. ................. 604/509 |

OTHER PUBLICATIONS

Webler, et al., "International Preliminary Report on Patentability", mailed Jun. 24, 2008, PCT/US2006/045205, filed Nov. 21, 2006.

Abbott Cardiovascular Systems, Final Office Action dated Aug. 3, 2009 for U.S. Appl. No. 11/313,477.

Abbott Cardiovascular Systems, European Examination Report dated Feb. 7, 2011 for EP 06838275.3.

* cited by examiner

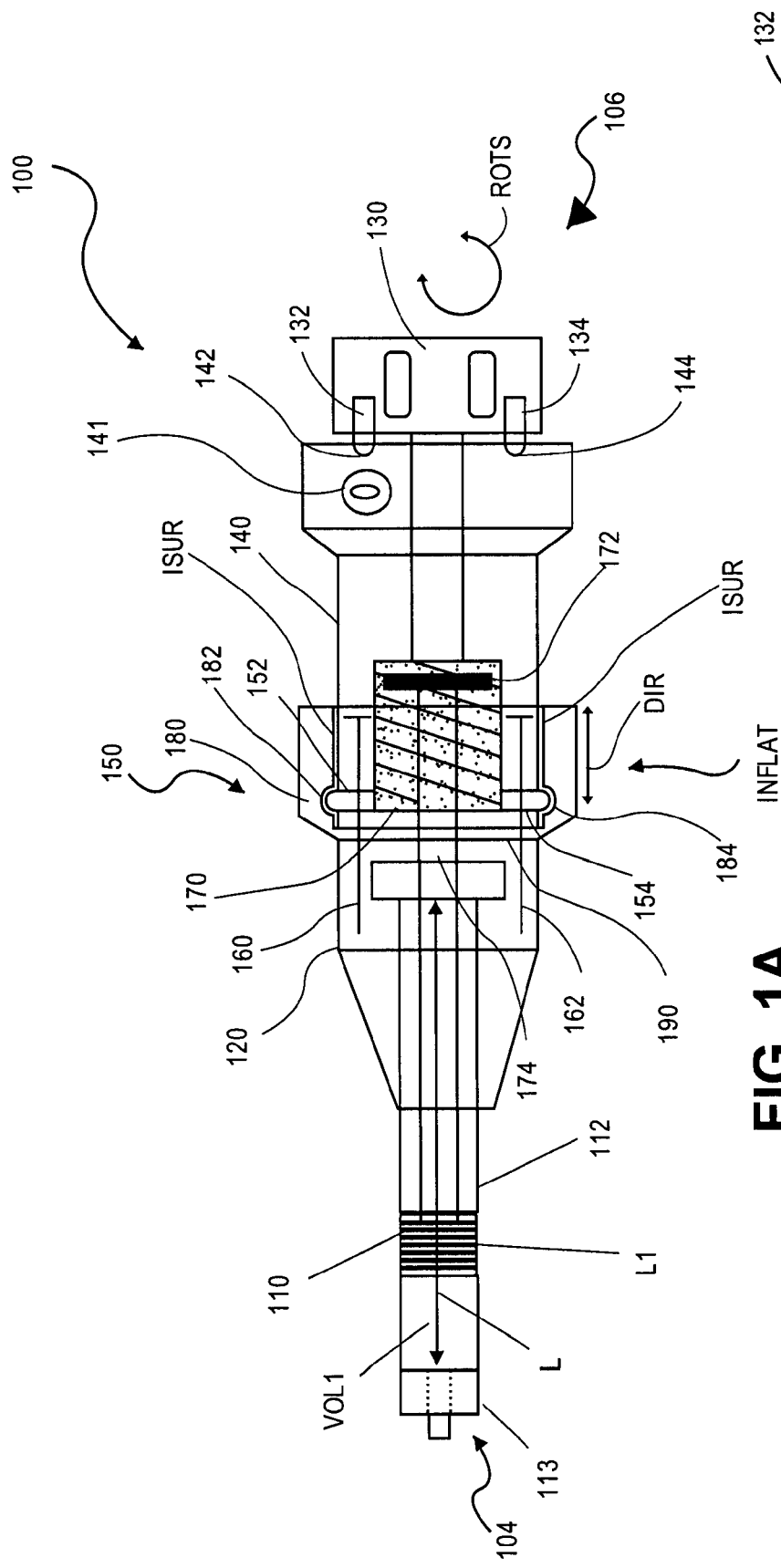
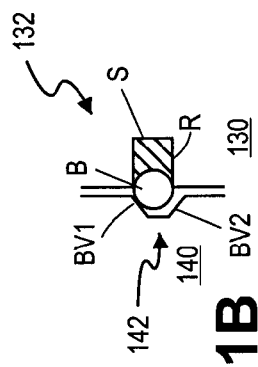
FIG. 1A
FIG. 1B

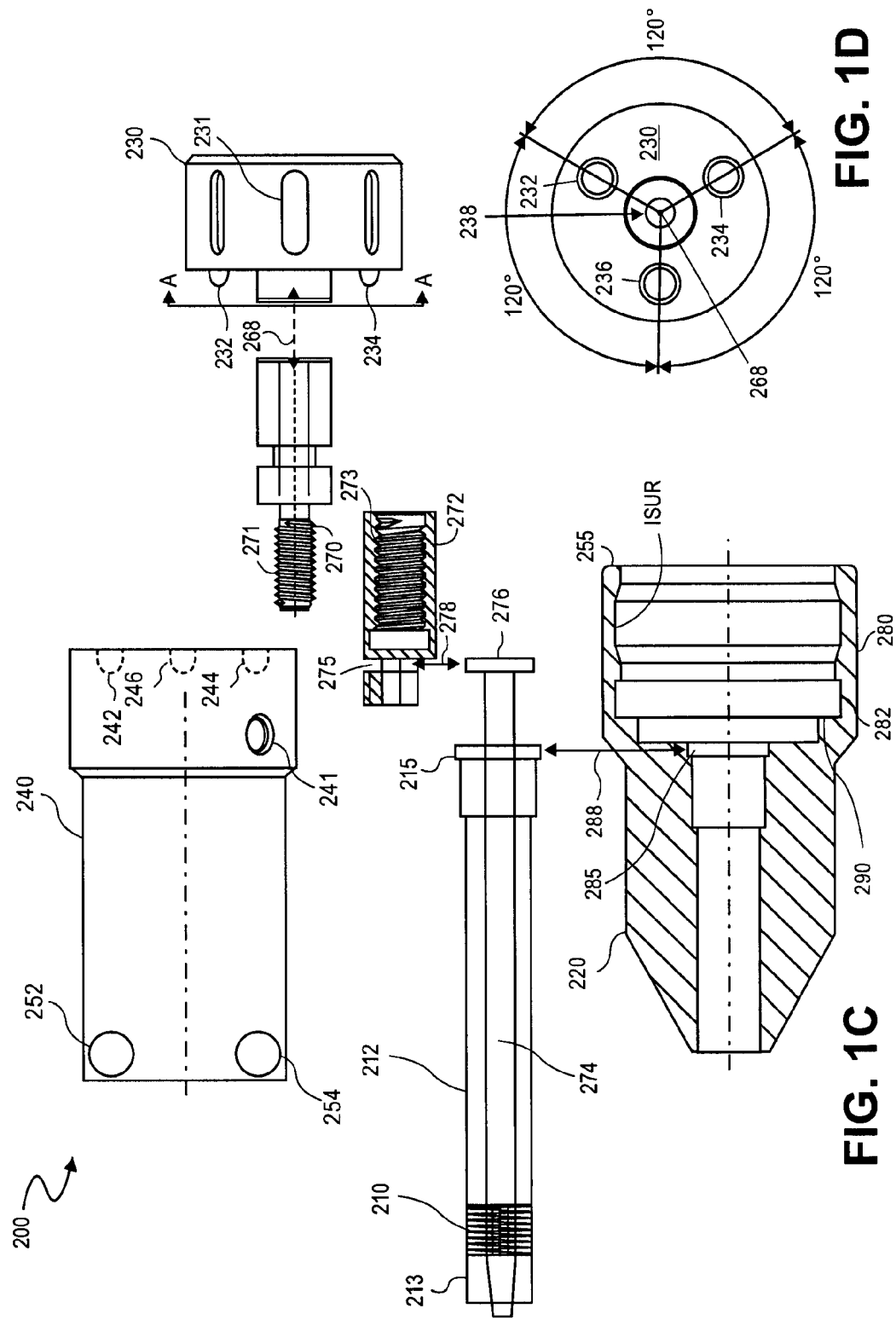

FLEXIBLE LOW COMPLIANCE EXTENSION TUBING FOR BALLOON INFLATION

This application is a divisional of U.S. application Ser. No. 11/313,477 filed on Dec. 20, 2005 now U.S. Pat. No. 7,674,240.

FIELD

Temporary blood vessel occlusion devices and methods.

BACKGROUND

It is increasingly important that a physician or surgeon delivering substances, such as an imaging or treatment agent or drug, is able to safely, efficiently and accurately occlude a blood vessel at a region of interest to visualize or treat a desired target tissue for effective delivery of the substance. Moreover, it is also important that the physician or surgeon is able to efficiently and accurately remove the occlusion of the blood vessel (allow perfusion of the target tissue) after the desired time interval to avoid damage to the desired target tissue, such as by lack of oxygen. This is particularly true when the desired concentration and/or resident time of the substance required at the target site cannot be safely and/or effectively achieved by introduction of the substance to a location remote from the target site. Moreover, the physician may only want to treat the diseased portion of an organ or tissue to avoid treating any healthy portion. In a similar manner, a physician or surgeon may use vessel occlusion to selectively deliver an imaging agent or transparent flushing fluid to the inner diameter (ID) of a vessel. For example, an imaging agent may be injected with vessel occlusion or partial occlusion to more easily/selectively visualize the vessel "roadmap", to more easily visualize/measure the tissues that may be subsequently treated, to label a map of such tissues or to observe/measure the tissues' perfusion and/or clearance/wash out characteristics. A transparent flushing fluid may be injected with vessel occlusion, for example, to improve optical coherence tomography (OCT) imaging or the light application of a photodynamic therapy.

For example, to achieve localized treatment of tissue, such as tissue in a heart, physicians and surgeons can use catheters with occlusion devices, such as balloons. Specifically, blood vessels, such as arteries and veins, can be temporarily occluded during treatment by inflating a balloon at a region of interest of the vessel to block blood flow and thus avoid or retard the washing away of the imaging or treatment agent or drug by the flowing blood. After treatment, the region of interest may then be perfused (blood allowed to flow) by deflating the balloon to unblock the vessel.

In some cases, cardiovascular guide catheters are generally percutaneous devices used to advance through a vasculature of a patient proximal to a region of interest and are devices through which another catheter or device may be inserted. Similarly, guidewires may be advanced through a guide catheter and further into the vasculature, across a vascular region of interest. Infusion or delivery catheters are generally catheters used to deliver or infuse a treatment and/or imaging agent to a region of interest in a vasculature of a patient and typically may be engaged with a guidewire and inserted through another catheter (e.g., a guide catheter) and advanced into the vasculature to the desired region of interest. Moreover, occlusion devices, such as occlusion balloons, may be attached to a guide catheter, a guidewire or an infusion catheter to occlude and then perfuse (remove the occlusion and allow blood flow through) a region of interest in a vasculature. Additionally, a guide catheter or infusion catheter may be used to deliver or infuse a treatment and/or an imaging agent to a region of interest in a vasculature of a patient proximal or distal to the occlusion device before, during or after an occlusion.

In addition, an inflation-deflation device may push fluid into and retract fluid from the interior or cavity of the occlusion device or balloon via a catheter to inflate and deflate the occlusion device or balloon (e.g., such as using a lumen or tube in the catheter to communicate a fluid between the inflation device and the inner chamber of a balloon). To help control the outer diameter of a balloon and for safety reasons, the catheter and balloon may be aspirated (remove air and replace it with a fluid) prior to inflating the balloon with fluid to occlude the blood vessel. The fluid most often used to aspirate the catheter and balloon and inflate the occlusion balloon is contrast or a mixture of contrast and saline. Contrast is an imaging agent that allows the balloon to be imaged by an imaging modality such as fluoroscopy, MRI or ultrasound. Occlusion of the vessel is generally confirmed by injecting contrast into the guide catheter and observing by fluoroscopy that none of this contrast flows past the inflated balloon and/or by observing a pressure change due to the occlusion (i.e. the pressure of the blood may be monitored via a lumen of the catheter). Balloons may be made of a variety of materials and their inflation controlled to create non-compliant, compliant and elastic balloons. A non-compliant balloon, like those commonly used on balloon dilation catheters, may be used at moderate or low pressures (compared to dilation pressures) to occlude a vessel safely over a very small range of vessel diameters. However, conventional means to determine a vessel's inner diameter (usually fluoroscopy) are not highly accurate, especially in eccentric vessels/vessels with atheroma. If the device balloon size chosen is too small, then adequate vessel occlusion may not be obtained. If the device balloon size chosen is too large, then the vessel wall may be unnecessarily damaged by over expansion in a manner that may result in a dissection and/or a subsequent vessel stenosis or restenosis. Generally, a compliant, small volume balloon may be used to allow for more rapid balloon inflations and deflations and for more adjustable balloon diameters to allow vessel occlusion over a wider range of vessel diameters at lower balloon pressures. Generally, an elastic, small volume balloon allows for far more adjustable balloon diameters to allow vessel occlusion over a much wider range of vessel diameters at even lower balloon pressures. The difference between a compliant balloon and an elastic balloon is that a compliant balloon will not return to very nearly its original uninflated size (OD) or shape after inflation to its maximum designed size (OD), whereas an elastic balloon will return to its original uninflated size (OD) and shape after inflation to its maximum designed size. Often a compliant balloon will have an initial, pre-insertion, or nominal ID that is larger than the outer diameter (OD) of the catheter/device that it is mounted on and, thus, the compliant balloon will be folded to hug the catheter/device shaft during insertion into a vessel. Often the ID of an elastic balloon will closely fit to the OD of the catheter/device that it is mounted on and not require folding. Lower inflation pressures are desired, as less pressure is then available to damage/expand the vessel wall, if the balloon is over-sized due to an accidental misadjustment, an incorrect vessel size determination or other reasons. As a limit, the inflation pressure applied to or present in an occlusion balloon may equal or exceed the blood pressure of the vessel to keep the balloon inflated and occluding that vessel. Small volume balloons are desired because of their more rapid inflation and deflation times at low pressures. A wide range of balloon diameter adjustment is desired, as fewer devices may be stocked to cover a particular vessel size range (vessel sizes vary in the anatomy and across the population) and the degree of vessel diameter determination accuracy required to choose a device that will safely occlude the vessel is reduced. In some cases, what is desired is inflation/deflation, aspiration, and occlusion balloon devices and procedures that allow for repeated occlusion and perfusion of a blood vessel with a low risk of damaging/expanding the vessel wall. For instance, there is a need for an occlusion balloon, such as an elastic small volume low pressure balloon, that will expand to predictable repeatable outer diameters in response to being inflated and deflated with predictable repeatable amounts of fluid that can be provided by an inflation/deflation device (after successful aspiration).

SUMMARY

There is disclosed an inflation-deflation device for inflating and deflating an occlusion device or a balloon using increments of selected, controlled, or equal volumes of a fluid. A preferred embodiment of such an inflation-deflation device, without limitation to any single or combinations of components or functions thereof, may be a controlled volume inflation deflation device, such as an "INDEFLATOR®" which is a trademark of Guidant Corporation, 3200 Lakeside Drive, Santa Clara, Calif. 95054-2807. Such an inflation-deflation device may also be referred to as a controlled volume INDEFLATOR®. The device of the present invention can be especially useful when used with compliant or elastic balloons. The controlled volume inflation-deflation device (e.g., controlled volume INDEFLATOR®) may have a syringe, which consists of a body and a plunger, to push in and retract out volumes of fluid communicated with the interior or cavity of the balloon via a catheter or lumen therethrough. The device may also have a releasable latch between a proximal portion, which constrains the syringe's plunger via a longitudinal incremental manipulation mechanism, and a distal portion, which constrains the body of the syringe, so that releasing the latch allows for relative motion between the proximal housing and the distal housing, such that the plunger may be moved a distance into or out of the body of the syringe. Specifically the latch may define two releasably latched positions to move the plunger a set distance within the syringe body.

When the described controlled volume inflation-deflation device is used to control the diameter of balloons that have an initial or nominal diameter or a desired initial diameter or inflation that requires an initial volume of fluid to be injected into the balloon (via a catheter, a communicating lumen and/or cavity), the balloon may be initially inflated with another device and then connected to the controlled volume inflation-deflation device. This connection transition can be accomplished in the desired manner using a stopcock. For instance, using a stopcock, a compliant balloon may be initially inflated to its initial or nominal diameter using a conventional inflation-deflation device to inflate the balloon to a low pressure, or using a low volume syringe to inflate the balloon to a given injection volume. Because the diameters of elastic balloons are difficult to control using pressure, the initial inflation of elastic balloons that hug the OD of the catheters that they are mounted on to an initial OD is preferred to be done using a given injection volume.

BRIEF DESCRIPTION OF THE DRAWINGS

Various features, aspects and advantages will become more thoroughly apparent from the following detailed description, the set of claims, and accompanying drawings in which:

FIG. 1A is a schematic partial see through side view of a controlled volume inflation-deflation device having a latch in the first (inflation) latched position.

FIG. 1B is a schematic cross-sectional side view of a portion of the controlled volume inflation-deflation device showing an indexing lock engaging a recess.

FIG. 1C is schematic side views and cross-sectional side views of various components of a controlled volume inflation-deflation device.

FIG. 1D is a view of knob 230 along perspective A of FIG. 1C.

DETAILED DESCRIPTION

Figure 1E:
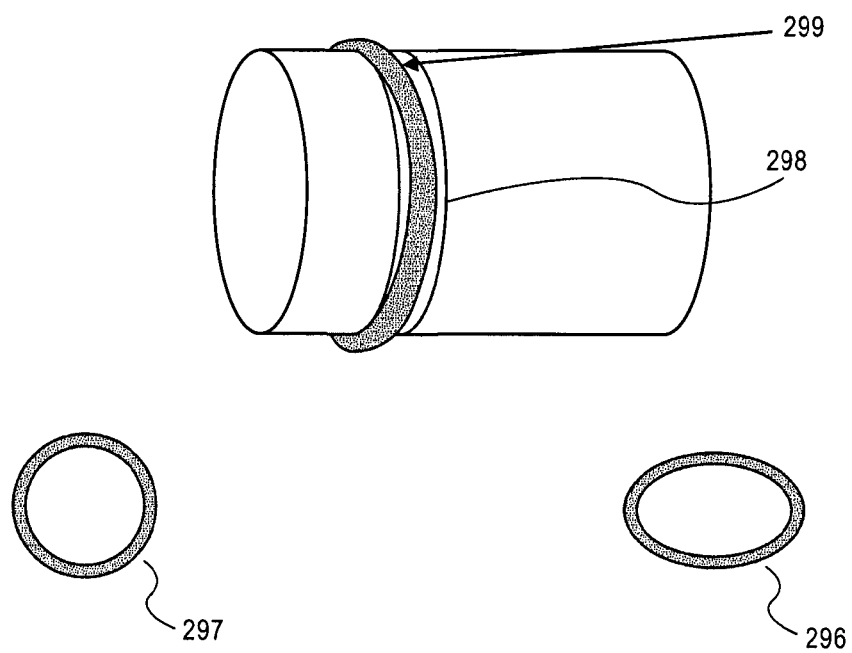
FIG. 1E shows a radial spring or o-ring in a groove.

Some embodiments are directed to a device for inflating and deflating a blood vessel occlusion device, such as an occlusion balloon, a compliant balloon, an elastic balloon, a non-compliant balloon, and/or a balloon as described below with respect to FIGS. 15-18. Such inflating and deflating devices may be described by the terms "inflation-deflation device" or such as the device known as the "Indeflator®", which is a trademark of Guidant Corporation, 3200 Lakeside Drive, Santa Clara, Calif. 95054-2807. For example, an inflation-deflation device may have a syringe, which consists of a body and a plunger, for communicating, such as by pushing and retracting volumes of fluid with the inside or internal cavity of an occlusion device, such as a balloon, via a catheter or lumen therethrough. Specifically, the syringe may include a connector at its tip to attach to a proximal end of a tube, cannula, or catheter having the balloon device attached to it. The inflation-deflation device may include a plunger or piston within a syringe tube to drive fluid within the syringe tube through the syringe tip out the connector through a tube or lumen in the cannula or catheter and into the inside, inner dimension, or cavity of the balloon to expand the outer diameter of the balloon (e.g., an "occlusion balloon") sufficiently to occlude a blood vessel at a region of interest.

The outer diameter of an occlusion balloon may be controlled by inflating and deflating the balloon with selected or controlled volumes of relatively incompressible liquids and solutions. For example, a controlled volume inflation-deflation device may inflate an occlusion balloon with increments of controlled, selected, and/or equal volumes of fluid to control the outer diameter of the balloon to predetermined or selected outer diameters that it is known the balloon will reach given the initial volume or pressure of fluid injected into the balloon and the incremental volume increases. Moreover, a controlled volume inflation-deflation device may include a latch or device having a latched position for placing the plunger at a first location at which the volume increments of fluid are forced into the balloon after insertion of the balloon on a catheter into a blood vessel to a region of interest and after the initial inflation of the balloon to an initial OD to effect an occlusion. The controlled volume inflation-deflation device latch may also have a deflation latched position to place the plunger at second location to pull a volume of fluid out of the balloon to deflate the balloon and remove the occlusion. Subsequently, the controlled volume inflation-deflation device may be transitioned between the inflation latched position and the deflation latched position to re-inflate the balloon to the adjusted OD or deflate the balloon.

The latch may be a releasable latch between a proximal portion, which constrains the syringe's plunger via a longitudinal incremental manipulation mechanism, and a distal portion, which constrains the body of the syringe, so that releasing the latch allows for relative motion between the proximal housing and the distal housing, such that the plunger may be moved a distance into or out of the body of the syringe. Specifically the latch may define two releasably latched positions to move the plunger a set distance within the syringe body. For example, the first position (e.g., an inflation position or an inflation latched position) may be used when inflating the balloon with a sufficient volume to occlude a blood vessel, while the second position (e.g., a deflation position or a deflation latched position) may be used to reduce the volume in (deflate) the balloon sufficiently to allow for perfusion of the blood vessel or the withdrawal or re-positioning of the balloon. Thus, after a proper occlusion volume of fluid inflates the balloon for occlusion, switching or transitioning between the first/inflation and second/deflation latched positions allows for transition between occlusion (balloon inflated) and perfusion (balloon deflated). Specifically, the latch may be releasably latched in the first position and the balloon may be inflated with a sufficient volume for occlusion, then when desired, the latch may be transitioned to the second position, reducing the volume of fluid in the balloon so that the blood may perfuse or flow through the vessel and/or the balloon/catheter may be repositioned. With the latch in the first position, the position of the syringe plunger may be moved in controlled increments by a longitudinal incremental manipulation mechanism that is a part of the proximal portion of the controlled volume inflation-deflation device. The longitudinal incremental manipulation mechanism allows the operator to move the syringe plunger in controlled longitudinal increments to force increments of fluid into the balloon and, thus adjust the diameter of the balloon to effect the desired safe occlusion. In some embodiments, this manipulation mechanism may also include a counter to display the number of fluid increments that have been injected into the balloon to adjust its OD. Subsequently, the device may be transitioned between the first and second latched positions to rapidly deflate (perfuse the vessel) or rapidly re-inflate (occlude the vessel) the balloon to the previously adjusted OD. The releasable latch will retain the controlled volume inflation-deflation device in either the first or the second position when the physician is not transitioning the device (e.g., when the device is not in an unlatched position, such as a position between the first and second latched positions).

For instance, in the first/inflation latched position, a device may have or define a selected or non-selected pressure or volume of fluid to inflate a balloon with less than or up to a sufficient amount of fluid so that the balloon can occlude a region of interest of a blood vessel. Alternatively, in the second/deflation latched position, a device may have or define a selected or non-selected pressure or volume of fluid, such as to produced a pressure in the balloon that is lower than the pressure applied by the environment to the OD of the balloon (e.g., the sum of blood pressure plus atmospheric pressure at the region of interest). In some cases, this pressure may remain low enough during the deflation that the balloon deflates in a reasonable time (e.g., less than twenty seconds).

In at least one embodiment, the design of the controlled volume inflation-deflation device is modified to allow it to inject fluid into the balloon until a low predetermined balloon inflation pressure is attained and thus eliminate the need for a conventional inflation-deflation device. The modified controlled volume inflation-deflation device may operate compliant balloons or elastic balloons with an ID greater than the OD of the catheter that they are mounted on without another device, a conventional inflation-deflation device, to initially inflate the balloon to a given low pressure. To accomplish this, a low compliance pressure transducer/pressure gauge that communicates with the fluid output of the syringe to monitor and display to the operator the balloon inflation pressure is included and a separate lockable control mechanism, such as a thread mechanism, is provided to move the syringe body and syringe plunger relative to each other and force fluid out of the syringe and then allow the control mechanism to be locked in position. For instance, once the catheter/balloon has been aspirated, the balloon is positioned at the region of interest for occlusion and the modified controlled volume inflation-deflation device has been filled with fluid and de-bubbled in its first (inflation) position, the modified controlled volume inflation-deflation device is connected to the balloon inflation lumen of the catheter. The separate lockable control mechanism is then unlocked and adjusted until the desired initial balloon inflation pressure is attained and then the separate lockable control mechanism is locked in position, preventing any unintended further control mechanism adjustment. The position of the syringe plunger may then be moved in controlled increments by the longitudinal incremental manipulation mechanism to adjust the OD of the balloon to attain vessel occlusion. The modified controlled volume inflation-deflation device may then be transitioned from the first (inflation) latched position to the second (deflation) latched position to deflate the balloon and allow perfusion and/or catheter/balloon repositioning. Subsequently, the device may be transitioned between the first and second latched positions to rapidly deflate (perfuse the vessel/reposition the catheter/balloon) or rapidly re-inflate (occlude/treat the vessel) the balloon to the previously adjusted OD.

In at least one embodiment, the design of the controlled volume inflation-deflation device is modified in another manner to allow it to inject a designed/controlled amount of fluid into the balloon and thus eliminate the need for a small volume syringe. The modified controlled volume inflation-deflation device may operate compliant or elastic balloons without another device, a small volume syringe or syringe-like device, to initially inflate the balloon to a given volume. To accomplish this, the releasable latch may be designed to define a mid-latched position(s) between the first latched position and the second latched position corresponding to volume(s) of fluid for inflating the balloon(s) to a nominal OD, a minimum OD, a desired OD, to a desired volume or low pressure when the controlled volume inflation-deflation device is transitioned from the mid-latched position(s) to the first latched (inflation) position. For instance, the modified controlled volume inflation-deflation device may be set to a mid-latched position prior to its attachment to the aspirated catheter (and balloon). When the balloon is at the region of interest, the modified controlled volume inflation-deflation device is connected to the catheter lumen that communicates with the balloon and then the modified controlled volume inflation-deflation device is transitioned from the mid-latched position to the first latched position to push a volume of fluid into the balloon to inflate it to its initial or nominal diameter or a low pressure. Then the longitudinal incremental manipulation mechanism is adjusted by the physician to move the syringe's plunger in controlled increments to force increments of fluid into the balloon and, thus adjust the diameter of the balloon to effect the desired safe occlusion. The occlusion may be maintained during treatment, and then the controlled volume inflation-deflation device may be transitioned to the second latched position to allow perfusion of the vessel. Since the occlusion volume was previously pushed into the balloon with the modified controlled volume inflation-deflation device in the first latched position, transitioning the controlled volume inflation-deflation device from the second latched position to the first latched position, after a desired perfusion duration, pushes the occlusion volume back into the balloon and re-occludes the blood vessel. Thus, the modified controlled volume inflation-deflation device may be transitioned between its first latched and second latched positions to occlude the blood vessel for treatment when in the first latched position, and to perfuse the blood vessel in between treatments when in the second latched position.

To accommodate various sizes and types of balloons, at least one embodiment of the controlled volume inflation-deflation device may have various mid-latch positions corresponding to the various balloons to inflate the balloons with various volumes of fluid to attain the desired initial degree of balloon inflation or balloon OD once the balloon is at the desired location in a vessel. A controlled volume inflation-deflation device that is modified to perform the initial inflation of a balloon to a desired initial OD, initial inflation volume and/or initial inflation pressure may be termed an "integrated" controlled volume inflation-deflation device.

In at least one embodiment, a stopcock may be used to attach an aspiration syringe between the controlled volume inflation-deflation device and a catheter having a balloon positioned at a region of interest in a blood vessel. The stopcock may be adjusted to prohibit flow between the controlled volume inflation-deflation device and the catheter while the aspiration syringe is used to aspirate air from the catheter and balloon (and replace it with inflation fluid). After aspiration of the catheter and balloon, the stopcock may be adjusted to prohibit flow between the aspiration syringe and the catheter, but allow flow between the controlled volume inflation-deflation device and the balloon (i.e. via a catheter lumen). The aspiration syringe may then be removed from the stopcock. Subsequently, the balloon may be inflated for occlusion and deflated for perfusion by the controlled volume inflation-deflation device as previously described.

Moreover, some embodiments include a flexible extension line connected to the controlled volume inflation-deflation device's syringe fluid output and terminating in a male Luer or, preferably, a rotating male Luer. Alternately, the extension line may incorporate other connectors and/or be a separate device that is connected to the balloon inflation/deflation system in various locations. The extension line contains a flexible tube, but, unlike conventional extension lines and the extension lines incorporated into conventional inflation-deflation devices, this tube does not appreciably change its internal volume in response to bending or to pressure changes within its ID (it has a low compliance). Thus, this extension line does not introduce volume changes or volume change variability of a magnitude that materially interferes with the control of the balloon's OD by the controlled volume inflation-deflation device. To produce these desired properties, the extension line tubing may be comprised of an inner material with a modulus greater than a modulus of an outer material that is formed around the inner material. In addition, if the inner material and outer material are miscible, then the inner and outer material may be co-extruded to form the extension line tube. Alternately, the inner material and outer material may not be miscible, but are held together by a third co-extruded material, an adhesive polymer. In addition, the inner material may form a relatively (compared to conventional extension line tubes incorporated into conventional inflation-deflation devices and conventional extension lines) small ID tube with a relatively thin wall. In addition, the outer material may form a conventional extension line tube OD that facilitates the extension line's handling, resistance to kinking and attachments to connectors or other devices.

In some embodiments, the controlled volume inflation-deflation device is intended to be used to inflate balloons of different initial OD's. In such a case, it is desirable that the incremental increase of the balloons' OD's in response to equal volume inflation increments be similar to each other or otherwise controlled. One reason that this is desirable, is to allow or select the incremental increase in a balloon's OD to be less than or equal to the maximum over-stretch, beyond that required for occlusion, that a vessel may be subjected to by the balloon. According to some embodiments, the reasoning goes like this: In some cases, a physician may inflate the balloon very close to obtaining the desired occlusion, but is not satisfied with the occlusion. The physician may then go to the next inflation increment, which incrementally increases the balloon's diameter and occludes the vessel satisfactorily. Since the maximum that the balloon OD could grow is the incremental increase in the balloon's diameter, the maximum that the vessel could be stretched beyond that necessary for the desired occlusion is just less than that OD increment. A certain amount or percent diameter change of possible vessel over-stretch is safe and will not cause a dissection and/or a significant stenosis or re-stenosis vessel reaction. This amount may be considered to set or select the maximum OD increment for each balloon. The number of OD increments required to cover the desired OD range of a balloon sets the total incremental injection volume required. One way to make the incremental increase of the balloons' OD's in response to equal volume inflation increments similar to each other or otherwise controlled relative to each other, is to adjust the length of the various balloons. For balloons with a similar initial configuration/shape, this adjustment is such that a balloon with a smaller initial OD has a longer length than a balloon with a larger initial OD.

Additionally, an occlusion device or balloon that has an initial or nominal diameter that requires an initial volume of fluid to be injected into the balloon to inflate it such that the folds of the balloon are removed and/or it assumes an initial shape or OD is disclosed having an outer diameter that increases by relatively (compared to other balloon shapes) equal increments in diameter increase in response to being inflated by equal increments in volume over a range of diameters. For example, the balloon may have a cross-sectional profile or a contour that includes tapered (conical) ends extending proximally and distally to a cannula to which they are attached and includes a center portion between the tapered ends that defines a cylindrical shape. Other more curved balloon shapes (i.e. elliptical, spherical), have a more rapid decrease in their diameter increase increment per inflation volume increment as their diameter increases. Having relatively equal or more equal increments in diameter increase in response to being inflated by equal increments in volume over a range of diameters is desirable because this also minimizes the number of required inflation increments.

For example, FIG. 1A is a schematic partial see through side view of a controlled volume inflation-deflation device having a latch in the first (inflation) latched position. FIG. 1A shows the controlled volume inflation-deflation device 100 having proximal end 106 and distal end 104. Controlled volume inflation-deflation device 100 also has knob 130 rotationally attached to proximal housing 140 which is positioned relative (e.g., attached or coupled) to distal housing 120 by releasable latch 150. Distal housing 120 is attached to syringe tube 112 having plunger 110 disposed therewithin and tip 113. FIG. 1A also shows retaining pins 160 and 162 attached to distal housing 120 and extending within proximal housing 140.

Knob 130 is shown coupled to proximal housing 140 and to screw mechanism 170. Coupled between knob 130 and screw mechanism 170 is a counter mechanism (not shown) that causes a display that is visible through counter window 141 to increment (or decrement) in response to the rotation of knob 130. It is contemplated that screw mechanism 170 may be coupled to knob 130 such that rotation of knob 130 rotates screw mechanism 170 to engage plunger holder 172. For example, screw mechanism 170 engages plunger holder 172 in a threaded fashion so that plunger holder 172 may move or translate between the distal and proximal end of screw mechanism 170 when screw mechanism 170 is rotated by knob 130. Hence, plunger holder 172 may have threads (e.g., a set of threads or a threaded surface) corresponding to those (e.g., a matching set of threads or a threaded surface to engage the threads of holder 172) of screw mechanism 170. It is considered that screw mechanism 170 or another screw mechanism mentioned herein may include various gears, shafts, threaded assemblies, devices, surface, nuts, bolts, screws, receptacles, or other devices or surfaces having a set of threads, as known in the art, other than those shown for holder 172 and mechanism 170. Specifically, a screw mechanism may include a first set of threads coupled or attached to a syringe tube, such as to couple the syringe tube to a distal housing; and/or a second set of threads (e.g., a second set of threads that match the first set of threads to engage the first set of threads) coupled or attached to a plunger, such as to couple the plunger to a proximal housing. In turn, plunger holder 172 is attached to shaft 174 which is attached to plunger 110. Thus, rotation of knob 130 in rotational directions ROTS will cause plunger holder 172 to push or pull shaft 174 which in turn will push or pull plunger 110 along length L within syringe tube 112.

Plunger 110 may form a seal with the inner wall of syringe tube 112, such as a gas, air, water, liquid, and/or fluid-resistant seal that allows plunger 110 to push, retract, or withdraw a volume of fluid within syringe tube 112 and keeps the system closed, such that air is not appreciably drawn past the seal into the VOL 1 of syringe tube 112 during balloon deflation and neither air nor fluid is appreciably pushed past the seal and out of VOL 1 during balloon inflation. For example, volume of fluid VOL1 is shown distal to plunger 110 in syringe tube 112, and thus may be pushed out of tip 113 of syringe tube 112 by plunger 110 if plunger 110 is moved further along length L towards distal end 104, such as by rotating knob 130 in the proper direction of rotational directions ROTS. In some embodiments, syringe tube 112 may be a 1 milliliter (ml) syringe and tip 113 may be a Luer lock tip.

Window 141 may be a window to display indicia such as numbers indicating the position of plunger 110 within syringe tube 112. For example, window 141 may display the number "0" when knob 130 is rotated to a minimum position so that the plunger is at the closest position to proximal end 106 of the controlled volume inflation-deflation device adjustable by knob 130. Rotation of knob 130 may increment through a number of positions between 2 and 100 positions, such as by rotating forward and backward in directions ROTS between 10, 15, 18, 20, 22, 25, or 30 positions (having a very large number of positions is not convenient for the user). For example, where knob 130 rotates through 20 positions, window 141 may show the number "20" when knob 130 is rotated to push plunger at the position closest to distal end 104 allowed by the controlled volume inflation-deflation device by rotating knob 130 (e.g., window 141 transitions between the number "0" position and the subsequent 20 positions until it reaches the number "20" position). Also considered are a wide variety of counter/inflation status indicators or mechanisms, such as electronic displays like LED or LCD displays. In addition, there may be more than one window 141 disposed over the circumference of the proximal housing 140 to allow the count to be read, regardless of the rotational orientation of the controlled volume inflation-deflation device 100. Alternatively, window 141 and any counter mechanism may be eliminated and a user may rely on counting the clicks/detents, observing a pressure change in the vessel distal to the balloon or other occlusion indicator while turning knob 130 to effect the movement of plunger 110 within syringe tube 112 to effect a desired occlusion or balloon OD.

Releasable latch 150 may include structures and mechanisms to releasably lock proximal housing 140 at different latch positions with respect to distal housing 120 in order to locate plunger 110 at different locations along length L. For example, releasable latch 150 may allow proximal housing 140 to be latched at positions closer towards distal end 104 or closer towards proximal end 106 of inflation-deflation device 100 with respect to the position or location of distal housing 120 to move, progress, advance, translate, or slide plunger 110 along length L to adjust an amount of fluid (e.g., such as volume VOL1) within syringe tube 112. As shown in FIG. 1A, latch 150 may define or be in an inflation latched (first) position INFLAT to removably lock latch 150 to locate plunger 110 at location L1 along length L. In addition, latch 150 may define a deflation latched (second) position to removably lock the latch to locate plunger 110 at a different location proximal to location L1 along lines L.

Latch 150 may be transitioned between a inflation latched position, a deflation latched position, and/or other latched positions (e.g., such as a mid-latched position described further below with respect to FIGS. 5, 6 and 8-10) by grasping distal housing 120 and proximal housing 140 (e.g., with one human hand each) and pulling the housings apart or pushing them together until latch 150 engages into a inflation latched, deflation latched, or other latched position. Latch 150 may be described as being in an unlatched position when not in an inflation latched, deflation latched, or other latched position. Thus, once in a latched position, latch 150 may be held (e.g., locked) in that position with a sufficient force to hold a volume of fluid in a balloon without snapping, popping, slipping, or otherwise becoming unlocked or unlatched from that releasably locked position without manipulation, such as by a human hand, a robotic part, a tool, or an instrument. Moreover, latch 150 may hold that latched or locked position while knob 130 is rotated to increase and decrease the volume of fluid in syringe tube 112, such as is described further below. Locating, transitioning, holding, latching, or locking a latch referred to herein (e.g., latch 150) may be described as positioning a proximal housing (e.g., housing 140) relative to a distal housing (e.g., housing 120).

Furthermore, in some embodiments, knob 130 may have indexing locks 132 and 134 to engage recesses 142 and 144 of proximal housing 140. Indexing locks 132 and 134 may be releasable locks, devices, keepers, or detents to engage or mate with recesses 142 and 144. In turn, recesses 142 and 144 may be depressions, receptacles, notches, detents, or holes in a surface of proximal housing 140 adjacent to knob 130 having a dimension suitable to restrain indexing locks 132 and 134 from snapping, slipping, popping, or otherwise transitioning out of recesses 142 and 144 when inflation-deflation device 100 is in operation, inflating an occlusion device to occlude a blood vessel, perfusing a blood vessel, or otherwise operating as described herein. Thus, rotating knob 130 in rotational directions ROTS, such as by a human hand, may cause indexing locks 132 to disengage, or transition out of recesses 142 and 144 so that knob 130 will rotate and plunger 110 can be moved along length L. But, once knob 130 is rotated to a desired orientation or rotational position and indexing locks 132 and 134 engage recesses 142 and 144, knob 130 and plunger 110 will be locked in that position until knob 130 is again rotated by the hand. For example, indexing locks 132 and 134, and recesses 142 and 144 may be oriented so that they are engaged when knob 130 is rotated to lock plunger 110 at various locations along length L that are equidistant from one another, such as to push or withdraw equal volumes of fluid from syringe tube 112 via tip 113.

For example, FIG. 1B is a schematic cross-sectional side view of a portion of the controlled volume inflation-deflation device showing an indexing lock engaging a recess. FIG. 1B shows indexing lock 132 having ball B and spring S in receptacle R within knob 130. Spring S biases ball B toward recess 142. Receptacle R accommodates the spring and retains the ball B such that ball B may only protrude a limited distance out of receptacle R. It is contemplated that recesses described herein such as recess 142 may define various shapes with respect to the surface that they are formed in and may define various cross-sectional shapes or profiles with respect to the surface they are formed in sufficient to be engaged by indexing locks as described herein. For example, a recess may define a groove extending radial around the inner surface of a cowling, such as cowling 180 instead of defining a single hole or radial position as is explained further below with respect to recess 482 of FIG. 4. It is also contemplated that the positions of an indexing lock(s) and engaging recess(es) may be reversed. For example, indexing lock 132 may be mounted in proximal housing 140 and recess 142 in knob 130.

FIG. 1B shows ball B, and recess 142 having beveled sidewalls BV1 and BV2 in proximal housing 140. Ball B is shown engaging (e.g., such as by touching and/or being restrained from moving farther in the direction of) sidewall BV1 in proximal housing 140. It can be appreciated that ball B may engage other portions of recess 142, such as by engaging beveled sidewall BV2, or another sidewall of recess 142 in proximal housing 140. Beveled sidewalls BV1 and BV2 may be the same beveled sidewall, such as where recess 142 defines a circular, oval, or other curved shape with respect to the surface of proximal housing 140. Alternatively, beveled sidewall BV1 and BV2 may be sidewalls of two or more separate sidewalls, such as where recess 142 defines a triangular, or trapezoidal shape. Alternatively, recess 142 may have a perpendicular sidewall or sidewalls. Thus, ball B may engage recess 142 with sufficient force from spring S to prohibit or preclude ball B from slipping, snapping, or popping out of the recess until knob 130 is forcibly rotated, such as by a hand of a person, at which point ball B may pop, slip, or snap out of recess 142. Additionally, ball B may engage the sidewalls or surface OD of recess 142 such that the position of ball B, and thus the position of knob 130 relative to proximal housing 140, is held with little or no position variation.

Moreover, the releasable latch can include a cowling attached to a proximal end of the distal housing and having an inner surface extending over an exterior surface of the proximal housing with at least one cowling recess in the inner surface and at least one indexing lock at the exterior surface of the proximal housing to engage the cowling recesses. It can be appreciated that the concept of indexing locks includes devices for which only one lock/recess is required for operation of the releasable latch. It may be preferred that there be 2 or more index locks of the ball or round nose spring plunger type to balance forces and reduce friction at opposite ends of a rotational or longitudinal axis of inflation-deflation device.

Also, there may be indexing locks that comprise just a spring. For instance, FIG. 1E shows radial spring or o-ring 299 in groove 298. FIG. 1E also shows undeformed radial spring cross-section 297, and deformed radial spring cross-section 298. The radial spring can be canted so the spring will be more easily deformed when subjected to radial forces and the two ends of the spring are attached to each other to form a loop in applications like that of the proximal and distal housings (in a knob application the springs could be straight, not looped). The spring loop can go in one groove of one part, usually in a stretched (extended) condition, that retains it and it engages another groove in a second part and forms the releasable latching mechanism. In other words, this one spring can act like a lot of individual ball nosed plungers. In some embodiments, even an o-ring (usually lubricated) will operate in this configuration to make a releasable latch mechanism that is useful for creating the inflation and deflation latched (and mid-latched) positions with the proximal and distal housings. In cases with a radial spring or o-ring, there is may be only one indexing lock, the radial spring or the o-ring.

According to some embodiments, the indexing locks may include ball or round nose spring plungers, and the recesses may be through holes or blind holes having one of straight sidewalls and beveled sidewalls. In some cases for the knob recesses that operate with ball or round nose spring plungers, preferred embodiment may have straight sidewalls. Embodiments contemplated also include the simplest to design and construct and that provide the easiest means to control the forces applied by the spherical ends of an indexing lock (ball or round nose spring plungers) to the knob. Also, recesses described herein may have straight sidewalls (e.g., see FIG. 1C below). It is also worth noting that in any instance described herein of an indexing lock and recess (or groove), the structure or location of the indexing lock and recess (or groove) may be reversed, where possible.

In some embodiments the indexing lock is a ball nose spring plunger, a round nose spring plunger, a radial spring, or an o-ring. Also, the cowling recess may be a hole in the cowling, a blind hole in the inner surface of the cowling, such holes with beveled and/or straight sidewalls, or a beveled and/or straight sided groove extending radially around the inner surface of the cowling with respect to a longitudinal axis of the proximal housing. For more specific descriptions of a cowling recess, see FIG. 9 below.

It can be appreciated that the structure described for FIG. 1B may also apply to indexing lock 134 and recess 144. It is also contemplated that indexing lock 132 and other indexing locks as described herein may be ball nose springs, round-nose spring plungers, ball-nose spring plungers, or other spring actuated structures providing sufficient engaging force with/to a detent, ratchet-like or recess as described herein (e.g., recess 142). The structure described above with respect to FIG. 1B may apply to various other indexing locks, detents, and recesses of controlled volume inflation-deflation devices as described herein. Moreover, it is considered that index lock 132 and other indexing locks and corresponding recesses as described herein maybe or include other releasable locking or latching mechanisms such as those magnetically, electrically, mechanically, pneumatically, hydraulically, or otherwise releasably locked or latched with sufficient force as described herein In some cases, the indexing locks and recesses of knob 130 and proximal housing 140 may be replaced with a friction lock (e.g., a spring forcing a portion of surfaces of knob 130 and housing 140 against each other) or other locking/position retaining mechanism to omit indexing knob 130 at specific rotational locations or positions, such as to remove or eliminate the incremental nature of the volume of fluid pushed or retracted by controlled volume inflation-deflation device 100.

FIG. 1A also shows cowling 180 attached to a proximal end of distal housing 120, extending over an exterior surface of the distal end of proximal housing 140 and having stop 190. Cowling 180 has recesses 182 and 184 along its inner surface, ISUR. Recesses in cowling 180 or other cowlings herein may be described as cowling recesses or cowling grooves. Proximal housing 140 is shown having indexing locks 152 and 154 to move along the inner surface of cowling 180 for engaging recesses 182 and 184. In this engagement however, the indexing locks 152 and 154 engage the proximal sides of recesses 182 and 184, such that a force is generated the forces proximal housing 140 up against stop 190. Thus, proximal housing 140 may be moved in directions DIR with respect to cowling 180 and distal housing 120 so that indexing locks 152 and 154 move along inner surface ISUR of cowling 180. When indexing lock 152 and 154 begin to engage recesses 182 and 184, a force is generated that pulls the proximal housing 140 up against stop 190, such that controlled volume inflation-deflation device 100 may be positively held in the inflation latched position INFLAT, as shown in FIG. 1A. For instance, when distal housing 120 and proximal housing 140 are pushed together, such as by each being grasped in a human hand and forced together, stop 190 may prohibit the distal end of proximal housing 140 from moving further towards the proximal portion of distal housing 120 so that locks 152 and 154 are at least partially engaged with recesses 182 and 184 and provide a sufficient force to retain proximal housing 140 pressed against stop 190. As such, stop 190 may function as a repeatable and positive inflation latched position INFLAT, such as is described further below with respect to stop 490 and FIG. 4.

According to some embodiments, a stop (e.g., stop 190) may be used in an inflation-deflation device to control/set the force (holding force) that pushes the distal and proximal housings together in the first (inflation) latched position, such that this position is constantly and reliably exactly held. By having the index lock(s) engage one side of the recess(es) or groove at a controlled location as held by an interference with a stop, the holding force generated by the force of the indexing lock(s) pushing up against the side of the recess(es) or groove can be calculated and controlled. Without this holding force being large enough, the pressure inside the syringe (e.g., generated during balloon inflation) can create a force between the plunger and syringe tube that will overcome the holding force and cause the distal and proximal housings to move apart. This movement may be undesired as it can reduce the amount of fluid injected into the balloon during the inflation operations, making balloon OD less, less certain, less controllable and/or making it possible (in an extreme case) for the device to move out of the first (inflation) latched position spontaneously. The amount of holding force, pressure inside the syringe expected during use, available shapes, sizes, and devices used for indexing locks and recesses are factors to be considered during design of the latch, first position, inflation position, and/or engagement of the indexing lock and the groove or recess to produce a holding force (or having any mechanism to produce this holding force).

Indexing locks 152 and 154 retained or removably locked and engaged within recesses 182 and 184 may define an inflation latched position. At this inflation latched position, device 100 may inflate a balloon using knob 130, as previously described. As the balloon's OD is adjusted, the pressure in the balloon will increase. The pressure will be felt in the syringe and apply a force between the syringe tube 112 and plunger 110, which will be applied to the proximal housing 140 and stop 190 in a manner which will tend to cause them to separate. However, the force applied by the engagement of the indexing locks 152 and 154 with recesses 182 and 184 exceeds the forces applied by the syringe tube 112 and plunger 110. Thus, device 100 remains positively locked in the inflation latched position INFLAT (proximal housing 140 up against stop 190) during balloon inflation to an occlusive OD.

FIG. 1C is schematic side views and cross-sectional side views of various components of a controlled volume inflation-deflation device. FIG. 1C shows various components of controlled volume inflation-deflation device 200 disassembled, where inflation-deflation device 200 and/or various components thereof may be similar to inflation-deflation device 100 and various components thereof. For example, inflation-deflation device 200 includes knob 230, proximal housing 240, screw mechanism 270, plunger holder 272, syringe tube 212, cowling 280, and distal housing 220.

Knob 230 is shown having grooves, such as groove 231 along its outer perimeter to aid in gripping during rotation, and indexing locks 232, 234 and 236 along a surface to be oriented towards proximal housing 240. In other embodiments, the knob may have other means to aid gripping, such as raised and/or textured portions. Knob 230 may be a knob similar to knob 130, and locks 232, 234 and 236 may be locks similar to locks 132 and 134 of FIG. 1A. Knob 230 may be attached to screw mechanism 270 along line 268. For example, a shaft may be disposed within a socket of knob 230 and of screw mechanism 270 where indicated by line 268. Knob 230 may engage proximal housing 240 and screw mechanism 270 may be disposed within distal housing 240. The longitudinal position of screw mechanism 270 is fixed relative to the proximal housing 240 by pins (not shown) that penetrate the proximal housing 240 and engage the groove in the screw mechanism 270, such that screw mechanism 270 may be rotated by the rotational action of knob 230. Thus, locks 232, 234 and 236 may engage recesses 242, 244 and 246 of housing 240. FIG. 1C shows recesses 242, 244, and 246 with straight sidewalls. However, as noted above for recess 142, other shapes may be used, as described above for FIG. 1A. Proximal housing 240 is also shown having window 241. Window 241 may be a window similar to window 141 of FIG. 1A. Specifically, various gears, wheels, axles, shafts, and/or other mechanical structure may exist between knob 230 and screw mechanism 270 to display indicia at window 241 as a result of rotation of knob 230 and/or movement of plunger 210, such as is described with respect to window 141 of FIG. 1A.

FIG. 1C also shows plunger holder 272 and syringe tube 212 which may be disposed within cowling 280 and distal housing 220. Syringe end 215 may be disposed or held within cavity 285 of cowling 280 or distal housing 220, such as by pushing syringe tube 212 through distal housing 220 such that end 215 rested within cavity 285, as indicated by line 288, and fixing a suitable retaining ring or cap (not shown) over it in the cavity behind cavity 285.

Plunger holder 272 includes threads 273 such as for engaging threads 271 of screw mechanism 270. Specifically, threads 271 and 273 may be both "left hand" threads or both "right hand" threads. As shown, left hand threads would be chosen to cause the clockwise rotation of the knob 230 (when viewing the knob 230 from a proximal location) to result in the distal movement of the plunger 210 and, thus an increase in the balloon's OD, as will subsequently be described. Such a clockwise motion being the rotational motion that increases a balloon's diameter is the standard configuration of inflation-deflation devices. Holder 272 is shown having a slot or cavity 275 for engaging or holding plunger end 276, such as if end 276 were placed or fixed in cavity 275 (e.g., see line 278). Holder 272 engages features (not shown) on the ID of proximal housing 240 that prevent its rotation and thus, allows knob 230 rotation and thus screw mechanism 270 rotation to result in the proximal or distal translation of plunger end 276. The engagement of holder 272 with screw mechanism 270 and proximal housing 240 may limit its translation, such that the maximum volume of fluid that may be expelled into, for instance, a balloon inflation lumen is controlled. By controlling this maximum volume, the maximum possible volume incremented OD of the occlusion balloon is controlled to within safe limits (e.g., to prevent balloon bursting) by the controlled volume inflation-deflation device 200 or 100. Plunger end 276 is attached to plunger 210 via shaft 274. Shaft 274 may correspond to shaft 174, syringe tube 212 may correspond to syringe tube 112, plunger 210 may correspond to plunger 110, and tip 213 may correspond to tip 113 of FIG. 1A.

Figure 2:
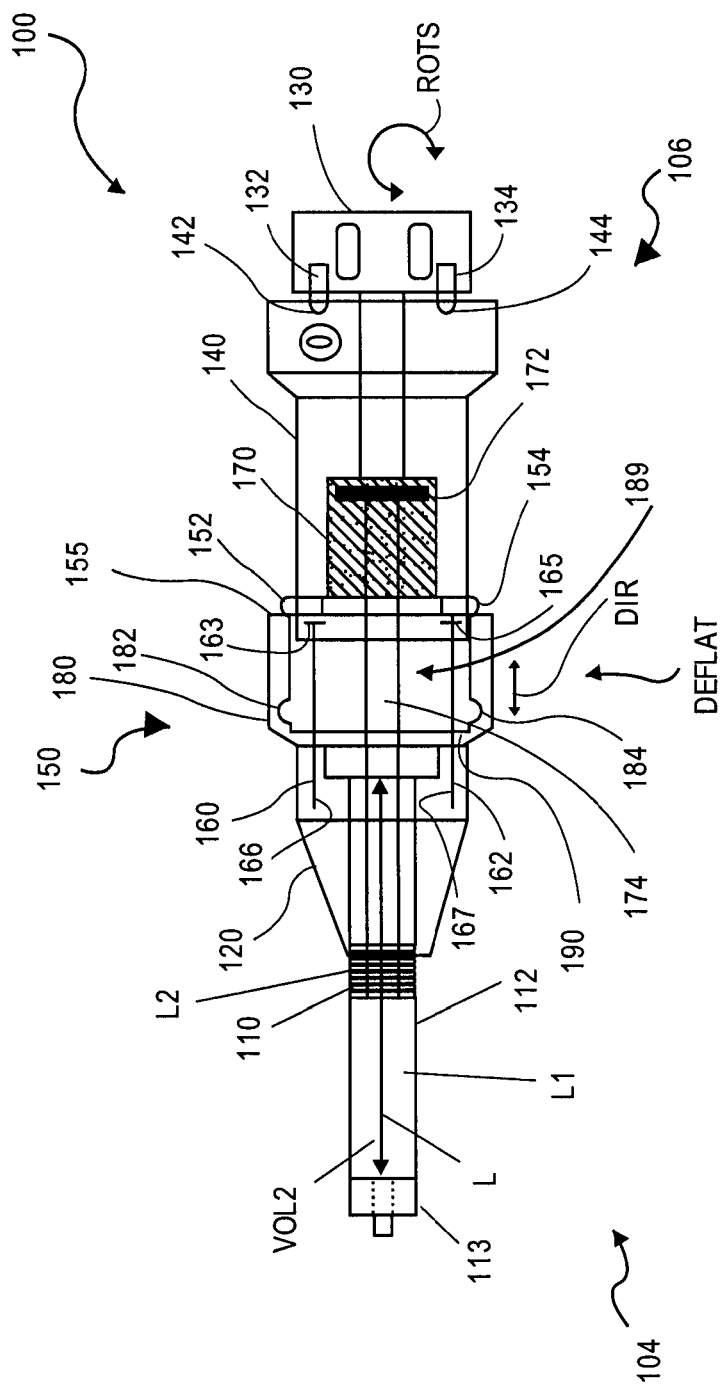
FIG. 2 is a schematic partial see through side view of the controlled volume inflation-deflation device of FIG. 1 having the latch in a second (deflation) latched position.

FIG. 1C shows cowling 280 including proximal end 255 and recess 282 along its inner surface, inner surface ISUR. Recess 282 may be a recess including recess 182 and 184 of FIG. 1A. Locks 252 and 254 of proximal housing 240 may engage an inner surface and recesses or grooves of cowling 280 similar to how locks 152 and 154 engage inner surface ISUR and recesses 182 and 184 of FIG. 1A. Not shown on proximal housing 240 is a third lock, where locks 252, 254 and the not shown lock are positioned at equal intervals around the OD of the proximal housing 240. Thus, the locks 252, 254 and the not shown lock hold the proximal housing 240 roughly centered inside the cowling 280 due to their engagement forces with the inner surface ISUR of the cowling 280. This provides for a smooth transitioning between the inflation latched and deflation latched positions. Moreover, recess 282 may be a groove extending radially around the inner surface ISUR, such as a groove having beveled sidewalls as described above with respect to BV1 of FIG. 1B. It is contemplated that recess 282 may be a groove having various other cross-sectional profiles to be engaged by indexing locks 252 and 254. As shown, recess 282 has a vertical sidewall that, when in the inflation latched position, engages the locks in a manner that creates a force that presses the distal end of proximal housing 240 into the stop 290 (surface) of the distal housing 220. Although FIG. 1C shows recess 282 with straight sidewalls, other shapes may be used, as described above for FIG. 1A. Thus, when indexing locks 252 and 254 engage recess 282, controlled volume inflation-deflation device 200 may be held or releasably latched in an inflation latched position (e.g., position INFLAT as shown in FIG. 1A), and when the indexing locks engage proximal end 255, inflation-deflation device 200 may be held or releasably latched in a deflation latched position (e.g., such as position DEFLAT of FIG. 2 shown below).

Cowling 280 also includes stop 290, such as stop 190 described above for FIG. 1A. Next, FIG. 1C shows distal housing 220 which may be a distal housing similar to distal housing 120 described above for FIG. 1A. Thus, distal housing 220 and cowling 280 may be a single component or be components attached by threaded or indexing structures such as described further below for FIGS. 7 and 9

FIG. 1D is a sectional view of knob 230 along perspective A of FIG. 1C. FIG. 1D shows knob 230 having indexing locks 232, 234, and 236. FIG. 1D also shows socket 238, such as a socket into which a shaft may be disposed to attach knob 230 to screw mechanism 270 along line 268 as shown in FIG. 1C. Specifically, proximal housing 240 may include one or more recesses for engaging locks 232 through 236. It is possible that proximal housing 240 include sufficient recesses, such that all locks engage a recess in a similar manner at each increment of rotation of the knob. This balances the forces between the knob and the proximal housing, and minimizes any bending moment that may be applied to any shaft or other mechanism that may be disposed along line 268 to facilitate the smooth operation of the knob, the smooth translation of the plunger and smooth operation any display indicia mechanism.

FIG. 1D shows indexing locks 232 through 236 in a triangular orientation 120 degrees from each other with respect to socket 238. Indexing locks 232 through 236 may each be an indexing lock similar to indexing lock 132 as described above. Although FIG. 1D shows three indexing locks, more or less than three indexing locks may be used to provide sufficient functionality to releasably latch knob 230 in equal a rotational increment positions with respect to proximal housing 240. Alternately, the indexing of knob may be accomplished by the functionality of the various gears, wheels, axles, shafts, and/or other mechanical structure (not shown) that may exist between the knob and the screw mechanism, which may also function to display indicia at the window as a result of rotation of knob.

Knob 230 is shown having a circular or cylindrical cross-sectional shape when viewed along or with respect to perspective A. It is contemplated that the other components of inflation-deflation device 200 or other inflation-deflation devices mentioned herein may include a circular or cylindrical shape similar to that shown by the view of knob 230 with respect to perspective A. Specifically, proximal housing 240, screw mechanism 270, plunger holder 272, syringe tube 212 and components thereof, cowling 280, and distal housing 220 may also have a circular or cylindrical shape with respect to perspective A. Moreover, corresponding components or features to those described above for inflation-deflation device 200, inflation-deflation device 100, or inflation-deflation device 1010, 1310, and 1410, or an inflation-deflation device including structure 400, 500, 700, 800, or 900 described below, may have a circular or cylindrical shape with respect to perspective A. Finally, it is contemplated that the knob, proximal housing, screw mechanism, plunger holder, syringe tube and components thereof, cowling, and/or distal housing of inflation-deflation devices described herein may have various other appropriate shapes with respect to perspective A, such as where one or more components have a triangular, oval, square, oblong, and/or polyhedral shape with respect to perspective A.

When index locks 152 and 154 are not in recesses 182 and 184 (see FIG. 1A) or when locks 252 and 254 are not in recess 282 (see FIG. 1C), the index locks may be releasably locked or latched to another position, such as a deflation latched position. For example, FIG. 2 is a schematic partial see through side view of the controlled volume inflation-deflation device 100 of FIG. 1A having the latch in a second (deflation) latched position. FIG. 2 shows controlled volume inflation-deflation device 100 in deflation latched position DEFLAT. In position DEFLAT, proximal housing 140 is disposed proximally or towards proximal end 106 with respect to the position of cowling 180 and distal housing 120. For example, proximal housing 140 and distal housing 120 may be grasped and pulled or forced apart by human hands.

As shown in FIG. 2, gap 189 exists under cowling 180 between the distal end of proximal housing 140 and stop 190. Since plunger holder 172 is attached to plunger 110 via shaft 174, plunger 110 is withdraw or retracted to location L2 when inflation-deflation device 100 is transitioned to position DEFLAT. Thus, when moved from position INFLAT to position DEFLAT, controlled volume inflation-deflation device 100 may withdraw or retract a volume of fluid through tip 113. Specifically, volume VOL2 of fluid in syringe tube 112 as shown in FIG. 2 is greater than volume VOL1 as shown in FIG. 1A. Moreover, the difference between volumes VOL2 and VOL1 may be selected or controlled by selecting or controlling the lengths of cowling 180 and pins 160 and 162 and the locations of recesses 182 and 184, stop 190 and stop surfaces 163 and 162 (to define position INFLAT and select/retain volume VOL1 and to define position DEFLAT and select/retain VOL2). This change in volume may be selected to be greater than the fluid volume in an inflated balloon and, thus will reliably deflate the balloon if the inflated balloon is connected to the controlled volume inflation-deflation device 100 in the position INFLAT and then the controlled volume inflation-deflation device 100 is transitioned to the position DEFLAT. For example, as shown in FIG. 2, latch 150 defines deflation latched position DEFLAT to removably lock latch 150 to locate plunger 110 at location L2 along length L, such as by indexing locks 152 and 154 being retained or removably locked proximally beyond or behind proximal end 155 of cowling 180 (to select/retain volume VOL2). Thus, indexing locks 152 and 154 may engage the back end, edge or back surface of cowling 180 at proximal end 155 with sufficient force such as not to slip, snap, or pop towards distal end 104, such as is described above with respect to index lock 132 and recess 142 with respect to FIG. 1A and FIG. 1B.

Note that retaining pins may be oriented opposite pins 160 and 162 (e.g., with the attachment and stop housings reversed). Specifically, one or more retaining pin can be attached to the proximal housing and extending through a portion of the distal housing, each retaining pin including a stop surface to engage a surface of the distal housing to limit a distance the proximal and distal housings can move apart and/or prevent rotation of the distal housing relative to the proximal housing. Moreover, in some embodiment retaining pins may be attached to the cowling and extending through a portion of the distal housing or the proximal housing to engage a stop surface of the distal housing or the proximal housing.

In addition, while or when inflation-deflation device 100 is in position DEFLAT, proximal housing 140 and distal housing 120 may be restrained or prohibited from separating too far in directions DIR. Specifically, in some cases, proximal housing 140 and distal housing 120 may be restrained or prohibited from separating too far away from each other, such as by being prohibited from separating proximally more than necessary for indexing locks 152 and 154 to move proximally beyond or behind proximal end 155. In addition, it can be appreciated that such restraint may include prohibiting separation sufficient to withdraw plunger 110 from within syringe tube 112 and to be a part of the mechanism that defines VOL2. For example, FIGS. 1A and 2 show retaining pins 160 and 162 that may be used for such restraint. As shown in FIG. 2, retaining pin 160 includes threads 166, such as for attaching retaining pin 160 to distal housing 120. Similarly, retaining pin 162 includes threads 167, which may be used for the same purpose. In addition, retaining pin 160 includes stop surface 163, such as a surface for engaging a surface or structure of proximal housing 140 to prohibit proximal housing 140 from extending too far away from distal housing 120, as described above. Similarly, retaining pin 162 includes stop surface 165, which may be for the same purpose as stop surface 163. Retaining pins 160 and 162 may be threaded rods, and/or structure as shown and described below with respect to pin 860 of FIG. 8. Additionally, retaining pins 160 and 162 engage the distal housing 120 and the proximal housing 140 in a manner that prevents them from rotating relative to each other, which is also an important function in the operation of some integrated controlled volume inflation-deflation device designs that are discussed below with respect to FIG. 9. The preventing of rotation is also a convenience to the user, as any portion of the controlled volume inflation-deflation device may be grasped while knob 130 is rotated in directions ROTS and the desired rotation of the knob 130 relative to the proximal housing 140 will be obtained. In other embodiments, it is contemplated that the functions of retaining pins 160 and 162 may be performed by a structure within cowling 180, such as being incorporated by an interference stop and/or slot mechanism between cowling 180 and proximal housing 140. In other embodiments, it is contemplated that the stop surfaces 163 and 165 engage the distal housing 102 and the threads 166 and 167 engage the proximal housing 140. In other embodiments, it is contemplated that the threads 166 and 167 be omitted and replaced with stop surfaces similar to stop surfaces 163 and 165 that engage a surface or structure of distal housing 120. In other embodiments, the retaining pins may engage the cowling and the proximal housing to provide similar functions, as previously described. In other embodiments, the plunger assembly 110, 174 and syringe body 112 may be designed engage/interference with each other to provide some or all of the functions of the retaining pins and their associated structures.

Indexing locks 152 and 154 retained or removably locked proximally beyond or behind proximal end 155 of cowling 180 may define a deflation latched position (in conjunction with the function of retaining pins 160 and 162). At this deflation latched position, a balloon may subjected to a minimal or low pressure by the increase of VOL 1 to VOL 2 and result in the withdrawal of fluid from the catheter's balloon inflation lumen and balloon to deflate the balloon.

In some embodiments, cowling 180 extends over gap 189 when latch 150 is in position INFLAT and over indexing locks 152 and 154 when in position DEFLAT. For example, cowling 180 may cover potential pinch points or openings when inflation-deflation device 100 is transitioned between deflation latched position DEFLAT and inflation latched position INFLAT (e.g., such as pinch points or openings between the proximal end of distal housing 120 and the distal end of proximal housing 140). One embodiment of this is described below in reference to FIG. 4.

Figure 4:
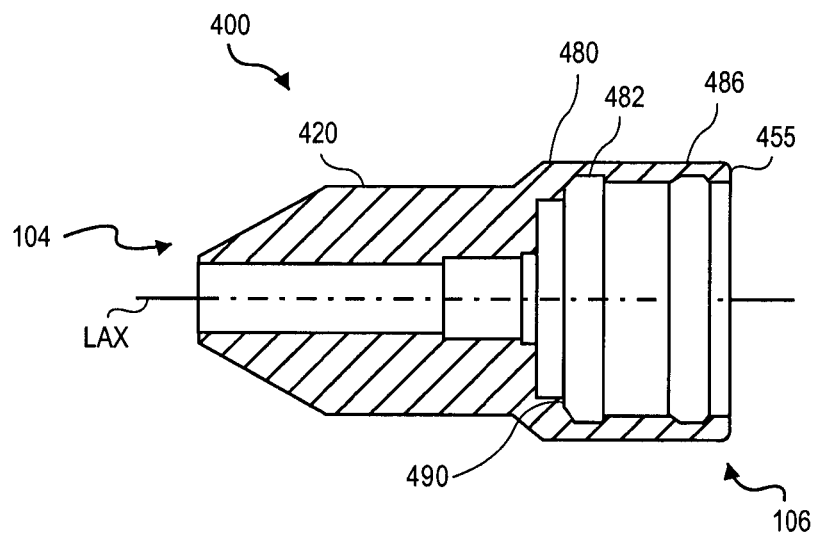
FIG. 4 is a schematic cross-sectional side view of a cowling and distal housing of a controlled volume inflation-deflation device according to one embodiment.

FIG. 4 is a schematic cross-sectional side view of a cowling and distal housing of an inflation-deflation device according to one embodiment. FIG. 4 shows structure 400 having distal end 104, stop 490, and proximal end 106. Structure 400 includes cowling 480 attached to distal housing 420 having longitudinal axis LAX. Distal housing 420 may be a distal housing as described above with respect to housing 120. Cowling 480 includes recess 482, such as a recess including recesses 182 and 184 as shown and described above with respect to FIG. 1A. In addition, cowling 480 includes recess 486, such as a recess to provide the DEFLAT position functionality described above with respect to proximal end 155 of cowling 180 of FIG. 1. Other than recess 482 and recess 486, cowling 480 may be similar to cowling 180 as described above with respect to FIGS. 1A and 2.

Figure 3:
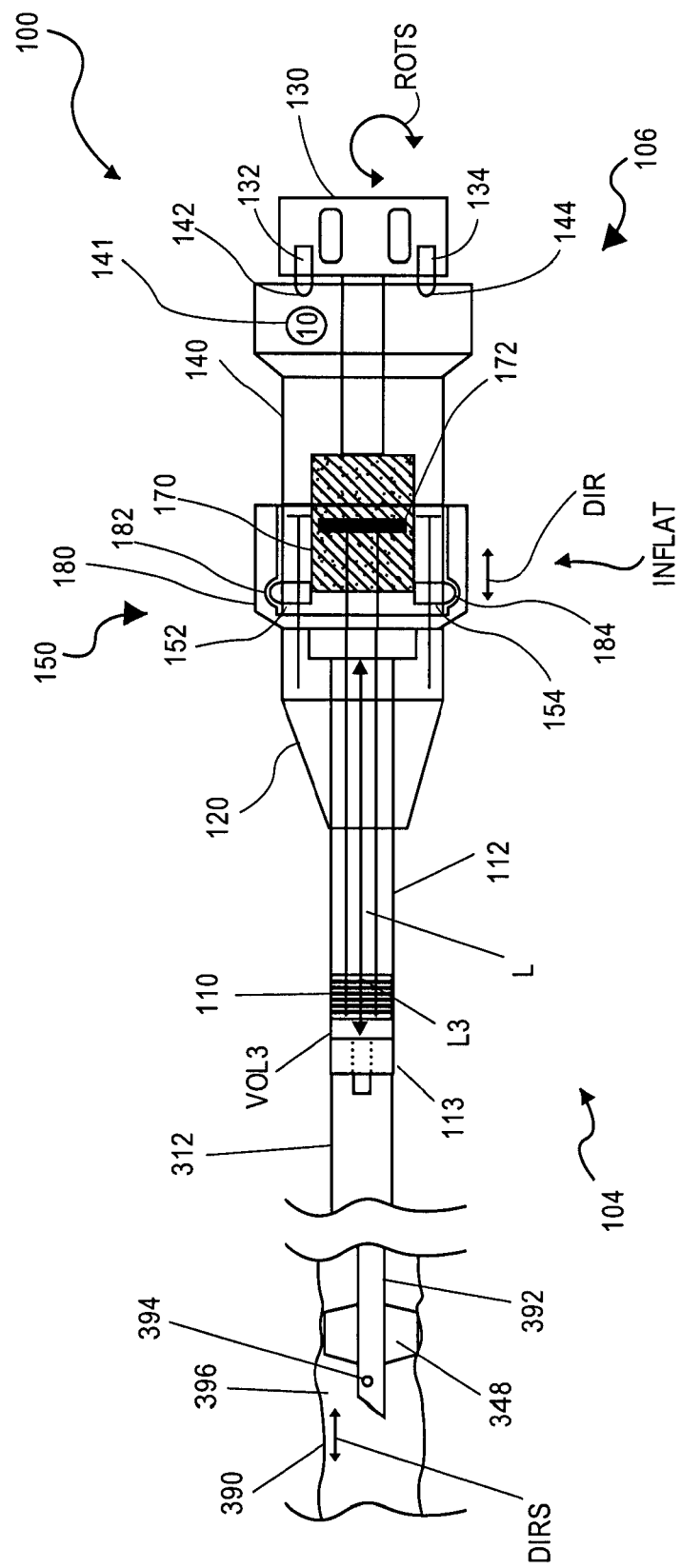
FIG. 3 is a schematic partial see through side view of the controlled volume inflation-deflation device of FIG. 1 inflating a balloon to occlude a blood vessel at a region of interest.

It is contemplated that structure 400 may be used as part of an inflation-deflation device, such as in place of distal housing 120 and cowling 180 as shown in FIGS. 1-3. Thus, structure 400 (e.g., the inner surface of cowling 480, stop 490, and recesses 482 and 486 may form a latch with proximal housing 140, locks 152 and 154, and pins 160 and 162 of FIGS. 1-3). For example, indexing locks 152 and 154 of proximal housing 140 may engage recess 482 when the controlled volume inflation-deflation device is in the inflation latched position and may engage recess 486 when the controlled volume inflation-deflation device is in the deflation latched position. These inflation and deflation latched positions may correspond to inflating or deflating a balloon described above with respect to recesses 182 and 184, and end 155 of FIGS. 1A and 2.

In addition, when the inflation-deflation device is in the inflation latched (first) position, a proximal end of distal housing 420 or portion of cowling 480 may be adjacent to, abutted against, superadjacent to, or pressed against a portion of proximal housing 140. For example, a distal end of proximal housing 140 may be abutted or pressed against stop 490 of cowling 480. Also, stop 490 may be a designed stop adjacent to recess 482 to position indexing locks 152 and 154 relative to recess 482 such that a sufficient force is generated to keep proximal housing pressed against stop 490 during balloon inflation using knob 130 or upon the transition from the DEFLAT position to the INFLAT position. Also, stop 490 may be a stop to prohibit plunger 110 from moving to an undesired position along length L, such as a position where the plunger 110 may engage the distal end of syringe body 112 before the maximum number of incremental inflation volumes may be supplied by rotating knob 130. In other words, indexing locks 152 and 154 will be prohibited from moving further distally because a distal surface of proximal housing 140 will abut against stop 490 and prohibit proximal housing 140 from moving distally with respect to distal housing 420.

Also, pins 160 and 162 may restrain structure 400 from being pulled away from proximal portion 140 such that the locks do not move distal to recess 486, and do not slip out from under the inner surface of cowling 480. Thus, pins 160 and 162 may have an appropriate length to prohibit locks 152 and 154 from being exposed or slipping out proximally to proximal end 455 of structure 400. Alternatively, in some embodiments, retaining pins 160 and 162 may have a length selected to allow locks 152 and 154 to extend proximally beyond proximal end 455, such as to define an additional releasably latched position for the inflation-deflation device.

As shown in FIG. 4, recess 482 and recess 486 may be grooves extending radially around the inner surface of cowling 480, such as grooves having beveled sidewalls such as described for beveled sidewall BV1 of FIG. 1B. It is contemplated that recess 482 may be a groove having various other cross-sectional profiles sufficient to be engaged by indexing locks as described herein. Thus, when indexing locks 152 and 154 engage recess 482, the inflation-deflation device may be held or releasably latched in position INFLAT and when the indexing locks engage recess 486, the inflation-deflation device may be held or releasably latched in (second) position DEFLAT, as described above with respect to FIGS. 1A and 2.

Thus, releasable latch 150 may be described as including cowling 180, recesses 182 and 184, inner surface ISUR, stop 190, indexing locks 152 and 154, and retaining pins 160 and 162. As such, latch 150 may be moved between an inflation latched and deflation latched position so that plunger 110 of inflation-deflation device 100 may be moved from a position where controlled volume inflation-deflation device 100 inflates an occlusion balloon sufficiently to occlude a blood vessel, to a position where inflation-deflation device 100 retracts a volume of fluid from the occlusion balloon to allow blood to perfuse around the occlusion balloon and into the blood vessel. Since latch 150 can be repeatedly releasably locked or latched to the inflation latched and deflation latched positions, it can be appreciated that the occlusion balloon can be repeatedly inflated to occlude the blood vessel and deflated to perfuse fluid to the blood vessel. For example, latch 150 can be used during treatment of a blood vessel without a substantial risk of over-inflating the occluding balloon, because the same inflation or occlusion volume VOL 1 will be provided each time latch 150 is locked in the inflation latched position INFLAT, and the same deflated or perfusing volume VOL 2 will be provided each time latch 150 is locked in the deflation latched position DEFLAT.

When in position INFLAT, volumes of fluid may be pushed by plunger 110 to inflate an occlusion balloon, such as incremental equal volumes as described above, such as to push an inflation or occlusion volume into a balloon to occlude a blood vessel. For example, FIG. 3 is a schematic partial see through side view of the inflation-deflation device of FIG. 1A inflating a balloon to occlude a blood vessel at a region of interest. FIG. 3 shows inflation-deflation device 100 in inflation latched position INFLAT, and having plunger holder 172 moved towards distal end 104 to push plunger 110 to location L3 along length L. As noted above, plunger holder 172 has threads corresponding to those of screw mechanism 170 and thus may be moved towards distal end 104 by rotating knob 130 in one direction of rotational directions ROTS. Similarly, it can be appreciated that by rotating knob 130 in the opposite direction of that used to move plunger holder 172 towards distal end 104 may be used to move plunger holder 172 towards proximal end 106, such as to retract plunger 110 towards proximal end 106. Moreover, as described above, knob 130 may be rotated so that incremental equal volumes of fluid are pushed out or withdrawn from tip 113. For instance, recesses similar to recesses 142 and 144 may be spaced along the surface of proximal housing 140 to be engaged by indexing locks 132 and 134 so that when knob 130 is rotated, the recesses are engaged by the indexing locks when plunger 110 is moved to a location along length L to push or retract equal volumes of fluid from tip 113. During rotation, window 141 may display indicia as described above. In addition, window 141 may display indicia, such as a number or symbol, indicating an increment count, expelled incremental volume or a volume within syringe tube 112 in front of plunger 110 associated with the current rotational position of knob 130 and/or plunger holder 172 with respect to proximal housing 140. For example, in FIG. 3, the numeral "10" is displayed in window 141 and may indicate that ten (10) incremental volumes of fluid have been expelled to inflate balloon 348.

It can be appreciated that knob 130 may be rotated to positions at which indexing locks in knob 130 (e.g., locks similar to locks 132 and 134) engage recesses of proximal housing 140 (e.g., recesses such as recesses 142 and 144) to communicate (e.g., by pushing out or retracting into syringe tube 112) incremental volumes of fluid through tip 113. Specifically, when rotating knob 130, one or more indexing locks of knob 130 may engage one or more recesses of proximal housing 140 to move plunger 110 to locations or positions along length L that are equally spaced, such as to change volume VOL3 in syringe tube 112 by incremental equal volumes of fluid. Moreover, it is contemplated that knob 130 may be rotated to move plunger 110 along length L, as described above, when inflation-deflation device 100 is in position INFLAT, position DEFLAT, or a mid-latched position as described below.

In addition, FIG. 3 shows inflation-deflation device 100 attached to cannula 312, such as a catheter, stopcock, or extension tube that may in turn be attached to cannula 392 having balloon 348 attached at or adjacent a distal end thereof. Balloon 348 is shown occluding blood vessel 390 near region of interest 396. Specifically, balloon 348 is inflated with a sufficient volume or pressure of fluid to prohibit blood from flowing in directions DIRS, such as to prohibit blood from flowing by balloon 348. Moreover, cannula 392 is shown with infusion opening 394, such as an opening or lumen through which a treatment agent may be infused into blood vessel 390. Cannula 392 may be an infusion catheter for infusing a treatment agent into blood vessel 390 and/or inflating balloon 348, such as to occlude blood vessel 390 or for other purposes, such as introducing an imaging agent or a flush for enhancing the energy transfer of a photodynamic therapy light and the like into the vessel. In some embodiments, opening 394 may be positioned proximal of the balloon. In some embodiments, cannula 392 may contain multiple infusion lumens and multiple openings 394. In some embodiments, cannula 392 may contain other elements such as imaging devices, sensors, fiber optic cables and the like.

In some embodiments, after balloon 348 and cannula 392 are advanced to region of interest 396 of blood vessel 390 with inflation-deflation device 100 locked into inflation latched position INFLAT, knob 130 is rotated to advance plunger 110 towards distal end 104 until a sufficient volume of fluid inflates balloon 348 to occlude blood vessel 390. After blood vessel 390 is occluded, a treatment or other agent may be infused via infusion opening 394 to region of interest 396. Alternatively, it should be appreciated that the treatment or other agent may be infused proximal to balloon 348.

Next, according to embodiments, before or after infusing a treatment or other agent, inflation-deflation device 100 may be transitioned to deflation latched position DEFLAT to withdraw a sufficient volume of fluid from balloon 348 to allow perfusion of blood vessel 390. For example, when inflation-deflation device 100 is transitioned position DEFLAT (as shown in FIG. 2) causing balloon 348 to deflate such that blood in blood vessel 390 may perfuse in directions DIRS to go by or past balloon 348. Note that the difference between volume VOL2 and VOL3 may be selected by selecting the appropriate lengths of cowling 180 and/or retaining pins 160 and 162 in directions DIR and/or selecting a location of recesses 182 and 184 and stop 190 along the inner surface of cowling 180. For instance, recesses 182 and 184 and the position of stop 190 and the length of cowling 180 and/or retaining pins 160 and 162 may be chosen to space proximal end 155 a distance away from recesses 182 and 184 and stop 190 to move plunger 110 a desired distance along length L to create the difference in volumes between volumes VOL3 and VOL2 as selected.

Thus, latch 150 and structures thereof may lock latch 150 at position INFLAT and position DEFLAT (and mid-latched positions as described further below for FIGS. 5, 6 and 10) with sufficient force that latch 150 stays locked or latched in those positions until distal housing 120 and proximal housing 140 are physically forced or pushed closer together or pulled farther apart, such as by human hands to transition the device 100 from one position to another position. Specifically, similarly to the description above with respect to FIG. 1B, indexing locks 152 and 154 may engage recesses 182 and 184, and may engage proximal end 155, with sufficient force to hold latch 150 in position when plunger 110 is holding a pressure or volume of fluid in balloon 348 sufficient to occlude or perfuse blood vessel 390. In addition, as described above with respect to manipulating knob 130 with a hand, distal housing 120 and proximal housing 140 may be pushed together or pulled apart by human hands to transition latch 150 between position INFLAT, position DEFLAT, and mid-latched positions as described below.

Although specific structures are described above with respect to FIGS. 1A-C, 2, and 3, variations are contemplated. For example, where dual structures are described, such as indexing locks, recesses, and retaining pins, a single device or set of devices may be used when sufficient. In addition, more than two devices may be used. Also, although indexing locks 132 and 134 are described on knob 130 and recesses 142 and 144 are described on proximal housing 140, the position of those structures may be reversed. For example, indexing locks 132 and 134 may be located on or in proximal housing 140 while recesses 142 and 144 are located in knob 130. Similar feature position reversals are contemplation for indexing locks 152 and 154 and recesses 182 and 184. Similarly, it is considered that cowling 180 may be attached to proximal housing 140 and indexing locks 152 and 153 may be part of distal housing 120. Moreover, retaining pins 160 and 162 may be attached to proximal housing 140 and have stop surfaces for engaging a surface of distal housing 120.

Also, it is considered that components or structures of inflation-deflation device 100 may be formed of various materials, such as metal, plastic, polymer, glass, paper, and the like. Likewise, the materials may be formed by various processes including machining, molding, injection molding, casting, forging, extruding, co-extruding, and the like.

Figure 14:
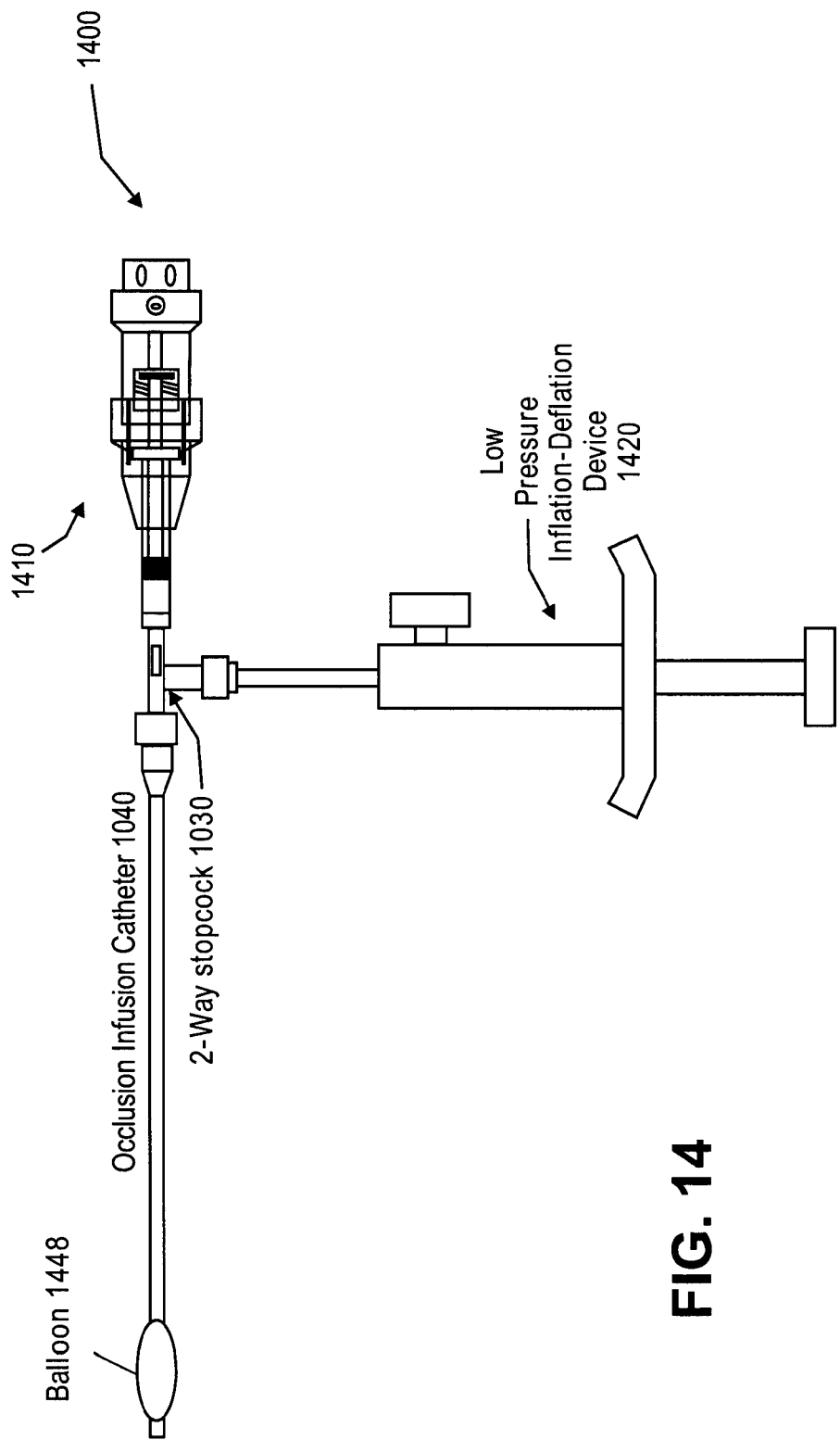
FIG. 14 is a schematic side view of one embodiment of an inflation system including a partial see through side view of a controlled volume inflation-deflation device attached to a to a stopcock that is attached to a catheter having a balloon at its distal end and attached to a conventional low pressure inflation-deflation device that performs the initial inflation of a balloon using a pre-determined inflation pressure.

According to some embodiments, the described controlled volume inflation-deflation device 100 and 200 may be used as part of an inflation system to inflate an occlusion balloon to an initial OD with another device, then use the controlled volume inflation-deflation device to increment the balloon OD to obtain the initial occlusion, as well as to inflate and deflate an occlusion balloon. Such an inflation system may be desirable, as the amount of fluid required to initially inflate a balloon to its nominal or beginning OD may require an inconveniently large number of volume increments (counter increments or amount of knob turning), especially of volume increments small enough to increment the balloon OD in small enough increments to avoid over-expanding the vessel to obtain an occlusion. Controlled volume inflation-deflation devices that do not provide for the convenient initial inflation of a balloon to its nominal of beginning OD are referred to as non-integrated controlled volume inflation-deflation devices. For example, FIG. 14 is a schematic side view of one embodiment of an inflation system including a partial see through side view of a controlled volume inflation-deflation device attached to a to a stopcock that is attached to a catheter having a balloon at its distal end and attached to a conventional low pressure inflation-deflation device that performs the initial inflation of a balloon using a pre-determined inflation pressure. FIG. 14 shows system 1400 to inflate an occlusion balloon to an initial OD using a conventional low pressure inflation-deflation device or syringe 1420, then use the controlled volume inflation-deflation device 1410 to increment the balloon OD to obtain the initial occlusion, as well as to inflate and deflate an occlusion balloon. FIG. 14 shows non-integrated controlled volume inflation-deflation device 1410, similar to controlled volume inflation-deflation devices 100 and 200, attached to 2-WAY stopcock 1030 that is attached to occlusion infusion catheter 1040 having an occlusion balloon at its distal end, and attached to a conventional low pressure inflation-deflation device 1420 or low volume syringe device 1420. A conventional low pressure inflation-deflation device 1420 may be used to inject fluid at a sufficient pressure into the catheter and balloon (e.g., a low pressure between 1 and 0.5 ATM) to obtain the initial inflation the balloon to its formed, beginning or initial OD (preferably an OD that is at or below the balloon OD required to occlude the vessel). The formed OD of a balloon is often referred to as the nominal OD of the balloon. A conventional low pressure inflation-deflation device 1420 may be used for the initial inflation of non-compliant, compliant and elastic balloons that have a formed ID that is larger that the OD of the catheter shaft that the balloon is mounted on. Usually such a balloon is folded onto the catheter shaft in the deflated condition when removed from its packaging. Inflating to a low pressure assures that the balloon will not over-expand the vessel, if the formed OD of the balloon appreciably exceeds the ID of the vessel. Alternatively, a low volume syringe device 1420 may be used to initially inject a pre-determined volume of fluid into the balloon to inflate it to its formed or beginning OD. If the balloon is an elastic balloon with a formed ID very close to the OD of the catheter shaft that it is mounted on and the desired beginning OD of the elastic balloon is significantly larger than its formed OD, then it is preferred that the balloon be initially inflated with a pre-determined volume of fluid using a low volume syringe device 1420. This is because OD's of elastic balloons above their formed OD are very difficult to control by controlling the pressure of the fluid injected into the balloon.

Device 1410 in FIG. 14 may be described as a non-integrated inflation-deflation device, since device 1410 requires assistance from another inflation device (e.g., device 1420) to conveniently initially inflate an occlusion balloon to a nominal or beginning OD from a minimal OD (the initial balloon inflation function is not integrated into the controlled volume inflation-deflation device). However, once the balloon is inflated to the nominal or beginning OD, device 1410 is able to inflate the balloon to an OD sufficient to occlude a blood vessel, and to deflate the balloon to a sufficient OD to allow the balloon to be advanced or withdrawn within a blood vessel, or to allow perfusion of a blood vessel. Also, according to some embodiments, inflation-deflation device 1410 may be a controlled volume inflation-deflation device such as inflation-deflation device 100, 200 or an inflation-deflation device having structure 400 as described herein.

Device 1420 may be a conventional low pressure inflation-deflation device, preferably including a pressure gauge capable of reading pressures of 1 ATM or less to facilitate an initial occlusion balloon inflation to a low pressure. Alternately, device 1420 may be a low volume syringe, preferably 1 cc or less with sufficient graduation marks to facilitate an initial occlusion balloon inflation with a controlled volume of fluid.

According to some embodiments, device 1410, stopcock 1030, and/or device 1420 are attached to catheter 1040 after the catheter is aspirated and in position in the vessel and is used to initially inflate the balloon to a pre-determined low pressure or pre-determined volume(using device 1420) and then adjust the balloon OD in increments until occlusion using the knob of device 1410 and then deflating the balloon by moving the latch of device 1410 to its (most proximal) deflation position and then inflating/deflating the balloon to control the occlusion at will. Once the initial inflation is accomplished, the stopcock may be turned and device 1420 disconnected. The aspiration of the balloon may be performed with catheter 1040 in the vessel or outside the body, and is preferred to be performed prior to attaching device 1410, stopcock 1030, and/or device 1420 to catheter 1040, such as using a syringe.

Furthermore, an example process for using system 1400, or a like system, is described by the following operations:

1. Aspirate air from the occlusion balloon and balloon inflation lumen of catheter 1040 using an aspiration syringe (e.g., a 20 cc syringe). Aspiration is a process by which air is removed from the occlusion balloon and balloon inflation lumen and replaced by a fluid. The compressibility of air interferes with the control of the balloon OD.
2. Assemble and de-bubble stopcock 1030, device 1420, and device 1410 (in the first latched or inflation latched position) using a wet connection process. A wet connection process is when the fluid connectors of devices are wetted/filled with fluid prior to being mated. This helps the mated connection to be air and fluid tight and avoids introducing air into the connection during mating.
3. Position the occlusion balloon at the desired occlusion position in the vessel.
4. Attach that inflation assembly from operation 2 to the balloon inflation lumen of catheter 1040 using a wet connection. At this point, the wet connection may force some fluid into the catheter 1040, causing the balloon to partially inflate. If the balloon must be re-positioned or the user will not immediately perform operation 5, then the syringe of device 1420 may be retracted slightly to ensure the complete deflation of the balloon.
5. Using device 1420, inflate the balloon to its initial inflation pressure (e.g., to an initial or formed OD, such as by inflating with a pressure of 0.5 ATM) or to its initial inflation volume, then remove device 1420 from the balloon inflation fluid path by turning stopcock 1030 and disconnect and remove device 1420 from stopcock 1030.
6. Determine if blood vessel that balloon is in is occluded as desired.
7. If vessel is not occluded at the initial balloon OD, turn knob of device 1410 to largest safe OD, as indicated by a previous fluoroscopic or other image of the vessel and a chart of the expected balloon OD to knob increment count.
8. Determine if blood vessel that balloon is in is occluded as desired. The occlusion may be tested, such as by contrast injections (e.g., via a guide catheter) or pressure readings (e.g., via a catheter 1040 lumen, a catheter 1040 infusion lumen).
9. If vessel is not occluded, increment balloon OD by turning knob of device 1410 another increment.
10. Repeat steps 8-9 as necessary to provide the initial occlusion.
11. Transition the controlled volume inflation-deflation device 1410 to the deflation (second) latched position to deflate the balloon and allow blood flow in the vessel.
12. Perform the medical treatment or procedure, occluding the vessel by transitioning the controlled volume inflation-deflation device 1410 to the inflation (first) latched position and removing the occlusion by transitioning controlled volume inflation-deflation device 1410 to the deflation (second) latched position as required.
13. When the medical treatment or procedure is complete, ensure the controlled volume inflation-deflation device 1410 is in the deflation (second) latched position (balloon deflated), remove the controlled volume inflation-deflation device 1410 from the catheter, and then remove the catheter 1040 from the vessel.

It is contemplated that operations in addition to those above may be performed when using system 1400 or a like system. Also, in some cases, fewer than all of the operations above may be performed when using system 1400 or a like system. Likewise, in some cases, the order of some of the operations above may be switched around when using system 1400 or a like system. Moreover, according to some embodiments, the operations above may include those described with respect to the processes of FIG. 11.

To create an integrated controlled volume inflation-deflation device that conveniently performs an initial inflation of the balloon with a predetermined volume of fluid, the design of controlled volume inflation-deflation device 100 may be modified. Referring back to FIGS. 1A and 2, latch 150 may define at least one mid-latch position(s) between inflation latched and deflation latched positions. For instance, according to some embodiments, indexing locks 152 and 154 may engage various other recesses along the inner surface ISUR of cowling 180 to define another latched position, and/or various mid-latched positions between the inflation latched and deflation latched positions, such as will be described further below.

Figure 5:
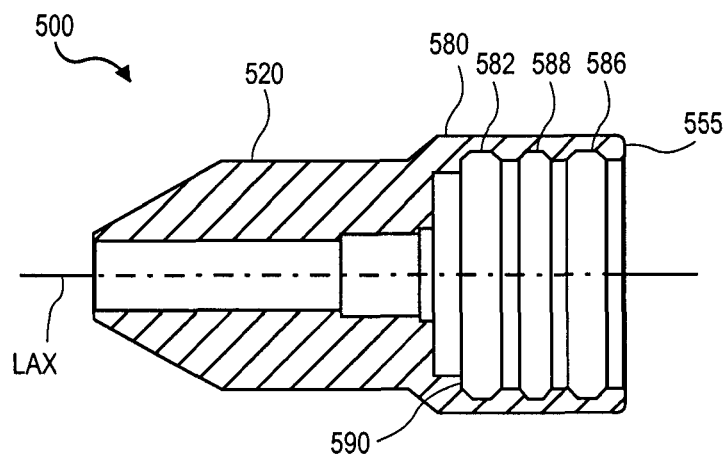
FIG. 5 is a schematic cross-sectional side view of a cowling and distal housing of an integrated controlled volume inflation-deflation device that performs the initial inflation of a balloon using a pre-determined inflation volume according to an embodiment.

FIG. 5 is a schematic cross-sectional side view of a cowling and distal housing of an integrated controlled volume inflation-deflation device according to an embodiment. FIG. 5 shows structure 500 having cowling 580 attached to distal housing 520 having longitudinal axis LAX. Cowling 580 includes recess 582, 588, and 586. Distal housing 520 may be a distal housing as described above with respect to housing 420. Recess 582 may be a recess as described above with respect to recess 482. Similarly, recess 586 may be a recess as described above with respect to recess 486. Moreover, other than recess 588, cowling 580 may be a cowling as described above with respect to cowling 480. Also, FIG. 5 shows cowling 580 including recess 588, such as a mid-recess or mid-beveled groove extending along the inner surface of cowling 588 radially between recess 582 and recess 586.

Similar to the description above with respect to structure 400 of FIG. 4, structure 500 may be used as part of an integrated controlled volume inflation-deflation device, such as to replace distal housing 120 and cowling 180 as shown in FIGS. 1A, 2 and 3 to form an integrated controlled volume inflation-deflation device. Specifically, a latch may be formed including recesses 582, 588, and 586 being engaged by locks 152 and 154 to be held or releasably latched. More particularly, FIG. 5 shows structure 500 including proximal end 555 which may function similarly to proximal end 455 as described above with respect to FIG. 4, and stop 590 which may function similarly to stop 190 of FIG. 1A and/or stop 490 of FIG. 4. Thus, when recess 588 is engaged by indexing locks 152 and 153, latch 150 or the inflation-deflation device may define a mid-latched position to removably position plunger 110 at a position between location L1 and location L2. Locks 152 and 154 engaging recess 586 may correspond to the balloon deflation position DEFLAT as described above with respect to end 155 of FIG. 2. Likewise, locks 152 and 154 engaging recess 582 may correspond to balloon inflation position INFLAT as described above with respect to recesses 182 and 184 of FIG. 1A. However, if the integrated controlled volume inflation-deflation device is attached to the balloon inflation lumen while in the mid-position (locks 152 and 154 engage recess 588) and then the latch mechanism is moved to the INFLAT position, the plunger 110 will be moved a predetermined distance inside syringe tube 112 to force a predetermined volume of fluid into the balloon to initially inflate the balloon to a pre-determined OD.

Figure 6:
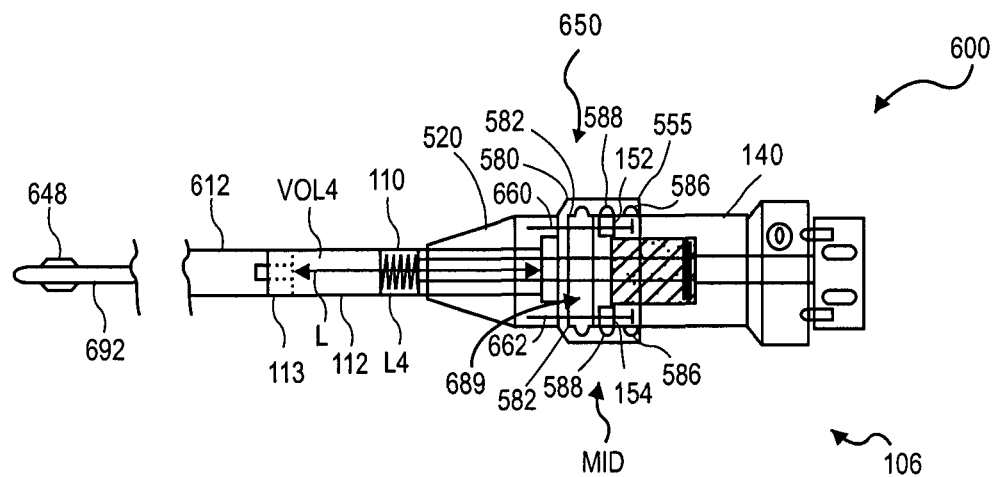
FIG. 6 is a schematic partial see through side view of an integrated controlled volume inflation-deflation device having a latch in a mid-latched position that performs the initial inflation of a balloon using a pre-determined inflation volume.

For example, FIG. 6 is a schematic partial see through side view of an integrated controlled volume inflation-deflation device having a latch in a mid-latched position. FIG. 6 shows inflation-deflation device 600 having structure 500 (FIG. 5) where recess 588 is engaged with indexing locks 152 and 154. Thus, FIG. 6 includes gap 689 between distal housing 520 and proximal housing 140 or stop 190 where gap 689 is shorter in length than gap 189 of FIG. 2. Correspondingly, plunger 110 is at location L4 along length L within syringe tube 112. Thus, syringe tube 112 may hold volume VOL4 of fluid which is greater than volume VOL1, but less than volume VOL2 (e.g., location L4 is proximal to location L1 as shown in FIG. 1A).

For example, mid-latched position MID as shown in FIG. 6 may be used to removably lock latch 650 in a mid-latched position after the syringe tube 110 has been filled with contrast or other fluid and de-bubbled, creating a filled VOL 4. Transitioning the latch 650 to the INFLAT position will inflate balloon 648, attached at or adjacent to a distal end of cannula 692 which is coupled to tube 612 attached to tip 113 of controlled volume inflation-deflation device 600, with a pre-determined volume of fluid, such as after balloon 648 and cannula 692 are aspirated and percutaneously advanced through a blood vessel to a region of interest. A pre-determined volume may be a volume of fluid to inflate a balloon with a sufficient amount of contrast or other fluid so that the balloon may be inflated to its nominal or desired beginning OD. For example, the injection of a pre-determined volume may be sufficient to inflate a balloon to a nominal OD or initial OD within a blood vessel that may or may not be an OD sufficient to occlude the blood vessel. Note that an initial inflation, volume, pressure, OD, and the like may refer to the first intentional inflation of the balloon using an inflation device such as a syringe or inflation-deflation device, for the current use or procedure, or for the current region of interest. A deflation pressure or volume may be defined as a pressure or volume of fluid at which the pressure of the fluid on the walls of the balloon and subsequently in the catheter or conduit through which the fluid is communicated with the balloon is at a lower pressure than the blood in the vessel and sufficiently low to cause flow out of the balloon. For example, a deflation pressure or volume may be sufficient to deflate a balloon to a minimal OD sufficiently rapidly to allow the balloon to be conveniently advanced or withdrawn within a blood vessel, or to allow perfusion of a blood vessel when desired. In some cases, a deflation pressure or volume may represent the pressure or volume of an aspiration fluid or liquid, such as fluid or liquid used to fill an inflation system, an inflation-deflation device and/or catheter to be free of air or gas to minimize "bubbles" in the liquid or fluid in communication with the occlusion balloon. Such a fluid or liquid may be a contrast solution. A device or system that has had its air removed and replaced with a fluid is said to have been aspirated. Also, the deflation pressure or volume may define a single or different pressures or volumes for any single balloon. Those pressures or volumes may also define a range of pressures and volumes for a single balloon. Moreover, they may define a single, different, and/or a range of pressure and volumes for various balloons having different sizes, shapes, materials, and thicknesses.

Furthermore, as shown in FIG. 6, it is considered that retaining pins 660 and 662 may have an appropriate length to prohibit indexing locks 152 and 154 from moving further towards proximal end 106 than recess 586. Thus, in one embodiment, indexing locks 152 and 154 do not move proximally beyond proximal end 555 of cowling 580 and are not exposed (e.g., indexing locks are kept along the inner surface of cowling 580). Alternatively, in some embodiments, retaining pins 660 and 662 may have a length to allow indexing locks 152 and 154 to extend proximally beyond proximal end 555, such as to define a releasably latched position of latch 650, where locks 152 and 154 are locked at proximal end 555, such as the description above with respect to those locks and proximal end 155 of FIG. 2. In such a situation recess 586 may define another mid-latch position that may be used for the initial inflation of a different balloon, a balloon with a larger formed volume, or the same balloon to a larger initial OD. In some embodiments, multiple mid-latch positions may be provided.

Figure 8:
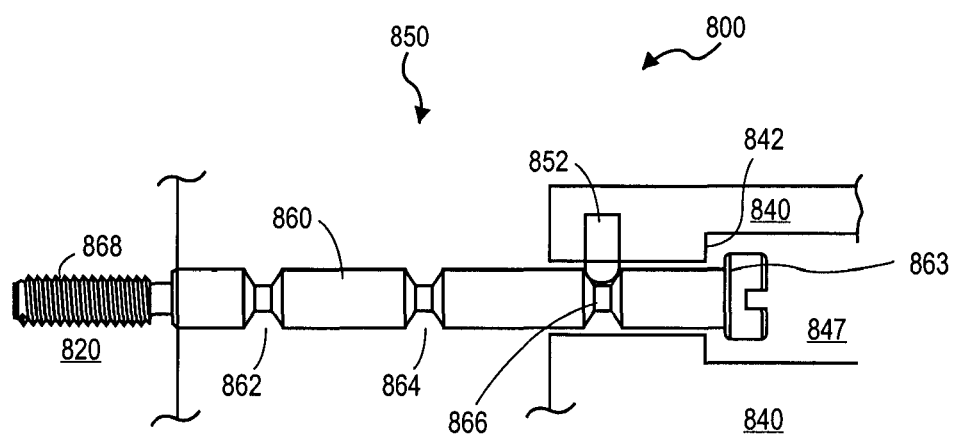
FIG. 8 is a schematic side view of a retaining pin of an integrated controlled volume inflation-deflation device having a recess engaged by an index lock of the proximal housing of the controlled volume inflation-deflation device that performs the initial inflation of a balloon using a pre-determined inflation volume.

FIG. 8 is a schematic cross-sectional side view of a retaining pin of a controlled volume inflation-deflation device having a recess engaged by an index lock of the proximal housing of the controlled volume inflation-deflation device. FIG. 8 shows structure 800 including retaining pin 860 attached to distal housing 820 by threads 868. Retaining pin 860 also has stopping surface 863 within space 847 of proximal housing 840. Proximal housing 840 includes housing stop surface 842. Thus, when distal housing 820 and proximal housing 840 are moved away from each other, stop surface 863 may engage, abut against, or stop at housing stop surface 842 to prohibit proximal housing 840 from extending a selected distance away from distal housing 820. In addition, FIG. 8 shows pin 860 having pin recesses 862, 864, and 866 along the length of the pin. Recesses 862, 864, and 866 may be beveled grooves, holes or other recesses or structures to hold a releasably latch indexing lock as described above with respect to recess 142 and FIG. 1B. For instance, recesses 862, 864, and 866 may each be a radial groove at a location along a length of the retaining pin to engage an indexing lock. Proximal housing 840 is shown with indexing lock 852 releasably latched or locked to pin recess 866.

It is contemplated that structure 800 may be used as part of a controlled volume inflation-deflation device, such as in place of pins 160 and 162 and the releasable latches of FIGS. 1A, 2-6 (e.g., structure 800, without groove 864, may obviate the need for locks 152 and 154, and recesses 182 and 184 of FIGS. 1A, 2 and 3, and recesses of structure 400 of FIG. 4 and, with groove 864, the recesses of structure 500 of FIGS. 5 and 6). Thus, structure 800 (e.g., lock 852 engaging recesses 862, 864, and 866) provide the functionality of releasable latch 150 and a corresponding releasable latch of including structure 400 and 500 of FIGS. 4-6 to releasably lock an inflation-deflation device in an inflation latched position (e.g., position INFLAT of FIGS. 1A and 3), deflation latched position (e.g., position DEFLAT of FIG. 2), and/or mid-latched position(s) (e.g., position MID of FIG. 6). For example, indexing lock 852 of proximal housing 840 may engage recess 862 when the controlled volume inflation-deflation device is in the inflation latched position, may engage recess 864 when the device is in a mid-latch position, and may engage recess 866 when the device is in the deflation latched position to move plunger 110 along length L similarly to the function of those positions as described above for FIGS. 5 and 6.

Indexing lock 852 may engage recesses 862, 864, and 866 similarly to the description above with respect to indexing lock 152 engaging recesses 582, 588, and 586 as shown and described with respect to FIGS. 5 and 6, to define an inflation latched, a mid-latched, and a deflation latched positions, such as positions that may correspond to inflating a balloon with a pre-determined inflation volume as described above with respect to those recesses. Thus, similarly to the description above with respect to using recesses 182 and 184, or other recesses of FIGS. 4-6 to be engaged by indexing locks 152 and 154, pin recesses 862, 864, and 866 may provide releasable latch 850.

Also, pin 860 may be a pin as described above with respect to pin 160, and surface 863 may be a surface as described above with respect to surface 163, such as to restrain or restrict movement of the proximal and distal housing sections when the controlled volume inflation-deflation device is in the deflation latched position to stop indexing locks at recesses, distal to a proximal end of a cowling, or proximal to a proximal end of a cowling. Thus, in some cases, retaining pins 160 and 162 may be pin 860 of FIG. 8 without pin recesses 862, 864, and 866 along the length of the pin.

In addition, it is also contemplated that structures like housing stop surface 842 and retaining pin stop surface 863 may be used to attach a pin like pin 860 to a distal housing or to prevent a pin like pin 860 from disengaging from a distal housing. Also, it is contemplated that pin recesses 862, 864, and 866 may be engaged by an indexed lock of either the distal or proximal housing in either of the configurations described above (e.g., regardless of whether threads 868 are attached to a distal or proximal housing).

Figure 9:
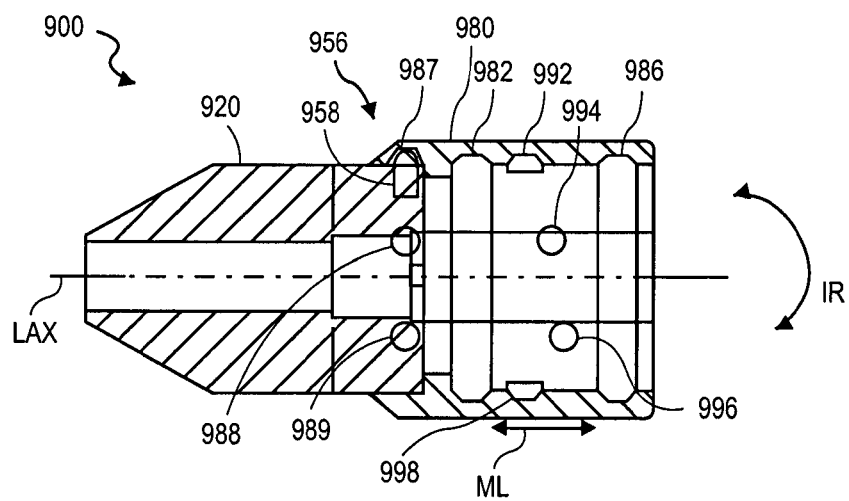
FIG. 9 is a schematic cross-sectional side view of a cowling and distal housing of an integrated controlled volume inflation-deflation device having a rotational index and recesses along a longitudinal length of the inner surface of the cowling corresponding to indexing positions of the rotational index that performs the initial inflation of a balloon using various pre-determined inflation volumes.

FIG. 9 is a schematic cross-sectional see-through side view of a cowling and distal housing of an integrated controlled volume inflation-deflation device that conveniently inflates balloons to an initial OD using pre-determined inflation volumes and having a rotational index and recesses along a longitudinal length of the inner surface of the cowling and corresponding to indexing positions of the rotational index. One way that housing and cowling of structure 900 of FIG. 9 is different from those of structure 400 of FIG. 4 is that in structure 900 they are separated into two separate components, while in structure 400 they can be a single component. FIG. 9 shows structure 900 having distal housing 920 rotationally coupled to cowling 980 by rotational indexing device 956. Indexing device 956 may include the distal portion of cowling 980 with recesses and indexing lock 958 to engage those recesses. Cowling 980 includes recesses 987, 988, 989, 982, 992, 994, 996, 998, and 986. Distal housing 920 has longitudinal axis LAX and includes indexing lock 958. Other than indexing lock 958 and the separation of the cowling 980 from the distal housing 920, distal housing 920 may be similar to distal housing 520. Recesses 982 and 986 may be similar to recesses 582 and 586. Also, lock 958 may be a ball nose spring plunger or other structure such as those described above with respect to indexing lock 132 and FIG. 1B. Likewise, recesses 987, 988, 989, 992, 994, 996, and 998 may be beveled grooves, holes or other recesses or structures to hold a releasably latch indexing lock as described above with respect to recess 142 and FIG. 1B. Recesses 987, 988 and 989 may further be deeper parts of a radial groove around the inside circumference of the distal end of cowling 980, such that indexing lock 958 retains cowling 980 on the proximal end of distal housing 920. Alternatively or in addition, other mechanical structures may be provided to retain the longitudinal relative position of the distal housing 920 to the cowling 980, while allowing them to rotate relative to each other.

Rotational indexing device 956 may include indexing lock 958 to hold or releasably lock in rotational positions with respect to axis LAX by engaging recess 987, 988, or 989 to index rotation of cowling 980 with respect to distal housing 920 at positions defined or selected by the location of recess 987, 988, and 989. Specifically, cowling 980 may be rotated with respect to distal housing 920 in directions IR around longitudinal axis LAX to engage recess 987, 988, or 989 with lock 958. Moreover, recesses 992, 994, and 996 may correspond to the rotational positions defined by the location of recesses 987, 988, and 989, where recesses 982, 984, and 996 are spaced along length ML between recesses 982 and 986.

In some embodiments the indexing lock is a ball nose spring plunger, a round nose spring plunger, a radial spring, or an o-ring (e.g., see FIG. 1E). Also, the cowling recess may be a hole in the cowling, a blind hole in the inner surface of the cowling, such holes with beveled and/or straight sidewalls, or a beveled and/or straight sided groove extending radially around the inner surface of the cowling with respect to a longitudinal axis of the proximal housing. In some cases, a cowling recesses (e.g., recess 992, 994, 996, and/or 998) may be square, a counterbored blind hole, or a drilled through hole with or without beveled sides. For instance, a round or circular hole may be used because a square recess may be quite a bit more difficult to fabricate than the circular recess (e.g., than just a drilled hole). It can be appreciated that such recesses may be designed with any number of sides to engage the index lock(s) in a desired manner. As mentioned above, in any instance described herein of an indexing lock and recess, the structure or location of the indexing lock and recess may be reversed, where possible.

Similar to the description above with respect to structure 400 of FIG. 4, structure 900 may be used as part of a controlled volume inflation-deflation device, such as by replacing distal housing 120 and cowling 180 as shown in FIGS. 1A, 2 and 3. Thus, structure 900, including device 956; recesses 982, 992, 994, 996, 998, and 986; locks 152 and 154; and pins 160 and 162 may form a latch to select between an inflation latched position, a deflation latched position, and various mid-latched positions, if applicable, as described above with respect to FIGS. 1A, 2-6 and 8. Specifically, when lock 958 engages recess 987, 988, or 989, lock 152 may engage the corresponding one of recess 992, 994, and 996 along length ML to locate plunger 110 at a location along length L when structure 900 is incorporated as part of a controlled volume inflation-deflation device, such as to lock in a mid-latched position. Hence, in an integrated controlled volume inflation-deflation device, structure 900 may provide a functionality similar to structure 500 in its ability to provide various pre-determined volumes of fluid to various occlusion balloons, such as after the balloons are aspirated and advanced to a region of interest of a blood vessel. For example, by rotating cowling 980 in directions IR, lock 958 may lock to recesses 987, 988, or 989 to removably lock rotational indexing device 956 at rotational positions to locate plunger 110 between location L1 and L2 as described above with respective FIGS. 1A and 2, when lock 152 engages recesses 992, 994, or 996 to latch the inflation-deflation device at various mid-latched positions. Likewise, lock 152 engaging one of recesses 992, 994, and 996 and then transitioning the latch to the inflation latched position (lock 152 engaging recess 982) may correspond to inflating a balloon with a pre-determined inflation volume as described above with respect recess 588 of FIG. 5. Recall that the proximal housing 140 may not rotate relative to the distal housing 920 due to retaining pins 160 and 162, thus the paths of indexing locks 152 and 154 may only encounter one pair of recesses like recesses 992, 994, or 996 and their corresponding mates. Also, locks 152 engaging recesses 982 may correspond to the inflation latched position as described above with respect to recesses 582 of FIG. 5.

It can be appreciated that recesses similar to 992, 994, and 996 may exist for engagement of locks other than lock 152. Specifically, FIG. 9 shows recess 998, such as a recess corresponding to recess 992 but for an indexing lock other than lock 152. Thus, while lock 152 is engaging recess 992, another lock, such as lock 154, may engage recess 998, and when lock 152 engages recess 994, the corresponding lock may engage a recess at a position along length ML similar to that of recess 994, and when lock 152 engages recess 996, a corresponding lock may engage a recess along length ML at a position similar to that of recess 996. It is also contemplated that structure 900 may include a stop similar to stop 490 as described above with respect to FIG. 4 and a proximal end similar to proximal end 455 as described above with respect to FIG. 4.

Furthermore, distal housing 920 may include index locks in addition to lock 958, and cowling 980 may include indexing recesses in addition to recesses 987, 988, and 989. Similarly, cowling 980 may include recesses for additional indexing positions and may include additional corresponding recesses or locks at various positions along length ML similarly to the description of various mid-latch positions above with respect to structure 500. As such, when incorporated in a controlled volume inflation-deflation device, structure 900 may be used to provide pre-determined volumes of fluid to various volumes, sizes, and designs of occlusion balloons after the balloons are aspirated and advanced through a blood vessel and positioned at a region of interest.

In other embodiments, cowling 980 and distal housing 920 may contain additional features that indicate the particular mid-latch position that the current rotational orientation of the cowling 980 relative to distal housing 920 corresponds to in a manner that allows the user to adjust the rotationally orientation to the mid-latch position that corresponds to the initial inflation volume or OD of the balloon in use. For instance, a pointing mark can be printed on the OD of cowling 980 that points toward a series of symbols or marks on the OD of distal housing 920. Those symbols or marks would indicate the appropriate balloon or the currently set initial inflation volume. In other embodiments, a releasably latched rotational orientation of the cowling 980 relative to distal housing 920 may not contain a mid-latched position. It is preferred that an integrated controlled volume inflation-deflation device of this type be packaged such that no mid-latched position is selected. Thus, the operator is required to adjust the rotational orientation of the cowling 980 relative to distal housing 920 to select the appropriate mid-latched position for the balloon in use or initial balloon OD desired. Otherwise, the operator will find a mid-latched position ready for use that may not be appropriate or safe for the balloon in use and the operator will not be reminded to adjust the rotational orientation of the cowling 980 relative to distal housing 920 to select the appropriate mid-latched position by being unable to find a mid-latched position.

Also, according to some embodiments, for any of the inflation-deflation devices described above with respect to FIGS. 1-9, the relationships and/or concepts described with respect to the cowling and the proximal and distal housings may be reversed. Specifically, the cowling may be attached to the proximal housing and have indexing/recess relationships with the distal housing (e.g., all references above to the proximal and distal housings are exchanged).

Figure 10:
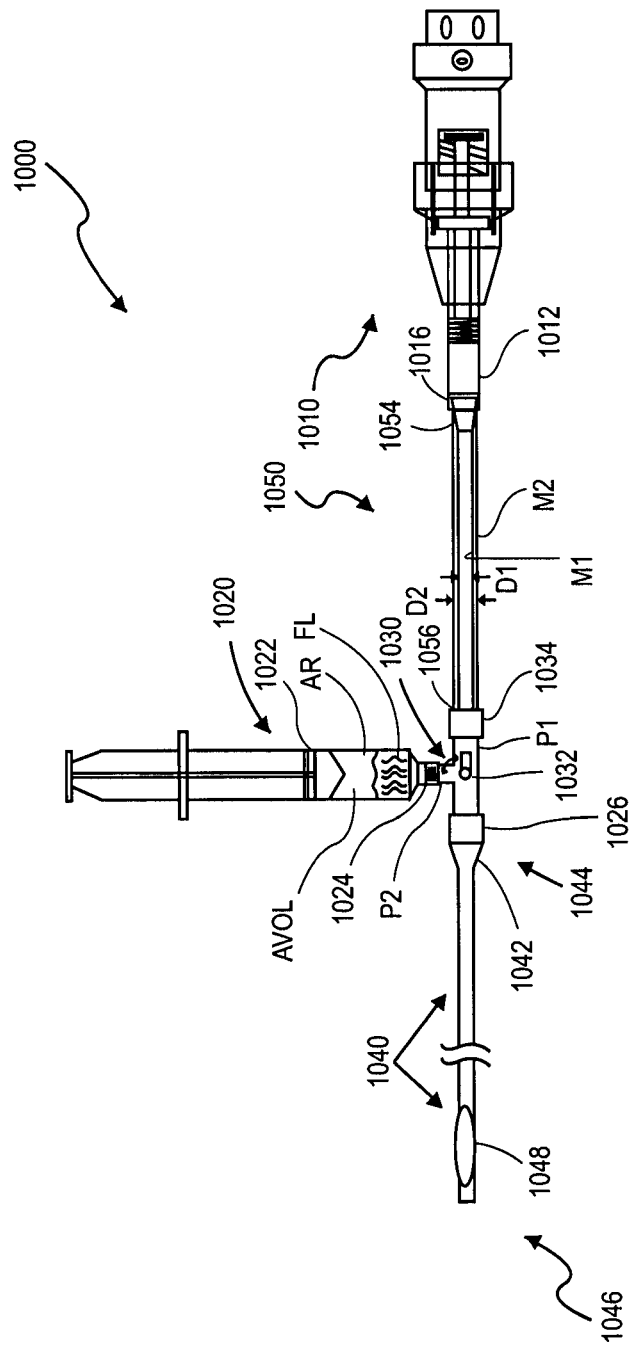
FIG. 10 is a schematic side view of one embodiment of an inflation system including a partial see through view of an integrated controlled volume inflation-deflation device that performs the initial inflation of a balloon using a pre-determined inflation volume attached to an extension tube attached to a stopcock that is attached to a catheter having a balloon at its distal end and attached to an aspiration syringe for aspirating the balloon and catheter.

Furthermore, prior to occluding a blood vessel with a balloon or inflating an occlusion balloon, it is desired to aspirate air or gas from within the catheter or balloon and replace it with fluid or liquid to provide better control and predictability of the inflation or outer diameter of the balloon during inflation. This is because air or gas compresses much more than fluid or liquid when under pressure. Such aspiration or air evacuation may be performed at low pressure, such as pressure below atmospheric pressure (e.g., below one (1) atmospheres (ATM), or approaching zero (0) pounds/square inch (PSI)). For example, FIG. 10 is a schematic side view of one embodiment of an inflation system including a partial see through view of an integrated controlled volume inflation-deflation device that performs the initial inflation of a balloon using a pre-determined inflation volume attached to an extension tube attached to a stopcock that is attached to a catheter having a balloon at its distal end and attached to an aspiration syringe for aspirating the balloon and catheter. FIG. 10 shows system 1000 having aspiration syringe 1020 attached to detachable connector 1024 of two-way stopcock 1030, which is attached to catheter 1040 having balloon 1048 attached at or near distal end 1046. System 1000 also includes integrated controlled volume inflation-deflation device 1010 having tip 1016 of syringe tube 1012 attached to connector 1054 of extension tube 1050. Integrated controlled volume inflation-deflation device 1010 may be a device similar to inflation-deflation device 600 described herein. Also, connector 1056 of extension tube 1050 is attached to connector 1034 of stopcock 1030. Thus, extension tube 1050 may be attached and sealed (e.g., such as to form a fluid and air tight seal) to integrated controlled volume inflation-deflation device 1010 and stopcock 1030. Similarly, input adapter 1042 at proximal end 1044 of catheter 1040 may be attached and sealed to distal connection 1026 of stopcock 1030. The extension tube 1050 reduces the disturbance of the proximal end of the catheter 1044 that may be introduced during the manipulation/use of the integrated controlled volume inflation-deflation device 1010 and helps prevent such things as catheter 1040 shaft kinking and undesired catheter 1040 position changes. In FIG. 10, the extension tube 1050 is shown connected to the system between the stopcock 1030 and the controlled volume inflation-deflation device 1010. In other embodiments, the extension tube 1050 may be connected between the stopcock 1030 and the catheter 1040 (device 1010 connected to the stopcock 1030) or another extension tube 1050 may be added to the system between the stopcock 1030 and the catheter 1040. In some cases, this extension tube 1050 location(s) provides needed clearance between the stopcock 1030 and the proximal end 1044 of the catheter. In some catheter 1040 designs, the proximal end 1044 of the catheter 1040 can be a very crowded place with many adjacent connections that may require a more easy access than is provided if the stopcock 1030 is connected to catheter proximal end 1044 and must be manipulated there.

Controlled volume inflation-deflation device 1010 may be described as an "integrated" controlled inflation-deflation device because it is able to initially inflate an occlusion balloon to a nominal or desired OD from a minimal OD, to inflate the balloon to an occlusion OD sufficient to occlude a blood vessel, to deflate the balloon to a sufficient OD to allow the balloon to be advanced or withdrawn within a blood vessel or to allow perfusion of the blood vessel, and then to re-inflate the balloon to the occlusion OD and deflate the balloon at will. An integrated controlled volume inflation-deflation device may be able to initially inflate an occlusion balloon to a nominal or desired OD from a minimal OD without assistance from another inflation-deflation device, such as by "integrating" that ability with the controlled volume inflation-deflation device's ability to inflate and deflate the balloon to occlude and perfuse the blood vessel. Moreover, an integrated controlled volume inflation-deflation device may be designed to initially inflate an occlusion balloon to a nominal or desired OD from a minimal OD using a pre-determined inflation pressure or a pre-determined volume of fluid. The type of integrated controlled volume inflation-deflation device that initially inflates the balloon to a pre-determined pressure will be discussed later in reference to FIGS. 7, 12 and 13. Note that the type of initial inflation of a balloon can depend on the design/material of the balloon. Some balloons are best initially inflated to a predetermined pressure and some balloons are best initially inflated to a predetermined volume (e.g., to obtain nominal OD). A compliant balloon is a balloon that has an adjustable OD beyond its formed OD, but will not return to its formed OD after having been adjusted to its maximum OD. An elastic balloon is a balloon that has an adjustable OD beyond its formed OD and will return to or very near to its formed OD after having been adjusted to its maximum OD. Often compliant balloons have a narrower range of adjustment than elastic balloons. Practical compliant balloons made of non-elastomeric polymers, such as nylon, Pebax and polyethylene, are more likely to require a formed ID greater than the OD of the catheter that they are mounted on than practical elastic balloons made of elastomeric polymers such as silicone, latex and polyurethane. Thus, a design of an integrated controlled volume inflation-deflation device may be selected for use with a certain type of initial inflation of a balloon. It is considered that device 1010 may initially inflate a balloon to its nominal or desired OD using a selected volume of fluid. Integrated controlled volume inflation-deflation device 1010 may be an inflation-deflation device similar to inflation-deflation device 100 including structure 400, 500, 800, or 900 as described herein.

Extension tube 1050 may be a pliable extension tube to connect between the controlled volume inflation-deflation device and the stopcock, or to connect between the controlled volume inflation-deflation device and the catheter. Moreover, extension tube 1050 may be flexible, but has a low compliance, such that it doesn't exhibit a substantial change in the volume within the extension tube lumen (e.g., a volume of fluid within the extension tube at zero pressure or at a pressure greater than zero) in response to bends, curves, or movement of the tube; grasping or holding the tube such as by a human hand, or pressure changes within the tube (e.g., pressure changes in a fluid within the tube).

Extension tube 1050 may have inner diameter D1 sufficient to communicate fluid between tip 1016 of syringe tube 1012 and input adapter 1042 of catheter 1040 via stopcock 1030 to cause a volume of fluid to inflate balloon 1048 to occlude a blood vessel at a region of interest. Moreover, extension tube 1050 may have inner material M1 and outer material M2 formed over inner material M1, such as by having outer material M2 surrounding and/or extruded over inner material M1. It is also contemplated that material M1 and material M2 may be miscible, and may be extruded to be miscible in an extrusion or co-extrusion process. In some examples, tube 1050 is formed by co-extruding miscible materials M1 and M2 so that material M2 bonds with material M1 before material M1 dries, sets, solidifies, and/or cools during the co-extrusion.

It can be appreciated that an extrusion or co-extrusion process may include heating one or more volumes of materials to a melting point and extruding the materials out of an aperture or orifice over an air pressure line or tube. Thus, material M1 and material M2 may dissolve into each other, be chemically miscible, and/or have a boundary therebetween including a depth of atoms that are a mixture of material M1 and material M2. Specifically, for example, a co-extrusion process may include simultaneously extruding a tube of the inner material and a tube of the outer material onto or over the first material so that the materials form a miscible interface of the first material and the second material therebetween. Such co-extrusion may use a single "extruder" or device having two chambers that heat a volume of the first material and a volume of the second material to a melting point, and then extrude the first material and the second material over the first material over a pressurized air opening of a tube or over a mandrel of an extrusion die. For instance, the extruder may use a screw mechanism or pressure device in each chamber to force the melted materials out of two apertures or orifices in a die chamber to extrude the material out of the die opening over a hollow mandrel with pressurized air feeding it ID.

In other embodiments, where materials M1 and M2 are not miscible with each other, an adhesive polymer (e.g., intermediate polymer) may be extruded between them to bond them together in a tri-layer co-extrusion process. In other embodiments, other conventional processes are used to bond/bind together the interface of materials M1 and M2. In other embodiments, the interface of materials M1 and M2 is not bonded or bound together and special connectors are used that provide bonding surfaces for each of the tubes made of materials M1 and M2.

FIG. 10 shows extension tube 1050 having inner diameter D1 and outer diameter D2. In one example, diameter D1 (an inner diameter) is less than or equal to 0.035 inches and diameter D2 (an outer diameter) is greater than or equal to 0.13 inches. It is contemplated that the wall thickness of material M1 may be 0.015 inches or less. However, there can be considerable variation in the D1, D2 and wall thicknesses that may be chosen, depending upon M1 and M2 material properties and still produce a tube with acceptable flexibility and acceptable low compliance. Furthermore, inner material M1 may be a polymer/plastic, preferably a relatively high modulus translucent material such as nylon or HDPE. Also, outer material M2 may be a polymer/plastic, preferably a relatively low modulus translucent material that is miscible with material M1, such as Pebax or LDPE, respectively. The high modulus inner portion of the tube 1050 (material M1) provides the low compliance/low volume change properties of tube 1050. The low modulus outer portion (material M2) of the tube 1050 provides support to the inner portion to provide kink resistance and may be used to increase the tube 1050 OD to the OD of conventional extension tubes for tube 1050 compatibility with conventional extension tubing connectors, such as connectors 1054 and 1056, while maintaining an acceptable level of flexibility. Moreover, it is preferred that materials M1 and M2 be bonded together, either by a bonding agent or due to their being miscible, to facilitate the attachment of conventional connectors. Thus, extension tube 1050 may be a flexible tube that does not encounter significant volume changes within tube 1050 when flexing, bending, or being grasped, pushed, or held by a human hand or in response to pressure changes within its ID. Also, material, thicknesses, and diameters of extension tube 1050 may be selected so that tube 1050 resists kinking, has a lower compliance and/or is more flexible than a tube made entirely of any single material at any given D1 and D2. Moreover, material M1 and M2 may be translucent materials so that air bubbles are visible within extension tube 1050 to facilitate ensuring that air is removed from the system.

Balloon 1048 (in a deflated and/or folded condition) and catheter 1040 have a dimension suitable for percutaneous advancement through a blood vessel, such as to a region of interest. Moreover, balloon 1048 has a property such that it may inflate to an outer diameter that will occlude a blood vessel at a region of interest when it is inflated with an inflation volume, and may be deflated to perfuse blood to the blood vessel when it is deflated to a deflation volume.

Aspiration syringe 1020 is shown having volume AVOL filled with fluid FL. Typically, aspiration is best done by a syringe that has no air in it to begin with. After the aspiration, the syringe may have the air from the balloon/catheter in it. For more details, see description below about the details of aspiration. Volume AVOL is a volume sufficient to aspirate catheter 1040 and balloon 1048, such as to remove air from spaces therein and fill those spaces with a liquid/fluid from the aspiration syringe 1020.

Stopcock 1030 includes position lever 1032 which may be switched between position P1 and position P2. For example, when position lever 1032 is in position P1, flow may be prohibited between extension tube 1050 and stopcock 1030. Thus, aspiration syringe 1020 may be used to aspirate catheter 1040 and balloon 1048 when lever 1032 is in position P1. When lever 1032 is in position P2, flow may be blocked between aspiration syringe 1020 and stopcock 1030. Thus, aspiration syringe 1020 may be removed from stopcock 1030 when lever 1032 is in position P2 without a flow of air or liquid escaping from or entering stopcock 1030.

Moreover, volume AVOL and a seal between plunger 1022 and the sidewall of aspiration syringe 1020 may be sufficient to aspirate catheter 1040 and balloon 1048, such as for volume AVOL to be filled with a minimal pressure or volume of air (e.g., such as close to 0 PSI of liquid and few bubbles of gas in the liquid). The ability to aspirate as described below allows balloon 1048 and communicating lumens to be filled with fluid and very little air, such as before, during or after insertion of balloon 1048 percutaneously through a blood vessel to a region of interest. Moreover, system 1000 allows aspiration syringe 1020 to be removed from detachable connector 1024 of stopcock 1030 after catheter 1040 and balloon 1048 are aspirated and filled with a liquid.

According to some embodiments, during an aspiration process the balloon on the catheter is folded/deflated before and during the aspiration process. If not, it may immediately become deflated and stays deflated during the aspiration process. In use, the syringe 1020 is filled with a small amount of fluid and very little or no air. To begin the aspiration, the syringe plunger is withdrawn. This withdrawal creates a space between the fluid in the syringe and the plunger, which has very little, if any air in it and now has a very low pressure. It is important that no air slips past the plunger and enters the syringe, as this will cause a loss of the low pressure (the pressure inside the syringe will increase). The created low pressure in the syringe is felt by the air in the catheter's balloon inflation lumen and inside the balloon, which causes the air to expand. As this air expands, it has nowhere to go but to bubble up through the fluid in the syringe and into the empty space AR between the top of the fluid and the syringe plunger. The lower the pressure in the syringe/the further the syringe plunger is withdrawn, the more this air expands and the more of the air inside catheter/balloon bubbles up into the syringe. The air bubbling into the syringe causes the pressure inside the syringe to rise. Once the air remaining in the catheter's balloon inflation lumen and inside the balloon reaches nearly the same pressure as the pressure inside the syringe, the bubbles stop coming into the syringe, the syringe is flicked with the finger to ensure that only fluid is at the bottom of the syringe (removes air bubbles from the fluid) and then the syringe plunger is allowed to advance in the syringe, raising the pressure in the syringe until the pressure in the syringe is pretty much equalized with atmospheric pressure. This atmospheric pressure is felt by the remaining air in the catheter's balloon inflation lumen and inside the balloon, which causes the air in them to compress. As the remaining air compresses, fluid from the syringe flows into the catheter's balloon inflation lumen and inside the balloon until the remaining air inside the catheter/balloon reaches near atmospheric pressure and no longer continues to occupy less and less volume. The syringe is removed from the stopcock, the air in the syringe (from catheter's balloon inflation lumen and inside the balloon) is removed, the syringe reattached to the stopcock and the process repeated one or more times to remove most of the air and replace it with fluid.

Aspiration may be used to remove air from the system because air may cause problems with controlled volume inflation system operation because it is so compressible. So, to prevent such problems, the system components can be filled with fluid and assembled in a manner that ensures that all or most of the air from the system components (e.g. stopcock, extension line, aspiration syringe, controlled volume inflation-deflation device, and the like) and fluid air bubbles are removed prior to connecting them to the catheter. Additionally, all connections may be made with the mating connector surfaces wetted/filled with fluid, as this ensures an air and fluid tight connection and avoids air being introduced into the connectors during the connection process (a "wet connection" process). This ensures that air will not get into the system during system assembly and air and fluid will not get out of or into the system during balloon inflation and deflation. Without these processes, the OD of the balloon may not be controlled in a predictable manner. In some cases, system 1000 may be used when performing the process of FIG. 11.

Also, system 1000 may be used for aspirating the balloon and inflation lumen of catheter 1040 and then inflating the balloon to its nominal OD by moving the latch of device 1010 from a mid-latch position to an inflation latched position (e.g., a most distal position) and then adjusting the balloon OD in increments until occlusion using the proximal knob of device 1010. The balloon may then be deflated by moving the latch of device 1010 to its deflation latched position (e.g., a most proximal position). Moreover, after inflation, the balloon may be inflated/deflated to control the occlusion at will. Syringe 1020 may be removed from the stopcock after the aspiration once the stopcock's lever is turned to point at the syringe, cutting off the flow from the syringe and connecting device 1010 to catheter 1040's inflation lumen. In some cases, it is preferred that the aspiration be done once the balloon is in position in the body/vessel, otherwise the inflation system must be moved along with the catheter during the insertion procedure, which is very clumsy/somewhat impractical. Additionally, if the catheter/balloon is aspirated prior to insertion and balloon positioning (for example by a syringe), then "wet" connecting the integrated controlled volume inflation-deflation device 1010 to the catheter's inflation lumen can result in fluid being forced into the catheter 1040 and balloon 1048, causing the balloon 1048 to become partially inflated. Unless the operator is going to immediately use the system to obtain an occlusion, this partial inflation can be considered to be a safety hazard that may impede vessel blood flow and engage the anatomy or other devices if the catheter/balloon is re-positioned. Furthermore, the volume of fluid that may be forced into the catheter 1040 and balloon 1048 during the wet connection process is unpredictable, as it is dependent upon the amount connection wetting/amount of fluid present in the connections and the speed of their connection. When using an integrated controlled volume inflation-deflation device like device 1010, which initially inflates the balloon 1048 by injecting a predetermined volume of fluid, this variable volume can introduce an undesirable balloon 1048 OD uncertainty. If the catheter/balloon is aspirated using the system shown in FIG. 10 when the balloon 1048 is in the occlusion position in the vessel, the wet connection between the stopcock 1030 and the catheter 1040 occurs with the catheter/balloon filled with very compressible air. Thus, the air compresses as the small amount of wet connection fluid is forced into the catheter's inflation lumen, producing a very small pressure rise in the balloon that is not a high enough pressure to partially inflate the balloon. Then, when the inflation system is connected to the balloon inflation lumen of the catheter and the catheter/balloon is aspirated, there is no extra or variable fluid volume introduced into the system and the balloon is left in the deflated condition. Thus, using an inflation system such shown in FIG. 10 encourages the user to naturally follow a procedure that aspirates the catheter/balloon once the balloon is in the occlusion position in the vessel and, thus avoid potential safety issues and balloon OD uncertainties.

Furthermore, an example process for using system 1000 in FIG. 10, or a like system, is described by the following operations:

1. The integrated controlled volume inflation-deflation device 1010 is attached to extension tube 1050 (wet connected) and they are filled with contrast solution such that no bubbles or air voids are present. This is done by placing or attaching the end of the extension tube 1050 in or onto a contrast solution source and pulling the device 1010 into its deflation position to pull contrast solution into it. The device 1010 may then be pointed up and transitioned (pushed together) to its inflation position to push the air out of the syringe tube 1012 and extension line 1050. This may involve hitting the device 1010 into your hand to dislodge bubbles, additional transitions of the deflation/inflation positions and the pulling in of more contrast solution. The device 1010 is left in a mid-latched position appropriate for the vessel, balloon 1048 and catheter 1040.
2. The aspiration syringe 1020 (20 ml) is filled with about 4-5 ml of dilute contrast media and de-bubbled.
3. The catheter 1040 is positioned in the patient's coronary artery or other vessel of interest and the balloon 1048 is positioned at the desired occlusion position.
4. The aspiration syringe 1020 is wet connected to the stopcock 1030.
5. Using the fluid in the aspiration syringe 1020 and manipulating lever 1032, the stopcock 1030 is filled with fluid and wet connected to the extension tube 1050, leaving the stopcock lever 1032 in position P1.
6. The stopcock 1030 is wet connected to the catheter's balloon inflation lumen proximal connection input adapter 1042 with the stopcock lever 1032 in the position shown.
7. The aspiration syringe 1020 is used to two times aspirate the catheter as per the standard balloon catheter aspiration practice.
8. The lever 1032 on the stopcock 1030 is rotated 90° counterclockwise to position P2 and aspiration syringe 1020 is removed.
9. The device 1010 is transitioned from its mid-latched position to its inflation position and the balloon 1048 is initially inflated to the pre-determined volume (and OD).
10. If applicable, the incremental inflation knob may be adjusted as per a chart (click or counter number to balloon 1048 OD chart) and previous vessel sizing (e.g. by fluoroscopy) to inflate the balloon to a safe OD.
11. The occlusion is tested, such as by contrast injections (e.g., via a guide catheter) or pressure readings (e.g., via a catheter 1040 lumen, a catheter 1040 infusion lumen).
12. If the desired occlusion is not attained, the inflation knob is incremented to increase the balloon 1048 OD.
13. Operations 11 and 12 are repeated until vessel occlusion is attained.
14. The integrated controlled volume inflation-deflation device is pulled apart into its deflation position to remove the vessel occlusion and allow blood flow.
15. The integrated controlled volume inflation-deflation device 1010 may then be transitioned between its inflation and deflation positions to occlude the vessel for the desired amount time(s) at the desired times as per the medical treatment or procedure protocol.
16. With the balloon 1048 deflated by the integrated controlled volume inflation-deflation device 1010 in its deflation latched position, the catheter may be re-positioned in the vessel or removed from the vessel.
17. The incremental inflation knob is adjusted as per the click to OD chart to a safe initial OD for the new vessel position or back to its initial position (e.g., zero).
18. The integrated controlled volume inflation-deflation device 1010 is transitioned to its inflation latched position and the incremental inflation knob is adjusted as previously described in operations 11-13 to attain vessel occlusion.
19. The integrated controlled volume inflation-deflation device 1010 is pulled apart into its deflation latched position to remove the vessel occlusion and allow blood flow.
20. The integrated controlled volume inflation-deflation device 1010 may then be transitioned between its inflation and deflation positions to occlude the vessel for the desired amount time(s) at the desired times as per the medical treatment or procedure protocol.
21. Operations 16 thru 20 may be repeated, as necessary.
22. With the balloon 1048 deflated by the integrated controlled volume inflation-deflation device, the stopcock 1030 may be removed from the catheter 1040 and the catheter 1040 withdrawn from the patient.
23. If the integrated controlled volume inflation-deflation device 1010 is to be re-used with a different catheter in the same patient, then the device must be returned to its initial (out of package) adjustment conditions and operations started again beginning with operation 1.

It is contemplated that operations in addition to those above may be performed when using system 1000 or a like system. Also, in some cases, fewer than all of the operations above may be performed when using system 1000 or a like system. Likewise, in some cases, the order of some of the operations above may be switched around when using system 1000 or a like system.

Figure 7A:
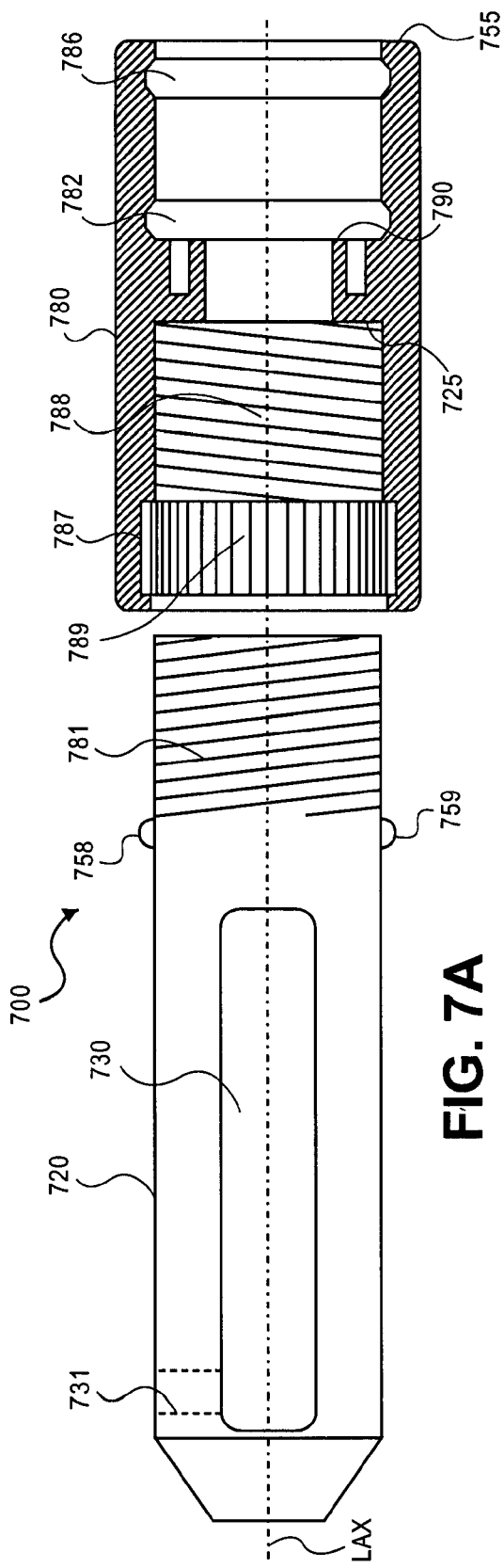
FIG. 7A is a schematic cross-sectional side view of a cowling and a side view of a distal housing of an integrated controlled volume inflation-deflation device that performs the initial inflation of a balloon using a pre-determined inflation pressure.

FIG. 7A is a schematic cross-sectional side view of a cowling and a view of a distal housing of an integrated controlled volume inflation-deflation device that performs the initial balloon inflation using a pre-determined pressure. Distal housing 720 and cowling 780 both have longitudinal axis LAX. Distal housing 720 has threads 781 on the outer surface of its proximal end. Distal housing 720 has distal housing internal features similar to those described above with respect to housing 220 to retain a syringe tube (not shown). Distal housing 720 has a cutout 730 to allow the syringe tube (not shown) to be viewed to aid ensuring that air bubbles are removed. In other embodiments, alternately or in addition, the distal housing 720 or parts of the distal housing 720 may be made of a translucent material for this same purpose. Distal housing 720 has mounting feature 731 near its distal end to support a pressure gauge (not shown) or parts of a pressure gauge (not shown) that communicates with the output of the syringe tube (not shown) to provide a readout of the inflation pressure. Distal housing 720 includes indexing locks 758 and 759. Cowling 780 has recesses 782 and 786. Recesses 782 and 786 may correspond to recesses 482 and 486 as described above in FIG. 4. Cowling 780 has slot 787 circumferentially disposed around its ID. In addition, slot 787 has gear teeth-like or other indent features 789 on its inner surface. Cowling 780 has threads 788 on its ID.

Figure 7B:
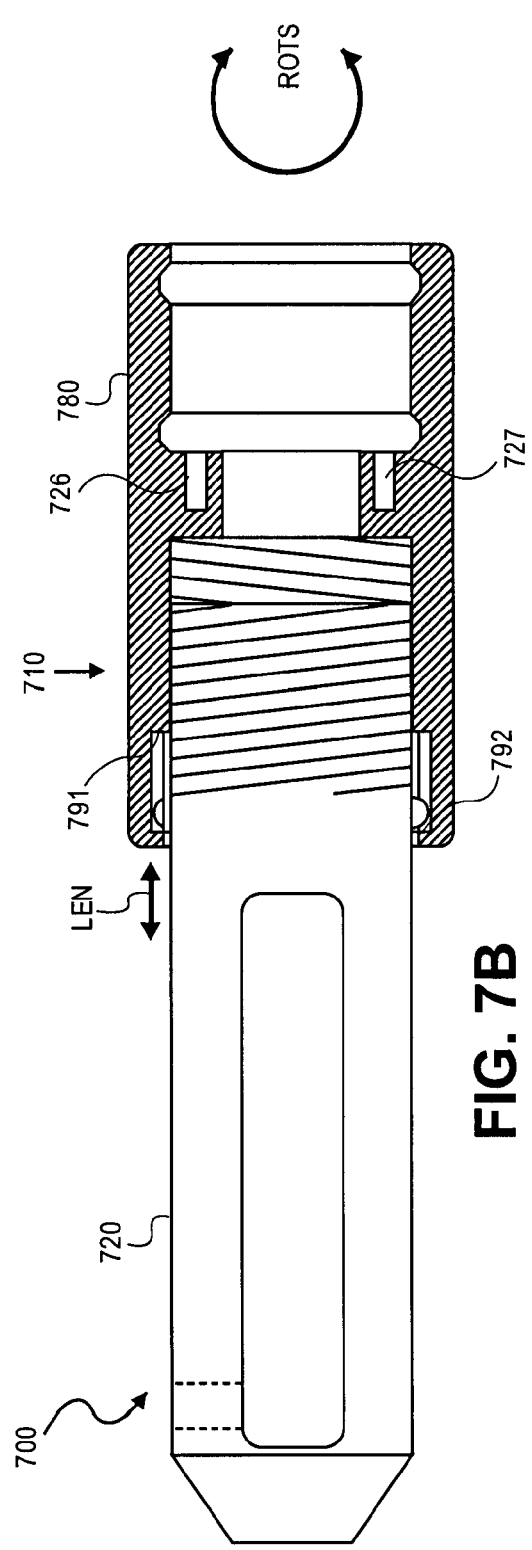
FIG. 7B is a schematic cross-sectional side view of the cowling and a side view of the distal housing of FIG. 7A, where the cowling is attached to the distal housing in the pre-initial inflation to the pre-determined pressure position.

FIG. 7B shows distal housing 720 attached to cowling 780 by pressure inflation adjustment and releasable latch mechanism 710. Cowling 780 is threadably attached to distal housing 720 via thread 788 along its inner surface engaging with threads 781 along the proximal outer surface of the distal housing 720. Cowling 780 is constrained in its distal motion relative to distal housing 720 by the engagement of indexing locks 758 and 759 with the proximal surface 791 of slot 787 and constrained in its proximal motion relative to distal housing 720 by the engagement of indexing locks 758 and 759 with the distal surface 792 of slot 787. In other embodiments, alternatively or in addition, the distal motion of cowling 780 relative to distal housing 720 may be constrained by the length of threads 781 and/or 788 and/or the interference of the proximal end of distal housing 720 with an inner surface 725 of cowling 780. Indexing locks 758 and 759 engages gear teeth-like or other indent features 789 of slot 787 such that an applied rotational force is required to rotate the cowl 780 relative to distal housing 720 and during rotation, indexing locks 758 and 759 engage gear teeth-like or other indent features 789 in a manner that provides multiple stable releasably latched/locked rotational relationships between the cowling 780 and the distal housing 720.

Thus, pressure inflation adjustment and releasable latch mechanism 710 may include threads 781 and 788 to adjust or move cowling 780 along length LEN with respect to distal housing 720. Similar to the discussion above with respect to structure 400 and FIG. 4, structure 700 may be used as part of an integrated controlled volume inflation-deflation device, such as by replacing distal housing 120 and cowling 180 of FIGS. 1A, 2 and 3. For example, a latch may be formed between locks 152 and 154 and recesses 782 and 786. Locks 152 and 154 engaging recesses 782 and 786 may correspond to inflation (first) latched position and the deflation (second) latched positions previously described with respect to structure 400 of FIG. 4. Additionally, cowling 780 may contain threaded holes 726 and 727 to engage retaining pins 160 and 162 and thus maintain the position of locks 152 and 154 relative to recess 786 when the integrated controlled volume inflation-deflation device is in the second latched (deflation) position. Thus, FIG. 7 is an example of an embodiment where retaining pins are attached to the cowling (e.g., at threaded holes 726 and 727) and extending through a portion of the proximal housing to engage a stop surface of the proximal housing. In other embodiments, it is contemplated that cowling 780 may be provided with a mid-position latching recess (es) such as those previously described in reference to FIG. 5. In those embodiments, the integrated controlled volume inflation-deflation device may either initially inflate a balloon (s) using a pre-determined volume(s) of fluid or initially inflate a balloon(s) using a pre-determined inflation pressure.

It can be appreciated that by rotating cowling 780 in rotational directions ROT with respect to distal housing 720 along longitudinal axis LAX, the position of plunger 110 of such a controlled volume inflation-deflation device may be moved along distance L of syringe tube 112 while indexing locks 152 and 154 engage recess 782 in the inflation (first) latched position. Thus, when indexing locks 152 and 154 engage recess 782, threads 781 and threads 724 may be corresponding threads sufficient in number and spacing and rotated relative to each other to move plunger 110 to push a volume of fluid into an occlusion balloon until the pre-determine initial inflation pressure is attained, as indicated on the readout of the pressure gauge (not shown), such as after the balloon is aspirated and advanced through a blood vessel such as is described above with respect to FIGS. 5 and 6. Specifically, threads 781 and threads 788 allow structure 700 to provide adjustable volumes of fluid to inflate to a pre-determined pressure various balloon sizes, materials, structures, and designs after inserting any one of the various balloons into a blood vessel and to a region of interest. Cowling 780 also includes a stop 790 similar to stop 490 of FIG. 4 and a proximal end 755 similar to proximal end 455 of FIG. 4. Because stop 790 is a part of cowling 780, the translation of cowling 780 relative to the distal housing 720 (due to the previously described rotation) will not affect the amount of the volume change within the syringe (not shown) when the integrated controlled volume inflation-deflation device is transitioned between the inflation and deflation latched positions.

Figure 12:
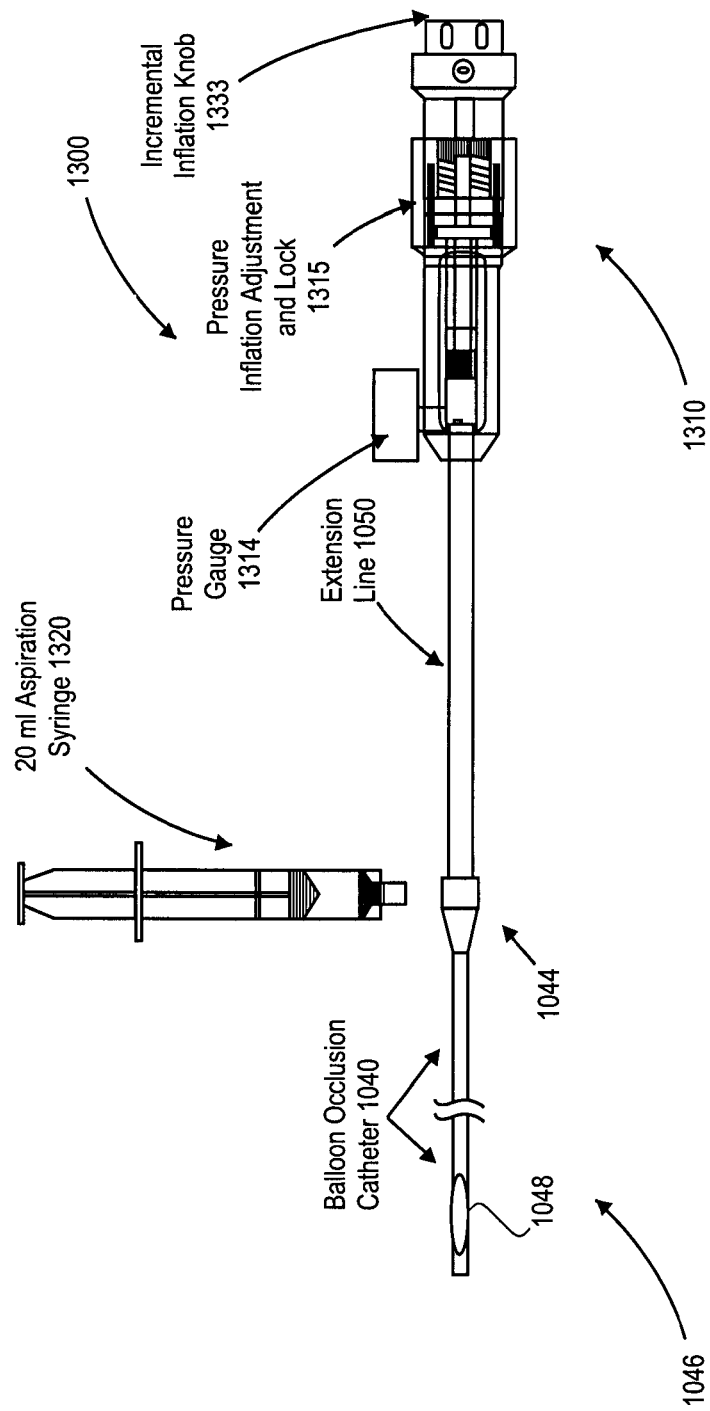
FIG. 12 is a schematic side view of one embodiment of an inflation system including a partial see through side view of an integrated controlled volume inflation-deflation device that performs the initial inflation of a balloon using a predetermined inflation pressure attached to a catheter having a balloon at its distal end and a view of the aspiration syringe.

According to some embodiments, a system may be used to aspirate as well as to inflate and deflate an occlusion balloon which includes an integrated controlled volume inflation-deflation device with a distal housing and cowling as described in reference to FIGS. 7A and 7B. For example, FIG. 12 is a schematic side view of one embodiment of an inflation system including a partial see through side view of an integrated controlled volume inflation-deflation device that performs the initial inflation of a balloon using a pre-determined inflation pressure attached to a catheter having a balloon at its distal end and a view of the aspiration syringe. In FIG. 12, integrated controlled volume inflation-deflation device 1310 may have a distal housing similar to distal housing 720 and a cowling similar to cowling 780. Device 1310 is part of inflation system 1300. FIG. 12 shows an integrated controlled volume inflation-deflation device 1310 attached to an extension tube 1050 that is attached to a catheter 1040 having a balloon 1048 at its distal end and an aspiration syringe 1320 for aspirating the balloon and catheter. FIG. 12 shows system 1300 having aspiration syringe 1320 (e.g., a 20 milliliter aspiration syringe). System 1300 also includes inflation-deflation device 1310 (e.g., an integrated controlled volume inflation-deflation device or "CVI") attached to or connected to extension tube 1050, which is attached to catheter 1040 (e.g., a balloon occlusion catheter) having balloon 1048 attached at or near distal end 1046. Thus, extension tube 1050 may be attached and sealed (e.g., such as to form a fluid and air tight seal) to inflation-deflation device 1310 and catheter 1040.

Similar to integrated inflation-deflation device 1010 of FIG. 10, device 1310 of FIG. 12 may be described as an "integrated" inflation-deflation device, since device 1310 may not require assistance from another inflation-deflation device (e.g., In FIG. 14 low volume syringe or low pressure inflation-deflation device 1420) to conveniently initially inflate an occlusion balloon to an initial or formed OD from a folded or minimal OD. Once the balloon 1048 is inflated to its initial OD using a pre-determined pressure, device 1310 is able to inflate the balloon to an occlusion OD sufficient to occlude a blood vessel, to deflate the balloon to a sufficient OD to allow the balloon to be advanced or withdrawn within a blood vessel, or to allow perfusion of a blood vessel and then to subsequently re-inflate the balloon to the set occlusion OD and deflate the balloon at will.

Also, according to some embodiments, controlled volume inflation-deflation device 1310 may be an inflation-deflation device having structure 100, 200, 400, 500, or 600 as described herein, except that device 1310 includes pressure gauge 1314 and pressure inflation adjustment and releasable latch mechanism 1315. Also, pressure inflation adjustment and releasable latch mechanism 1315 may include the pressure inflation adjustment and releasable latch mechanism 710 as described in FIGS. 7A and 7B. Moreover, inflation-deflation device 1310 may include incremental inflation knob 1333 such as knob 130.

Figure 11:
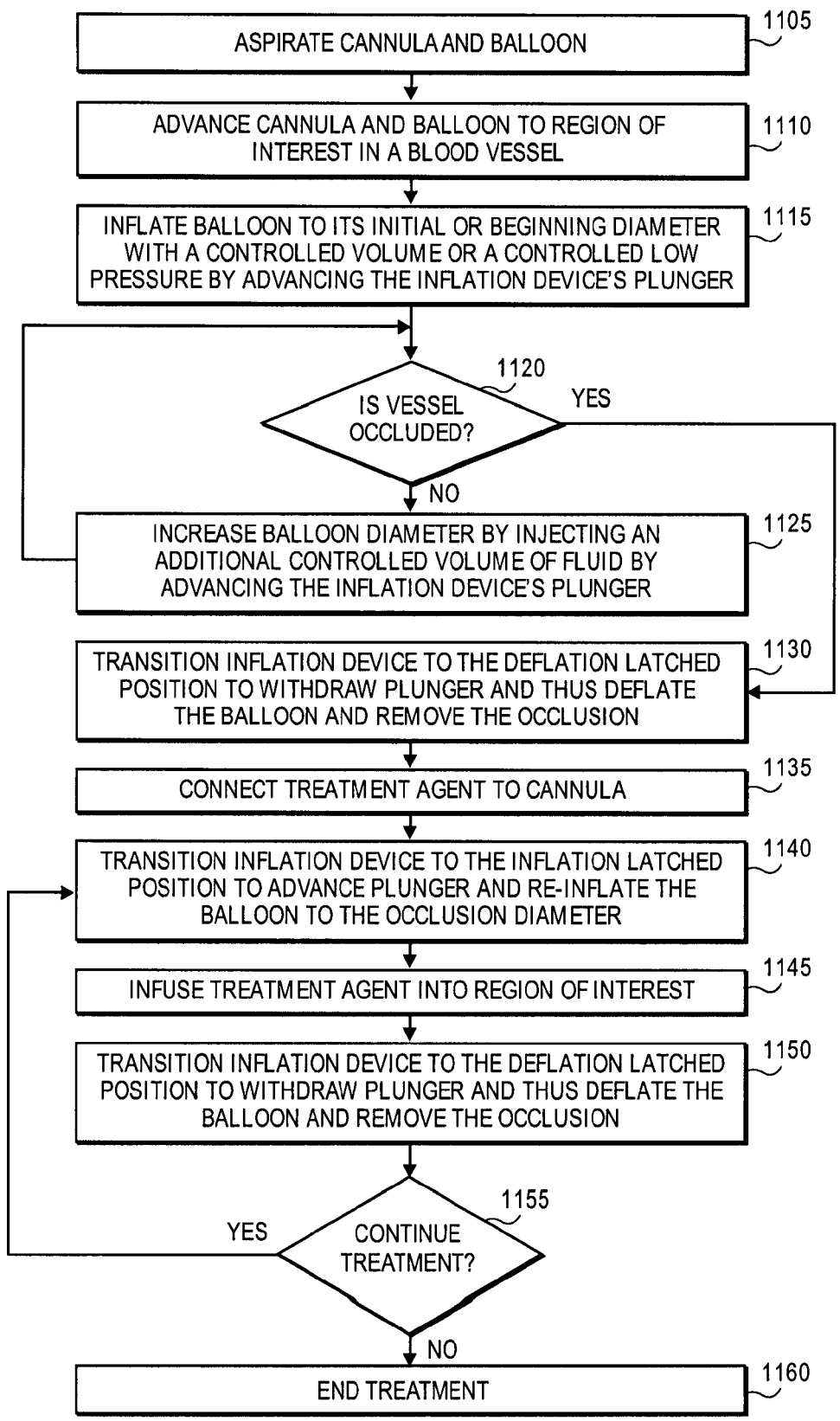
FIG. 11 is a flow diagram of a process to occlude, treat, and perfuse a blood vessel.

In some embodiments, device 1310, which may be used with compliant balloons and with balloons with a formed ID larger than the OD of the catheter shaft on which the balloon is mounted, the balloon is inflated to its initial or formed diameter by forcing fluid into the balloon at a low pressure and then using controlled increments of injected fluid to adjust its OD until occlusion (e.g., such as using device 100, and/or the processes for FIGS. 11). Device 1310 can then be transitioned from the first latched (inflation) position to the second latched (deflation) position to deflate the balloon and allow perfusion of the vessel. Then it can be transitioned between the second latched (deflation) position and the first latched (inflation) position to inflate the balloon back to that occlusion OD and occlude the vessel (stop blood flow) or deflate the balloon (allow blood flow) at will.

When device 1310 is in the first (inflation) latched position, rotation in one direction of the pressure inflation adjustment and releasable latch mechanism 1315 will cause the proximal portion of device 1310 to move toward the distal portion of device 1310. This motion causes the plunger of the syringe (constrained by the proximal portion of device 1310) to move further into the syringe body (constrained by the distal portion of device 1310) and, thus, forces fluid out of the syringe of device 1310 and into the catheter or lumen to inflate the balloon.

When the balloon has been inflated in this manner to its initial or formed diameter at a low pressure, the rotational position of the pressure inflation adjustment and releasable latch mechanism 1315 is locked relative to the distal housing. To allow the device to be re-adjusted or re-used during a procedure, this locking or latching mechanism is preferred to be releasable. One mechanism is described as part of pressure inflation adjustment and releasable latch mechanism 710 in FIG. 7. There are many conventional releasable locking mechanisms that can be employed. For example, the threaded portion of the distal end of the cowling may be longitudinally slotted and its OD threaded on an incline. These OD threads can then be engaged with new threaded cylinder. Thus, when this new cylinder is engaged with the new OD threads and further rotated, the incline causes the threads of the new proximal portion of the distal housing to be increasingly forced against its mating threads on the modified distal portion of the distal housing. The resulting friction will prevent any unintentional rotation. Rotating the new threaded cylinder in the other direction will release the threads and allow a further or a new adjustment.

Once these threads are locked, the knob 1333 on the proximal portion of device 1310 may be incremented to move the syringe plunger in longitudinal increments to incrementally force additional fluid into the balloon to adjust its diameter in the previously described manner. The balloon may also be deflated and re-inflated by transitioning device 1310 between its first (inflation) and second (deflation) latching positions in the normal manner.

Device 1310 may thus be attached to occlusion catheter/device the same manner as shown in FIG. 10. The catheter aspiration and stopcock manipulation procedures may also be the same (e.g., may include the process of FIG. 11). Alternatively, device 1310 (or device 1010 in FIG. 10) may be directly attached or preferably attached via an extension tube/line to an aspirated catheter. It is conventional for an extension line/tube, with appropriate Luer type connectors, to be a permanent part of the construction of an inflation-deflation device and such may be the case for all controlled volume inflation-deflation devices described herein. It is preferred that the extension tube/line be a low compliance type, as previously described.

According to some embodiments, gauge 1314 may be a low compliance type (like many electronic pressure gauges) and that its communication with the syringe's output flow path be such that air will not be trapped in it, as trapped air will also increase device compliance. Device compliance and differences in compliance between devices introduces balloon size (OD) variability with the same injected fluid volume. The more compliance in the inflation system, the more injected fluid volume is required to produce the same balloon size (OD) change. Such variability in the control of an occlusion balloon's OD is undesirable due to safety and ease of use considerations.

Figure 13:
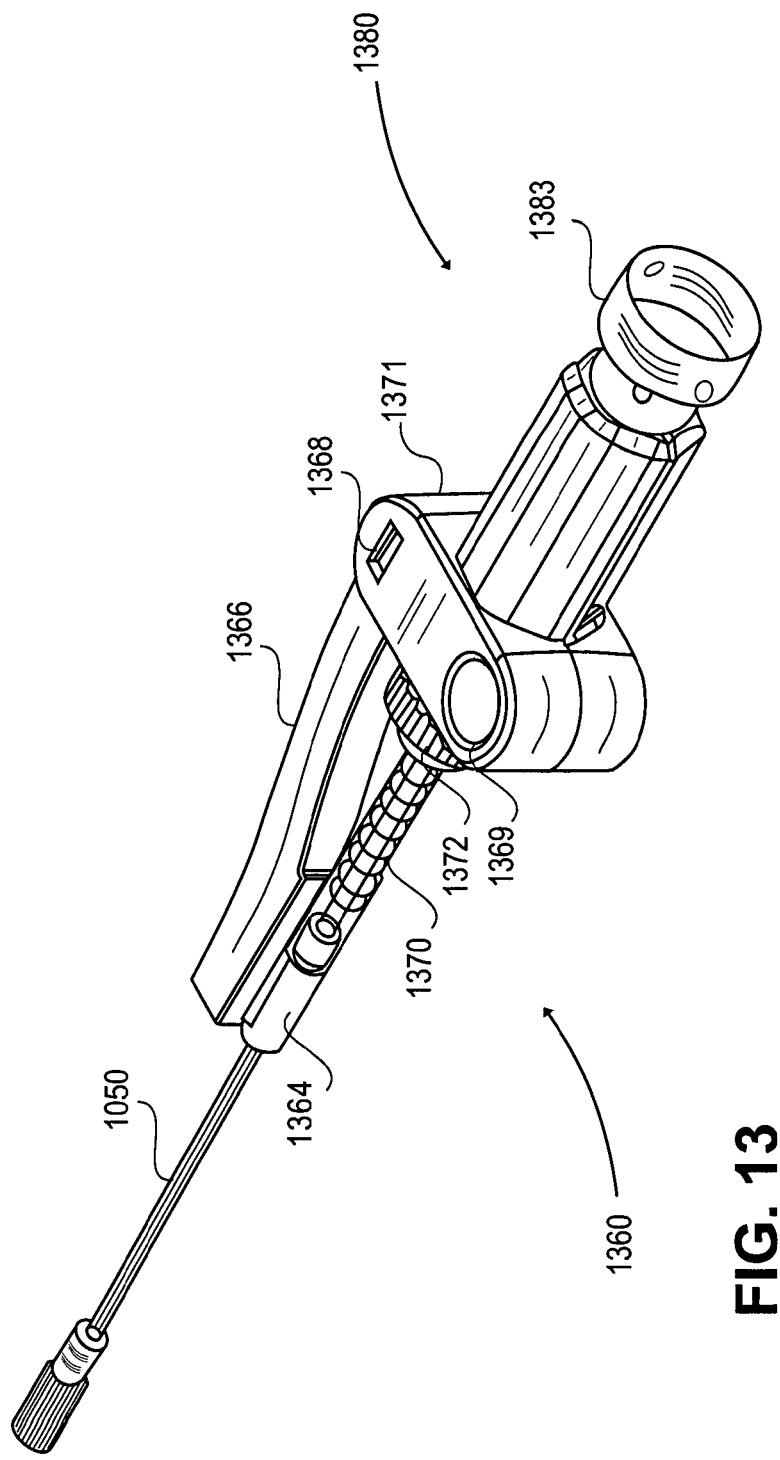
FIG. 13 is a perspective view of an integrated controlled volume inflation-deflation device that performs the initial inflation of a balloon using a pre-determined inflation pressure.

More particularly, in some embodiments gauge 1314 may be a low compliance type electronic pressure gauge. FIG. 13 shows device 1360 having syringe 1370, which is attached to an extension tube/line 1050 which may be attached to a catheter having an occlusion balloon. For instance, device 1360 can be used in place of various inflation-deflation devices described herein and is most similar to the devices described in relation to FIGS. 7A, 7B and 12. Components of device 1360 may be similar to their corresponding components of device 100, 200, 1310; and/or devices including structure 400, 500, 700, and 800. Device 1360 may be described as an "integrated" inflation-deflation device.

As shown in FIG. 13, inflation-deflation device 1360 includes pressure transducer 1364 located between syringe 1370 and extension line 1050. The electrical wires to/from the pressure transducer may run down the arm 1366 to oblong part 1371 of device 1360. The oblong part of device 1360 may house the electronics and the battery for pressure transducer 1364 and a pressure reading display. The oblong part 1371 of device 1360 may have a cut-out 1368 in it that represents the display which will indicate the pressure reading. On the opposite side of the oblong part 1371 of device 1360 can include button 1369 that must be pushed to unlock the syringe (outer body) position during the pressure adjustment. Knurled knob 1372 between syringe 1370 and oblong portion 1371 is turned to adjust the pressure of the balloon during the initial inflation (by moving the outer body of the syringe 1370) when the button is pushed. Part 1380 of device 1360 proximal of the oblong portion 1371 may be like the portions of a non-integrated inflation-deflation device (e.g., device 100 or 1410) that has the inflation and deflation releasably locked positions and proximal knob 1383 for incremental inflation/balloon OD adjustment.

For either device 1310 or 1360, if the pressure gauge is a high compliance type (like most mechanical pressure gauges), then the communicating flow path between the syringe output and the pressure gauge is preferred to be turned off after the balloon is initially inflated to a low pressure and before the incremental adjustment of the balloon's OD. Thus, in this embodiment, a shut-off valve is may be incorporated, preferably on the distal portion of device 1310. However, if the operator/physician were to forget to close this valve, then the balloon OD may not increment as expected and may fail to be able to be adjusted enough to successfully occlude the vessel or as expected. To solve this problem, a mechanism such as a spring loaded shaft may be incorporated in device 1310 such that it interferes with the longitudinal incremental manipulation mechanism and will not allow it to operate. When the valve is turned to shut off the pressure gauge, the shaft is released by a portion of the valve lever/stem and the spring moves the shaft out of the longitudinal incremental manipulation mechanism, allowing it to operate. If device 1310 is to be later re-used in the procedure, the longitudinal incremental manipulation mechanism may be returned to its starting position (i.e. increment count "0"), the shaft forced back into the longitudinal incremental manipulation mechanism and the valve opened, which retains the spring loaded shaft's position. Thus, device 1310 may be returned to it initial condition and is ready for re-use (the pressure inflation adjustment and releasable latch mechanism may also be turned back to its original starting position).

According to some embodiments, inflation-deflation devices may include a screw mechanism (e.g., knob 1373 and/or 1383) coupling a housing (e.g., housing 140 or housing 120) to a plunger (e.g., plunger 110) or syringe tube with the plunger disposed within the syringe tube (e.g., tube 112) to move the plunger along a length of the tube, where the screw mechanism is attached to one of the proximal housing, and the distal housing. Specifically, the distal housing may include a screw mechanism coupled to a syringe tube with a plunger disposed within the syringe tube to move the plunger along a length of the syringe tube. Similarly, Specifically, the proximal housing may include a screw mechanism coupled to a syringe tube with a plunger disposed within the syringe tube to move the plunger along a length of the syringe tube. In some cases both, the distal and proximal housings may include such a screw mechanism. For example, referring to FIG. 13, in some embodiments, knob 1372 on the distal housing (oblong housing 1371) may be used to adjust the position of the syringe tube via a screw mechanism; and knob 1383 and another screw mechanism in the proximal housing may be used to adjust the position of the plunger, so FIG. 13 achieves plunger positions similar to those discussed in reference to FIG. 12.

Furthermore, an example process for using system 1300 and/or device 1360, or a like system or device, is described by the following operations:

1. The integrated controlled volume inflation-deflation device 1310 or 1360 is filled with contrast solution such that no bubbles or air voids are present. This done by placing or attaching the end of the extension line 1050 in or onto a contrast solution source and pulling the device 1310 or 1360 into its deflation position to pull contrast solution into it. The device 1310 or 1360 may then be pointed up and transitioned (pushed together) to its inflation position to push the air out of the device 1310 syringe and extension line 1050. This may involve hitting the device 1310 or 1360 into your hand to dislodge bubbles, additional transitions of the deflation/inflation positions and the pulling in of more contrast solution. The device 1310 or 1360 is left in the inflation position.
2. The aspiration syringe 1320 (20 ml) is filled with about 3-4 ml of dilute contrast media and de-bubbled.
3. The aspiration syringe 1320 is wet connected to the catheter's balloon inflation lumen connection and used to directly two times aspirate the catheter and balloon 1048 prior to its insertion into the patient as per the standard balloon catheter aspiration practice.
4. The aspiration syringe 1320 is removed. The balloon inflation connection on the catheter is left filled with contrast solution when the aspiration syringe is removed.
5. The catheter 1040 is positioned in the patient's coronary artery or other vessel of interest and the balloon 1048 is positioned at the desired occlusion position.
6. The integrated controlled volume inflation-deflation device 1310 or 1360 is wet connected to the catheter 1040. If operation 7 is not to be immediately performed, the pressure inflation adjustment on the integrated controlled volume inflation-deflation device 1310 or 1360 is unlocked/unlatched/rotated such that balloon deflation is assured (e.g., a small negative pressure) and re-locked/left releasably latched.
7. The pressure inflation adjustment on the integrated controlled volume inflation-deflation device 1310 or 1360 is unlocked/unlatched/rotated and the catheter's balloon 1048 is initially inflated to the pre-determined low pressure (e.g., 0.5 ATM).
8. The pressure inflation adjustment on the integrated controlled volume inflation-deflation device 1310 or 1360 is locked/left in a releasably latched state. (Note: It is assumed that the pressure gauge is a suitably low-compliance type, otherwise there could need to be operations to cut the pressure gauge out of fluid communication with the inflation lumen and, in some embodiments, to unlock the incremental inflation knob.)
9. If applicable, the incremental inflation knob 1333 may be adjusted as per a chart (click or counter number to balloon 1048 OD chart) and previous vessel sizing (e.g. by fluoroscopy) to inflate the balloon 1048 to a safe OD.
10. The occlusion is tested, such as by contrast injections (e.g., via a guide catheter) or pressure readings (e.g., via a catheter 1040 lumen, a catheter 1040 infusion lumen).
11. If the desired occlusion is not attained, the inflation knob 1333 is incremented to increase the balloon 1048 OD.
12. Operations 10 and 11 are repeated until vessel occlusion is attained.
13. The integrated controlled volume inflation-deflation device 1310 or 1360 is pulled apart into its deflation position to remove the vessel occlusion and allow blood flow.
14. The integrated controlled volume inflation-deflation device 1310 or 1360 may then be transitioned between its inflation and deflation positions to occlude the vessel for the desired amount time(s) at the desired times as per the medical treatment or procedure protocol.
15. With the balloon deflated by the integrated controlled volume inflation-deflation device 1310 or 1360 in its deflation position, the catheter 1040 may be re-positioned in the vessel or removed from the vessel.
16. The incremental inflation knob 1333 is adjusted as per the click to OD chart to a safe initial balloon 1048 OD for the new vessel position or back to its initial position (e.g., zero).
17. The integrated controlled volume inflation-deflation device 1310 or 1360 is transitioned to its inflation position and the incremental inflation knob 1333 is adjusted as previously described in operations 10-12 to attain vessel occlusion.
18. The integrated controlled volume inflation-deflation device 1310 or 1360 is pulled apart into its deflation position to remove the vessel occlusion and allow blood flow.
19. The integrated controlled volume inflation-deflation device 1310 or 1360 may then be transitioned between its inflation and deflation positions to occlude the vessel for the desired amount time(s) at the desired times as per the medical treatment or procedure protocol.
20. Operations 15 thru 19 may be repeated, as necessary.
21. With the balloon 1048 deflated by the integrated controlled volume inflation-deflation device 1310 or 1360 in the deflation position, the integrated controlled volume inflation-deflation device 1310 or 1360 may be removed from the catheter 1040 and the catheter 1040 withdrawn from the patient.
22. If the integrated controlled volume inflation-deflation device 1310 or 1360 is to be re-used with a different catheter in the same patient, then the device must be returned to its initial (out of package) adjustment conditions and operations started again beginning with operation 1.

It is contemplated that operations in addition to those above may be performed when using system 1300 and/or device 1360, or a like system or device. Also, in some cases, fewer than all of the operations above may be performed when using system 1300 and/or device 1360, or a like system or device. Likewise, in some cases, the order of some of the operations above may be switched around when using system 1300 and/or device 1360, or a like system or device. Moreover, according to some embodiments, the operations above may include those described with respect to the processes of FIG. 11.

Moreover, according to some embodiments, a device similar to device 1310 or 1360 may be used to obtain the initial occlusion, as well as to inflate and deflate an occlusion balloon, where the balloon is initially inflated (e.g., to a nominal OD) using a pre-determined injection volume. The example process described above for using system 1300 and/or device 1360 may be applicable to integrated controlled volume inflation-deflation device embodiments with features described in reference to FIGS. 5, 6, 8 and 10 by replacing operations requiring leaving the controlled volume inflation-deflation device in the inflation position prior to an initial balloon inflation with leaving the device in an appropriate mid-latched position and replacing operations requiring a predetermined pressure with operations requiring a an initial balloon inflation with a predetermined volume, such as a selected volume to provide an initial inflation to a formed or desired diameter by transitioning the device from a mid-latched position to the inflation latched position.

FIG. 11 is a flow diagram of a process to occlude, treat, and perfuse a blood vessel. FIG. 11 may be a process that includes operations of the processes described above for using an inflation-deflation device, such as inflation-deflation device 100 or 200 or an inflation-deflation device including structure 400, 500, 700, 800, 900, 1010, 1310, 1410, system 1300, 1360, 1400, and/or otherwise as described herein. At block 1105, a cannula having a balloon attached at or adjacent its distal end (e.g., a cannula for advancing percutaneously through a blood vessel to a region of interest), and the balloon may be aspirated. Block 1105 may correspond to aspirating balloon 1048 and catheter 1040 as described above with respect to FIG. 10, such as using aspiration syringe 1020 and stopcock 1030. Also, block 1105 may correspond to an operation of the process described above for using system 1300, 1000, and/or 1400.

Next, at block 1110, the cannula and balloon are advanced to a region of interest in a blood vessel. Block 1110 may correspond to descriptions above with respect to advancing cannula 392, balloon 348, cannula 692, balloon 648, catheter 1040, and/or balloon 1048 to a region of interest. Also, block 1110 may correspond to an operation of the process described above for using system 1300, 1000, and/or 1400.

At block 1115, the balloon is inflated to its initial or beginning diameter with a controlled volume or a controlled low pressure, by advancing an inflation-deflation device's plunger relative to a syringe body (or vice versa). A controlled volume or a controlled low pressure may be described as a selected or known volume or pressure. Block 1115 may be applicable for setups using a non-integrated controlled volume inflation-deflation device, such as inflation-deflation device, such as inflation-deflation device 100 or 200 or an inflation-deflation device including structure 400, 1410, system 1400, and/or otherwise as described herein. For instance, a "non-integrated" device may require assistance of another device to inflate a balloon to an initial or beginning diameter and to inflate the balloon to an occlusion diameter to occlude a blood vessel. A "non-integrated" device may not be able to or may not be able to conveniently inflate a balloon to an initial or beginning diameter and to inflate the balloon to an occlusion diameter with a single plunger, but may instead require assistance from another device having another plunger, such as a conventional inflation-deflation device, another syringe, and the like. With respect to the process of FIG. 11, in a non-integrated inflation system, the inflation device in 1115 may be a different inflation-deflation device than the one used in 1125, 1130, 1140, and 1150. In an integrated inflation system, the inflation-deflation device may be the same in all steps and there is only one plunger in the device. One plunger (versus two or more in the device) can provide a key improvement over previous devices, such as with respect to controlling the volume (or pressure) of fluid used to inflate and/or deflate the balloon.

For example, block 1115 may correspond to adjusting the pressure or volume inside the balloon and cannula to an initial or beginning pressure or volume as described above with respect to FIGS. 1-4 and/or 14. Specifically, block 1115 may correspond to engaging recess 182 or 282 with lock 152 or lock 252, respectively, as described above for FIGS. 1-3. Also, block 1115 may correspond to engaging recess 482 with lock 152 as described above for FIG. 4. Also, block 1115 may correspond to adjusting the pressure inside the balloon and cannula to an initial or beginning pressure using a low pressure inflation device, as described above with respect to system 1400 of FIG. 14. Alternately, block 1115 may correspond to adjusting the volume inside the balloon to an initial or beginning volume using a low volume syringe, as also described above with respect to system 1400 of FIG. 14. For example, block 1115 may correspond to latch 150 being in position INFLAT as shown in FIG. 1A such as by pushing housing 140 and 120 together, such as by using human hands. Moreover, with the non-integrated controlled volume inflation-deflation device in the inflation latched position and as part of the inflation system 1400 as shown in FIG. 14, the occlusion balloon 1448 may be inflated to an initial diameter using a controlled low pressure or a controlled volume applied by another inflation device 1420.

Alternatively, block 1115 may be applicable for setups using an integrated controlled volume inflation-deflation device, such as an inflation-deflation device including structure 500, 700, 800, 900, 1010, system 1000, 1310, system 1300, 1360, and/or otherwise as described herein for an "integrated" device. For instance, and integrated device may only use a single plunger to inflate a balloon to an initial or beginning diameter and uses the same plunger to inflate the balloon to an occlusion diameter to occlude a blood vessel. Moreover, such an integrated device may also use the same plunger to deflate the balloon to a perfusion or balloon relocation diameter, and may use the same plunger to transition between the occlusion and perfusion diameters.

For example, block 1115 may correspond to adjusting the pressure or volume inside the balloon and cannula to an initial or beginning pressure or volume as described above with respect to FIGS. 5-10, 12 and/or 13. Specifically, block 1115 may correspond to adjusting the pressure inside the balloon and cannula to an initial or beginning pressure, as described above with respect to an inflation-deflation device including structure 700, 1310, system 1300, and/or 1360 of FIGS. 7, 12 and 13. Moreover, block 1115 may correspond to adjusting the volume inside the balloon and cannula to an initial or beginning volume by transitioning the device from a mid-latched position to an inflation latched position, as described above with respect to an inflation-deflation device including structure 500, 600, 800, 900, and/or 1010 of FIGS. 5, 6, 8, 9, and 10. For instance, block 1115 may correspond to lock 152 and/or lock 154 engaging recess 588, 864, or 992 while the volume inside syringe body 112 is in communication with the balloon inflation lumen and balloon and then being transitioned to engaging recess 582, 862, or 982, respectively, of FIGS. 5, 6, 8 and 9 as described above.

Additionally, according to some embodiments of either non-integrated or integrated controlled volume inflation-deflation devices, block 1115 may entail the incremental inflation of the balloon OD to a safe OD according to a chart relating the inflation increment to the expected maximum balloon OD either in place of an initial inflation with a controlled volume of fluid or in addition to an initial inflation with a controlled volume or pressure of fluid. Specifically, as described above in reference to FIG. 3, the knob 130 of non-integrated device 100 may be turned a predetermined number of increments to initially inflate the OD of balloon 348 to a safe OD (e.g. a balloon OD that a measurement of the ID of vessel 390 near region of interest 396 indicates is safe or a balloon OD that will not over-stretch the vessel 390). This may not be a preferred embodiment due to the large number of volume increments that would be required, as was described previously. Also, as described above in reference to FIG. 14, the knob of non-integrated device 1410 may be turned a predetermined number of increments, after the initial inflation of balloon 1448 by either a controlled pressure or volume using another inflation device 1420, to further increase the balloon OD to a safe OD. Also, as described above in reference to FIG. 10, the knob of integrated device 1010 may be turned a predetermined number of increments, after the initial inflation of balloon 1048 by transitioning device 1010 from an appropriate mid-latch position to the inflation latched position, to further increase the OD of balloon 1048 to a safe OD. Also, as described above in reference to FIG. 12, the knob of integrated device 1310 may be turned a predetermined number of increments, after the initial inflation of balloon 1048 by adjusting pressure inflation adjustment and lock mechanism 1315 of device 1310, to further increase the OD of balloon 1048 to a safe OD.

At block 1120 it is determined if the blood vessel is occluded. Block 1120 may include use of imaging or contrast agent, pressure measurement and/or other processes as described herein, or as known in the art.

If at block 1120 the blood vessel is not occluded, the process of FIG. 11 continues to block 1125. At block 1125, the diameter of the balloon is increased by injecting an additional controlled volume of fluid by advancing the controlled volume inflation-deflation device's plunger. Specifically, block 1125 may include injecting a selected or known volume of liquid or fluid (e.g., substantially excluding gas or air bubbles) within the cannula and balloon. Also, at block 1125, the plunger of the inflation-deflation device may be pushed to a location to cause the balloon to occlude the blood vessel at a region of interest. In some cases, block 1125 may correspond to operations of the process described above for using an inflation-deflation device, such as inflation-deflation device 100 or an inflation-deflation device including structure 200, 400, 500, 700, 800, 900, 1010, system 1000, 1310, 1410, system 1300, 1360, system 1400, and/or otherwise as described herein. For instance, block 1125 may include rotating knob 130, 1333, or 1383 in rotational directions. For example, block 1125 may include incrementally increasing the volume of fluid in the balloon with an incremental volume of fluid pushed into the balloon by a controlled volume inflation-deflation device as described herein. For instance, block 1125 may correspond to the description above with respect to occluding a blood vessel with balloon 348 of FIG. 3, and balloon 1048 of FIG. 10. Thus, block 1125 may include twisting knob 130 in rotational directions ROTS until inflation-deflation device 100 in FIG. 3 has pushed an occlusion volume of fluid into balloon 348 to cause balloon 348 to occlude a blood vessel. Thus, block 1125 may include rotating knob 130 to inflate balloon 348 to have an inflation or outer diameter that is at least equivalent to an inner diameter of blood vessel 390 at region of interest 396 to occlude fluid or blood from moving by or past balloon 348 in vessel 390 directions DIRS as shown in FIG. 3. Also, block 1125 may correspond to operations of the process described above for using system 1000, 1300, 1400, and/or device 1360. One or more volume increments of fluid may be injected. The injected volume increments of fluid may or may not be sufficient to occlude the vessel.

After block 1125 processing returns to block 1120. If at block 1120 the blood vessel is not occluded, the process of FIG. 11 returns to block 1125. If at block 1120 the blood vessel is occluded, the process of FIG. 11 continues to block 1130. At block 1130 the controlled volume inflation-deflation device is transitioned to the deflation latched position to withdraw the plunger and deflate the balloon and remove the occlusion (e.g., caused by the inflated balloon).

At block 1130, the plunger of the inflation-deflation device may be retracted to a location to allow perfusion of the region of interest with blood. Block 1130, may include unlocking the latch, such as by pulling the distal housing away from the proximal housing of an inflation-deflation device, such as using human hands, to cause a latch to become unlocked to be subsequently locked in a deflation latched position. Specifically, block 1130 may correspond to pulling distal housing 120 and proximal housing 140 apart to put latch 150 in position DEFLAT as described above with respect to transitioning from FIG. 1A to FIG. 2 such that blood may flow in directions DIRS through vessel 390 and by balloon 348 as shown in FIG. 3 (deflated balloon 348 not shown in FIG. 3). Block 1130 may also correspond to engaging recess 486, 586, 786, or 986 with lock 152 and lock 154 as described for FIGS. 4-7 and 9. Moreover, block 1130 may correspond to engaging pin recess 866 with lock 852 as described for FIG. 8. Also, block 1130 may correspond to an operation of the process described above for using system 1000, 1300, 1400, and/or device 1360.

Moreover, block 1130 may include transitioning the inflation-deflation device to a deflation latched position to withdraw the plunger and deflate the balloon and remove the occlusion for a selected period of time. In some cases, the balloon may be deflated to perfuse the blood vessel for a reasonable time to avoid damage to the tissue fed or drained by the vessel, such as by lack of oxygen (e.g., 1, 2, 3, 4, 5, 10, 20, any combination thereof of minutes, or any number of seconds). For instance, block 1130 may involve pulling the distal housing and the proximal housing of the inflation-deflation device apart, such as using human hands, to move plunger 110 towards the proximal end of the inflation-deflation device to withdraw a sufficient fluid from the occlusion balloon via the cannula or catheter's balloon inflation lumen into syringe tube 112 to allow perfusion of the blood vessel for a selected period of time. For example, the selected period of time may be a desired time to allow blood flow, nutrients, and oxygen thereof to the region of interest of the blood vessel between occlusion and/or treatment periods. The performance of blocks 1115, 1120 and 1125 may result in a reduced vessel blood flow for a sufficient amount of time that the tissues fed or drained by the vessel may require a more normal perfusion or it may be advantageous to perfuse the tissues for a period of time. Additionally, it is expected for ease of use reasons that the fluid/injectate to be infused will not be connected to the catheter/cannula during catheter/cannula placement and the subsequent adjustment of the balloon's diameter to obtain a safe occlusion. Thus, the time required to locate, prepare and connect the syringe or other device containing the injectate to a catheter or cannula would also add to the time of reduced blood flow and occlusion and provide a time where the user could be distracted for an additional period of time. Therefore, it is expected that one safe process is to deflate the balloon and allow blood flow in the vessel for a period of time after the occlusion is attained and/or during fluid/injectate preparation and connection to the catheter/cannula.

At block 1135 a treatment agent is connected to the cannula (or a catheter having a cannula for infusing treatment agent into a blood vessel). Block 1135 may include connecting, attaching, interfacing, or otherwise coupling a treatment or other agent infusion device or receptacle containing a treatment, an imaging agent, a therapy enhancing or other agent to cannula 392, 692, 1040 to infuse the treatment or other agent to a region of interest of a blood vessel or to tissues connected to or adjacent to a blood vessel, such as through hole 394 as shown in FIG. 3. Appropriate treatment agents include one or more drugs, synthetic matter, genes, plant cells, animal cells, human cells, stem cells, bone marrow cells, and the like. According to some embodiments, block 1135 may include connecting an imaging agent or contrast agent to the cannula. Appropriate imaging agents may include mixtures of contrast and saline and/or other agents as known in the art that allows the balloon to be imaged by an imaging such as fluoroscopy, MRI or ultrasound. According to some embodiments, block 1135 may include connecting a flush or other therapy enhancing agents into the vessel. Appropriate flush or therapy enhancing agents may include saline or other water based solutions to remove the blood from an energy path where the energy may be sonic, light, electrical or other forms of energy.

At block 1140 the inflation-deflation device is transitioned to the inflation latched position to advance the plunger and re-inflate the balloon to the occlusion diameter. Block 1140 may include occluding a blood vessel at a region of interest as described above for block 1125 and/or 1120. At block 1140, the latch of the inflation-deflation device may be relocked to relocate the plunger at the occlusion location. Block 1140 may correspond to transitioning inflation-deflation device 100 from latch 150 being in position DEFLAT as shown in FIG. 2 to being in position INFLAT as shown in FIG. 3, to push a sufficient volume of fluid into balloon 348 to occlude blood vessel 390 at region of interest 396. Moreover, block 1140 may correspond to pushing the distal housing and the proximal housing of an inflation-deflation device together, such as using human hands, to transition a releasable latch from a deflation latched position, to an inflation latched position. Specifically, block 1140 may correspond to pushing a distal and proximal housing of an inflation-deflation device together to cause locks 152 and 154 to transition from recess 486 to recess 482, from recess 586 to recess 582, from recess 786 to recess 782, or from recess 986 to recess 982 as described for FIGS. 4-7 and 9. Similarly, block 1140 may correspond to pushing the housings together to cause lock 852 to transition from pin recess 866 to pin recess 862 as described for FIG. 8. It is contemplated that block 1140 includes relocking the latch to the inflation latched position as shown in FIG. 3, such as in the case where knob 130 has already been rotated to cause plunger 110 to push a sufficient or occlusion volume of fluid to inflate the balloon to occlude the blood vessel so that when the latch is relocked into the inflation latched position, the balloon is reinflated to the occlusion volume/occlusion OD and occludes the blood vessel. Also, block 1140 may correspond to an operation of the process described above for using system 1000, 1300, 1400, and/or device 1360.

Moreover, block 1140 may include holding the inflation volume of fluid in the balloon (e.g., balloon 1048 or 348) for a period of time, such as to occlude blood vessel (e.g., vessel 390) for a selected period of time before, during and/or after treatment or injection with a treatment or other agent as described above with respect to FIG. 3 and/or below for block 1145.

For example, at block 1145 a treatment or other agent is infused to a region of interest of a blood vessel. Block 1145 may include infusing one or more treatment agents, flushes and/or imaging agents as described above with respect to block 1040 and block 1135. Block 1145 may include infusing a treatment agent, flush and/or imaging agent to a region of interest of a blood vessel, such as through hole 394 as shown in FIG. 3, as otherwise described herein, and/or as known in the art via a catheter or cannula. Such a catheter or cannula may also include the occlusion balloon. Such a catheter or cannula may include other features, components and constructions known to the art. The treatment agent may be introduced proximal and/or distal to the occlusion.

Thus, blocks 1140 and 1145 may include locking or holding the plunger at location L3 to keep balloon 348 occluding vessel 390 as shown in FIG. 3, during treatment, such as for a selected period of time. Appropriate treatment time periods include those where the blood vessel is occluded for a reasonable time to avoid damage to the desired target tissue (such as by occlusion nor treatment for 10, 20, 30, 40, 100, 200, 300, 400 any combination thereof of seconds, or any number of seconds therebetween). It is contemplated that block 1140 may include treatment of the blood vessel, surrounding tissue, tissues fed or drained by the vessel and vessels attached to the blood vessel with one or more various treatment agents, flushes, drugs, synthetic matter, genes, plant cells, animal cells, human cells, stem cells, bone marrow cells, and other solutions as previously described.

At block 1150 the inflation-deflation device is transitioned to the deflation latched position to withdraw the plunger and deflate the balloon and remove the occlusion (e.g., caused by the inflated balloon). Block 1150, may correspond to and/or include descriptions above for block 1130.

Block 1155 is a decision block at which it is decided whether or not to continue treatment. If at block 1155 it is determined that treatment will not continue, the process continues to block 1160 where treatment is ended. Alternatively, if at block 1155 it is determined that treatment will continue, the process returns to block 1140. In some cases continuing treatment corresponds to operations of the process described above for using system 1000, 1300, 1400, and/or device 1360.

Also, according to embodiments, various modifications to the process described above for FIG. 11 may be made. For instance, the position of blocks 1105 and 1110 may be reversed. Also, in some cases, the position of block 1135 may be moved to any point in the process prior to block 1145. Next, block 1130 may be excluded from the process shown in FIG. 11 (e.g., no perfusion until after the region of interest is treated at block 1145). For example, after the region of interest is occluded at block 1120, processing may continue to block 1145 (e.g., the latch may be held locked in the inflation latched position so that treatment agent may be infused to the region of interest at block 1145). The process may then continue as shown and described above with respect to FIG. 11.

In other words, block 1130 can be eliminated, but is preferred to allow the tissue being fed by the vessel to recover (e.g., from lack of oxygen as noted for block 1130) before treatment/infusion from the reduced blood flow that occurred during 1115, 1120 and 1125. Thus, where occlusion is quickly reached at blocks 1115-1120 (possibly including block 1125), blocks 1130 and 1140 can be skipped to reduce the time required to perform treatment using an inflation-deflation device (e.g., according to FIG. 11). This may be benefit certain patients, where a shorter procedure leads to less risk due to anesthesia or other considerations.

In another example, block 1140 may occur during or after 1145. In such a case, all or a portion to the treatment or other agent may be infused into the vessel region of interest prior to the occlusion balloon being inflated to occlude the vessel. Such a modification to the process of FIG. 11 may have benefits in some treatments where the occlusion is remote from the tissues to be treated. For instance, blood flow may carry the treatment or other agent to the desired location and then the occlusion causes the flow to stop with the agent at the desired location.

Furthermore, in some embodiments, after block 1155, the cannula and balloon may be moved to a different location in the blood vessel, or in another vessel within the same person or patient and used to occlude another region of interest there. Specifically, another vessel position within a blood vessel may be occluded by moving the cannula and balloon after block 1155 to a different place, position, location, or region of interest within the vessel without disconnecting the inflation-deflation device or system. Then, the balloon may be re-inflated to occlude the vessel at the new place or location (e.g., continue at block 1115). In some cases, prior to re-inflating the balloon at block 1125, the knob (and pressure adjustment in some embodiments) of the inflation-deflation device may be turned in a direction to retract the plunger towards the proximal end of the inflation-deflation device, back to their initial position or a position appropriate to the vessel ID at the new location. The process of FIG. 11 may then return to block 1115, where the inflation-deflation device is returned to its inflation latched position and volume increments may be applied according to a chart, as previously described, and continue from block 1115 to treat a vessel at a new position or location. Alternately, the inflation-deflation device(s) or system may be disconnected from the catheter/cannula during the re-positioning in elastic balloon embodiments or embodiments that initially inflate the balloon using a controlled volume of fluid, provided sufficient attention is paid to return the inflation-deflation device(s) or systems to their initial conditions and to avoid introducing air into the components communicating with the occlusion balloon. Compliant balloons may change their nominal or formed OD during an initial use, such that reconnecting them to a inflation-deflation device(s) or systems that initially inflate the balloon to an low pressure may cause the balloon to inflate to a greater OD than expected. With a greater than expected initial OD, any subsequent incremental inflation according to a chart in block 1115, as previously described, may provide a balloon OD in excess of a safe OD. Therefore, such a disconnection may not be safe for compliant balloon systems.

The following descriptions provide basic structures and options related to the inflation-deflation devices, features, and/or components thereof described herein. For instance, according to some embodiments:

1. There may be only one syringe tube and only one plunger. The syringe tube may be attached either directly or indirectly to the distal housing. The plunger may be attached either directly or indirectly to the proximal housing.
2. There may be cowling-housing features (between the cowling and the proximal/distal housing that the cowling is not attached to) and/or retaining pin-housing features that operate such that:
   a. in the first (inflation) latched position, they hold and constrain the distal and proximal housings in a position with enough force to prevent their movement relative to each other in response to normal handling forces and the force resulting from the pressure created inside the syringe caused by the balloon inflation pressure, and such that there is enough volume left in the syringe to adjust the diameter of the inflated balloon from its initial diameter to cover the designed range of balloon outer diameters and, in some specific designs, to inflate the balloon to its initial diameter.
   b. in the second (deflation) latched position, they hold and constrain the distal and proximal housings further apart relative to the first latched position, such that the plunger may be moved enough relative to the syringe tube to deflate the balloon, but not enough to disengage the plunger from the syringe tube and with enough force that it will remain in the second latched position (the balloon will remain deflated) when subjected to normal handling forces. This second latched position doesn't have the critical "no movement allowed" constraint that the first latched position has.
   c. rotation may be prevented between any two or three of the distal housing, the proximal housing and the cowling, as required or desired for the particular chosen configuration of the inflation-deflation device. Constraining rotation makes it less critical which part of the device the user is holding on to with one hand when he rotates a knob or cowling with the other.
   The features include a releasable lock(s) or latch(es) and a mechanical interference(s).
   The retaining pin(s), if any, may be constrained between any two of the distal housing, the proximal housing or the cowling. At least one of the constraints may allow the desired longitudinal motion between the connected portions during transitioning between the second position and the first position.
   The cowling may have the safety function of covering any pinch points to prevent pinching during a transition from the second latched position to the first latched position.
3. There may be three ways to move the plunger relative to syringe body in a relatively continuous manner:
   a. A screw mechanism coupling between the cowling and the housing that it is attached to.
   The cowling may be rotated relative to the housing that it is attached to.
   b. A screw mechanism coupling between the syringe tube and the distal housing. A knob rotation may operate the screw mechanism.
   c. A screw mechanism coupling between the plunger and the proximal housing. A knob rotation may operate the screw mechanism.
   Any of these three ways may be provided with a counter or other rotation indicator.
   Any of these three ways may be provided with a releasable lock mechanism to prevent accidental adjustment. The releasable lock configuration may be designed to provide an incremental latching mechanism such that equal increments of fluid may be forced out into the balloon.
   It may be preferred that any one of these three ways may provide one of two functions:
   a. Conveniently inflate the balloon(s) to its initial outer diameter. This could be to a specific controlled volume (s) of fluid as shown on an indicator or counter or, if a pressure gauge is included, then the inflation could be to a specific controlled pressure(s) as well as a controlled volume. Of course, any two ways could also be utilized to create a device that has one control for a controlled pressure initial inflation(s) and another control for a controlled volume initial inflation(s)

b. Increment the outer diameter of the balloon(s) using incrementally equal controlled volumes of fluid. The current inflation increment may be shown on an indicator or counter.

In some cases, only one way alone may do both, but for the ease of use problems discussed herein, separate functions may be preferred. If only function "b" is incorporated, then the device is a non-integrated controlled volume inflation-deflation device. If both functions "a" and "b" are incorporated, then the device is an integrated controlled volume inflation-deflation device.

4. The function of conveniently inflating the balloon to its initial outer diameter using a specific controlled volume of fluid may also be provided by the mechanism described in 1 and 2 above; where a mid-latched position is provided. Transitioning the device from the mid-latched position to the first (inflation) latched position pushes a controlled volume of fluid into the cannula/balloon. There may be several mid-latched positions provided. Two options of providing multiple mid-latched positions for inflating balloons with different initial inflation volumes or to different initial outer diameters are described herein. A mid-latched position may be positive, that is it should not be loose or wobbly or there will be uncertainty in the amount of fluid to be injected into the cannula/balloon and thus, additional uncertainty in the initial outer diameter of the balloon (a safety issue). For instance, the ball may engage the OD of the recess hole or both sides of the groove.

5. Any inflation-deflation device may be provided with the described low compliance extension tube/tube-connector assembly attached to its syringe tube (e.g., see line 1050 of FIG. 10).

Although the paragraphs above are numbered and lettered, the numbering and lettering does not, necessarily, indicate an order of preference. As noted, embodiments can include a knob coupled to the screw mechanism having at least one indexing lock to engage at least one recess in a surface of the proximal housing adjacent the knob, such that rotating the knob causes the at least one indexing lock to engage the at least one recess and to move the plunger to a plurality of locations along the length. In such cases, it is considered that to operate the knob in an incremental manner, all that may be required is one (1) indexing lock and one (1) recess. In this instance, it takes one revolution of the knob to inject/withdraw one incremental volume of fluid into/from the balloon (move the plunger an incremental length within the syringe tube). More than one volume increment per knob rotation may be preferred, as this reduces the amount of knob turning the user is required to do during a procedure and it is difficult or impossible for a user to turn a knob 360 degrees to the next releasably latched position without releasing the knob and turning it some more. Thus having more than volume increment per knob rotation improves device ease of use. It will also work in the instance that there are one or more indexing lock(s) in combination with one or more recess(es). For instance, in the case of one indexing lock and three (3) recesses, there would be three (3) incremental inflation volumes per rotation of the knob. In another instance, in the case of four (4) indexing locks and one (1) recess, there would be four (4) incremental volumes per rotation of the knob. In the previous instances, one could also design the location(s) of the indexing lock(s) and/or recess(es) such that the incremental volumes are equal. Equal incremental volumes may be preferred, because they can be the simplest design, the safest (limit vessel over-stretch), and/or the easiest to use (limit amount of knob turning). In another instance, in the case of two (2) indexing locks and three (3) recesses, all equally spaced around the knob shaft, there would be six (6) equal volume increments per knob rotation. In any of these instances the forces applied by the indexing lock(s) to the knob may not be balanced, and thus a bending moment will be applied to the knob shaft that can interfere with the smooth turning of the knob, the counter mechanism, or the screw mechanism (which moves the plunger). However, one could design around these problems and make a device that operated acceptably.

Preferred embodiments include two (2) or more similar indexing locks and two (2) or more similar recesses, arranged such that all the indexing locks engage and disengage a recess simultaneously (or nearly simultaneously) during knob rotation and the indexing locks and recesses are arranged at equal distances from the knob shaft center and at equal angular intervals around the shaft. Thus, there may always be at least two (2) increments per knob rotation, the angular rotation of each increment is equal (each volume increment or length of plunger motion per increment is equal), either the ratio of indexing locks to recesses or the ratio of recesses to indexing locks is a whole number (1, 2, 3 . . . ) and the forces applied to the knob are balanced in a manner that minimizes any resultant bending moment applied to the knob shaft. These embodiments include the simplest designs and constructions that provide multiple (or a desired number of) volume increments per knob rotation, equal volume increments and minimize the bending moment applied to the knob shaft. For instance, in a preferred embodiment that comprises two (2) indexing locks and four (4) recesses; there would be four (4) equal incremental volumes per rotation of the knob. Referring to FIGS. 1C and 1D, a preferred embodiment comprised of three (3) indexing locks and three (3) recesses is shown and thus there are three (3) equal incremental volumes per rotation of the knob. Of course, more complex designs of multiple index locks and recesses can be designed that provide these attributes. It is also considered that the positions of the recess(es) and the indexing lock(s) may be exchanged Balloon 348, balloon 648, balloon 1048, balloon 1448, a balloon for occluding and perfusing a blood vessel as described in FIGS. 3, 6, 10, 12, and 14 may have properties, functionality, operate, and/or have an outer diameter that expands in response to incremental equal volumes of inflation fluid. For example, those balloons may function similarly to balloon 1548 as described below with respect to FIGS. 15-18.

Figure 15:
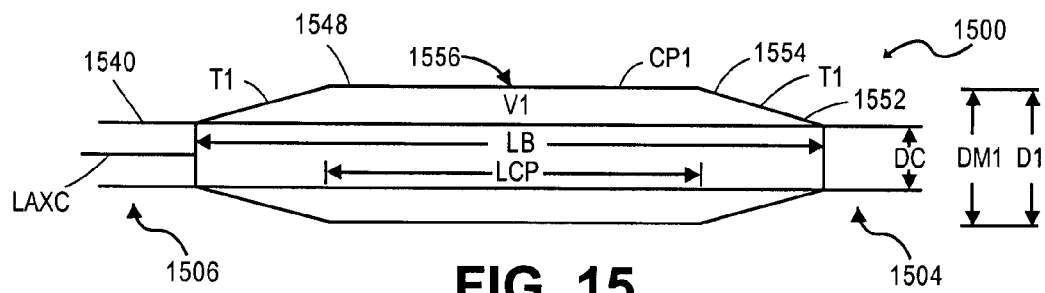
FIG. 15 is a cross-sectional side view of an occlusion balloon attached to a catheter inflated by a minimal volume of fluid (deflated).

FIG. 15 is a cross-sectional side view of an occlusion balloon attached to a catheter inflated by a minimal volume of fluid (deflated). FIG. 15 shows apparatus 1500 including cannula 1540 having a dimension suitable for percutaneous advancement through a blood vessel, such as to a region of interest to treat the region of interest with a treatment agent infused from cannula 1540 or another cannula. Cannula 1540 has diameter DC, longitudinal axis LAXC, proximal end 1506 and distal end 1504. Balloon 1548 is axially attached to the exterior surface of cannula 1540 at or adjacent distal end 1504.

Moreover, balloon 1548 may be described as having a cross-sectional profile or a contour that includes tapered (conical) ends extending proximally and distally to a cannula to which they are attached and includes a center portion between the tapered ends that defines a cylindrical shape. In some cases, balloon 1548 may be, an occlusion device or balloon that has a nominal or formed diameter that requires an initial volume of fluid to be injected into the balloon to inflate it such that the folds of the balloon are removed and/or it assumes an initial shape or OD, and has an outer diameter that increases by relatively (compared to other balloon shapes) equal increments in diameter increase in response to being inflated by equal increments in volume over a range of diameters. For example, balloon 1548 may have a cross-sectional profile or a contour that includes tapered (conical) ends extending proximally and distally to a cannula to which they are attached and includes a center portion between the tapered ends that defines a cylindrical shape. In some cases, as opposed to balloon 1548, other more curved balloon shapes (i.e. elliptical, spherical) may have a more rapid decrease in their diameter increase increment per inflation volume increment as their diameter increases. For balloon 1548, having relatively equal or more equal increments in diameter increase in response to being inflated by equal increments in volume over a range of diameters is desirable because this also minimizes the number of required inflation increments. Also, in some cases balloon 1548 may have a nominal or formed OD, such as an OD greater than the OD of the catheter shaft the balloon is attached or mounted on, when deflated, and that the balloon must be folded around the catheter shaft to produce the minimum catheter profile to facilitate catheter insertion/positioning in the vasculature (e.g., into a blood vessel).

FIG. 15 also shows balloon 1548 having inflation volume V1 and total length LB. In addition, balloon 1548 includes tapered ends T1 and center portion CP1. Center portion CP1 extends for length LCP of total length LB. Balloon 1548 has outer diameter DM1, which may be defined as the diameter at a location of balloon 1548 where tapered ends T1 meet center portion CP1. Balloon 1548 has diameter D1, such as a maximum diameter along center portion when inflated with volume V1. Balloon 1548 may be inflated and deflated, such as by being in communication with a lumen or tube (e.g., communication by the lumen or tube having an opening in the inner chamber or inside of balloon 1548) extending through cannula 1540 and to an inflation device such as a device for inflating balloon 1548 with gas (e.g., air) and/or liquid (e.g., fluid such as saline solution, contrast solution, water, and the like). Balloon 1548 may be inflated and deflated, by an inflation-deflation device such as inflation-deflation device 100, 200 or an inflation-deflation device including structure 400, 500, 700, 800, 900, 1010, 1310, 1410; and/or according to a process described above for FIG. 11 as described herein.

In some embodiments, cannula 1540 may have an outer diameter DC of between 1 and 7 mm, such as by having an outer diameter of 1 mm, 2 mm, 2.5 mm, 3 mm, 3.5 mm, 4 mm, 4.5 mm, 5 mm, 6 mm, or 7 mm. Moreover, cannula 1540 may be guidewire compatible such as compatible to be guided by a guidewire having an outer diameter of approximately 0.014 inches, 0.018 inches, 0.025 inches or other guidewire OD appropriate for the cannula OD, in a "over-the-wire" configuration where the catheter is guided over the guidewire, such as by having the guidewire disposed within a lumen of cannula 1540 and pushing cannula 1540 along the guidewire to the region of interest. Alternatively, cannula 1540 may be guided by a guidewire using a "rapid exchange" configuration, such as where an access hole is cut through the surface of the cannula to a lumen within so that a guidewire can be fed through the hole and lumen and out the distal end of the cannula.

Moreover, cannula 1540 may be a catheter having a number of tubes, internal tubes, or lumens disposed within cannula 1540, such as by having tubes within cannula 1540 to inflate balloon 1548, to infuse a treatment agent to a region of interest of a blood vessel either proximal or distal to balloon 1548, and to accommodate a guidewire disposed therein for guiding as described above. In addition, cannula 1540 may be configured to mount or accommodate sensors or devices such as electrodes, electrical wires, pressure transducers, optical fibers, imaging cores, and the like, as is known in the art. In addition, a proximal end of cannula 1540 that is kept external to a patient during use may include a triple arm or extension tubes that allow Luer access to a balloon inflation lumen, a guidewire lumen, and an infusion lumen within the cannula.

In some embodiments, balloon 1548 and cannula 1540 may be used to occlude various regions of interest of one or more blood vessels, such as without withdrawing the cannula and balloon from the vasculature of a person as described for the process of FIG. 11. For instance, the position of cannula 1540 and balloon 1548 may be adjusted to place the balloon in various positions within one or more blood vessels of a person with or without disconnecting an inflation-deflation device from being coupled to cannula 1540, to inflate and deflate balloon 1548 to occlude and perfuse blood flow in a blood vessel at a region of interest as described for the process of FIG. 11.

Balloon 1548 may be designed to have certain "properties" prior to inflation, during inflation, while occluding a blood vessel, when inflated with a volume sufficient to occlude a blood vessel, during deflation, when inflated with a volume during perfusion of a blood vessel, or when inflated and deflated otherwise. Specifically, the design may consider or select specific materials, inflation volumes, lengths, diameters, material thickness, tapered ends, center portions, and the like, so that balloon 1548 will have one or more specific "properties," as described herein. For example, as shown in FIG. 15, balloon 1548 may represent a balloon that is uninflated, folded or that is inflated with volume V1 which may represent a minimal or zero pressure or volume (e.g., minimal volume V1) of fluid as described herein. In some cases, as shown in FIG. 15, balloon 1548 may be a balloon designed to occlude a blood vessel, such as an artery or vein, including those of the human heart. Specifically, as shown in FIG. 15, balloon 1548 may be ready for insertion with cannula 1540 and percutaneous advancement to a region of interest of a blood vessel where balloon 1548 will be inflated and deflated, at least once, to occlude and/or perfuse blood at the region of interest.

In addition, balloon 1548 may have the properties and/or functionality described above with respect to balloon 348, balloon 648, 1048 and/or balloon 1448 for occluding and perfusing a blood vessel, such as described above with respect to the processes of FIG. 11.

In coronary artery applications, balloon 1548 may have total length LB between 1 and 10 mm, such as by having length LB of 2 mm, 3 mm, 4 mm, 5 mm, 6 mm, 7 mm, 8 mm, or 9 mm. Consequently, balloon 1548 may have center portion length LCP of between 0.5 mm and 8 mm, such as by having length LCP of 1 mm, 2 mm, 3 mm, 4 mm, 5 mm, 6 mm, or 7 mm. Correspondingly, tapered ends T1 may be equal or unequal in length and may be defined by (a) a portion of the balloon thicker in material than center portion CP1, (b) a portion of the balloon having an outer diameter contour or shape distinctive from center portion CP1, and/or (c) a portion of the balloon defining a certain lower range of outer diameter than center portion CP1. Naturally, in other vessel applications, these sizes of the balloon may be increased or decreased to accommodate the vessel size range to be occluded.

In some cases, the distinction between center portion CP1 and tapered ends T1 may be defined by a geometric distinction or shape, such as a distinct curve in profile or cross-section where center portion CP1 meets tapered end T1. Tapered (conical) ends form a near linearly increasing outer diameter geometry between where the balloon attaches to cannula 1540 near distal end 1506 and proximal end 1504 and center portion CP1. Also, center portion CP1 may define a cylindrical outer diameter profile (e.g., looking down axis LAXC) that is approximately equal in outer diameter along center portion CP1 (e.g., along length of center portion LCP, such as shown in FIG. 15).

The thickness of the material of balloon 1548 may decrease along ends T1 with distance towards portion CP1 from where ends T1 join the surface of cannula 1540. Thus, the material may be thicker at location 1552 than at location 1554. Similarly, the thickness may decrease along portion CP1 with distance from ends T1 towards the center of portion CP1. Here, the material may be thicker at locations 1552 and 1554 than it is at location 1556. For example, the material of balloon 1548 may be thickest near location 1552, thinner at location 1554, and thinnest at location 1556.

Thus, for balloon 1548, it is possible to select a balloon material or materials; tapered ends T1 shape, length, material, and thickness of material; and center portion CP1 length, material, and thickness of material to define a "property" such that when inflated, balloon 1548 will expand in its maximum outer diameter size to equally increasing or nearly equally increasing outer diameters in response to being inflated with equal inflation volume increments, such as incrementally equal volumes of inflation fluid. Nearly equally increasing outer diameters may be increases in outer diameter by sized increments within 5 or 10 percent of each other in response to incrementally equal volumes of inflation fluid over a selected range of volumes. Also, equally increasing outer diameters may be described as relatively equally increasing outer diameters (e.g., increasing by a constant additional diameter with respect to each prior diameter) when inflated with a plurality of equally increasing inflation volumes. For some balloon shapes and constructions, the incremental increase in balloon OD in response to an incremental inflation volume decreases at a rapid rate with each additional incremental inflation volume. In occlusion balloon systems, especially those that conveniently occlude vessels over a wide range of ID's, this is undesirable because it increases the number of inflation volume increments required to cover the desired balloon OD range (vessel ID occlusion range) and still have the largest OD change be a safe increment (not over-stretch the vessel, as previously described).

For instance, tapered ends T1 may maintain a relatively linear and small increase in their length and during and over the range of inflation of the balloon. Center portion CP1 may define a relatively flat or constant outer diameter at lower inflation volumes of the balloon, but begins to increasingly bow so that the center of center portion CP1 increases in diameter greater than the rest of center portion CP1 at higher inflation volumes. Thus, while at low volumes or a low OD, a fixed additional inflation volume will increase the outer diameter by a specific amount because that fixed volume may increase the diameter across the entire center portion, length LCP. Alternatively, while at higher inflation volumes or larger OD, the same fixed additional inflation volume will increase the outer diameter by an almost equal specific amount since it must only fill the lower volume needed to increase the outer diameter near the center of the center portion and not the much greater volume that would be required to inflate the entire length to the increased diameter.

In one example, balloon 1548 may increase by outer diameter increments on the order of 0.25 mm or less for each increment of inflation volume of between 0.02 and 0.005 cubic centimeters (cc), or less. For example, balloon 1548 could increase by increments of 0.03 mm, 0.025 mm, 0.0225 mm, 0.02 mm, 0.0175 mm, 0.015 mm, or less in response to incremental increases in inflation volume of 0.02 cc, 0.0175 cc, 0.015 cc, 0.0125 cc, 0.01 cc, 0.0075 cc, 0.05 cc, 0.025 cc, or less.

In some cases, the balloon diameter increased with one inflation-deflation device incremental increase in equal volumes of inflation fluid by between 0.12 mm and 0.19 mm. In such an example, a safe over-stretch of the vessel (maximum safe vessel stretch beyond the stretch required to attain an occlusion) could be considered to be, at least, 0.19 mm. For example, an inflation-deflation device as described above or using a process as described above, may be used to inflate balloon 1548 with incremental equal increases in inflation volume to increase the outer diameter of balloon 1548 by equal incremental increases of one of 0.12, 0.13, 0.14, 0.15, 0.16, 0.17, 0.18, and 0.19 mm increments in response to each incremental equal increase in inflation volume. It is also contemplated that balloon 1548 may respond to the incremental equal increases in inflation volume by expanding to each increment with a decrease in outer diameter change between 0.19 mm and 0.12 mm in the range described above where each incremental increase in the outer diameter is not equal to every other incremental increase in the outer diameter. Thus, although incremental equal volumes on inflation fluid are being introduced into balloon 1548, the outer diameter may increase by one amount (e.g., such as 0.013 mm) in response to one incremental increase inflation volume, but increase in outer diameter by another amount (e.g., such as 0.012 mm) in response to the subsequent incremental equal volume of inflation fluid. However, the rate of this decrease (or increase) may be reduced by the design of the balloon as previously described.

Also, according to some embodiments, the cannula inside or along side the balloon may have a smaller OD than a proximal portion of the cannula and therefore, the OD of the catheter doesn't necessarily have to substantially increase the OD of the catheter in the region where the balloon is mounted. For instance, the lumen/tube portion that inflates the balloon can be terminated at the proximal end of the balloon and the OD/ID of a distal (to the balloon's proximal end) infusion and/or guidewire lumen/tubing can be reduced to make the cannula OD smaller along the length of the balloon. For example, although FIG. 15 shows diameter DM1 and diameter D1 greater than diameter DC, it is contemplated that balloon 1548 may be attached over a portion of cannula 1540 having an inner structure or tubing such that the exterior surface of cannula 1540 has a smaller OD under balloon 1548. In some cases, structure of or within cannula 1540 may exist under balloon 1548 such that the outer surface of cannula 1540 has a smaller OD for at least a portion of length LB. Thus, diameter DM1 and/or diameter D1 may be equal to or even slightly less than diameter DC prior to inflation, such as when balloon 1548 is at a zero or minimal inflation volume (e.g., deflated and/or folded).

The increases in diameter, volume, and/or pressure described above may occur over a range of volumes starting at V1, V2, or V3 and continuing over a range of volumes, such as to V4, as described below in FIGS. 16-18.

Figure 16:
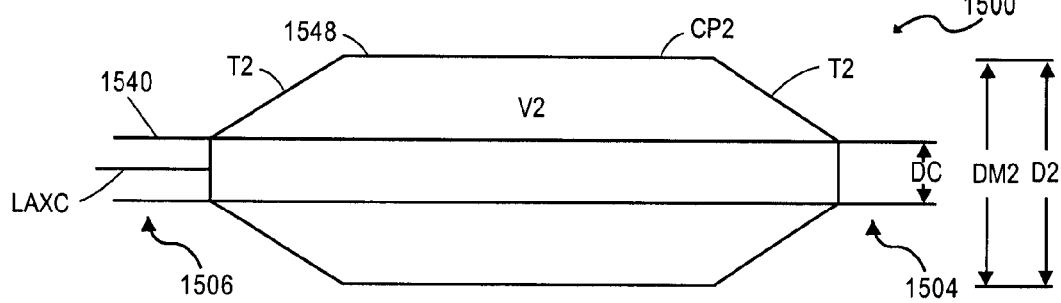
FIG. 16 is a schematic cross-sectional side view of the balloon of FIG. 15 inflated with a greater volume of fluid.

For example, FIG. 16 is a schematic cross-sectional side view of the balloon of FIG. 15 inflated with a greater volume of fluid, such as inflated to a low pressure and/or to a volume which corresponds to its formed or nominal OD. In FIG. 16, balloon 1548 is shown having center portion CP2 and tapered ends T2. For example, tapered ends T2 may define linear increases in outer diameter similar to those described above with respect to tapered ends T1 (e.g., extending away from the cannula surface over length LB at a greater rate than T1). Similarly, center portion CP2 may define a cylindrical outer diameter having a substantially equal outer diameter along the length of center portion CP2 as described above with respect to CP1. FIG. 16 shows balloon 1548 inflated to outer diameter D2 at center portion CP2, and diameter DM2 at the meeting of tapered ends T2 and center portion CP2. Thus, as shown in FIG. 16, center portion CP2 may define an approximately cylindrical shape extending along longitudinal axis LAXC between tapered ends T2. As noted above for tapered ends T1, tapered ends T2 may have a thicker thickness of balloon material than center portion CP2. Also, the material may be thicker near the point at which balloon 1548 attaches to cannula 1540 than portion CP2, and thicker at the point at which the tapered ends meet center portion CP2 (e.g., such as at diameter DM) than at the center of center portion CP2.

Diameter D2, may be reached, such as in response to being inflated with volume V2 (such as volume V1 plus an initial inflation volume of a liquid or as an initial inflation to an initial pressure as described herein) where volume V2 is greater than volume V1. It is contemplated that the difference between volume V2 and volume V1 may be a predetermined increase in inflation volume, such as a volume of between 0.04 and 0.25 cc for coronary artery applications. For example, as shown in FIG. 16, balloon 1548 may represent a balloon that is inflated with volume V2, which may represent a nominal pressure or volume (e.g., nominal volume V2) of fluid as described herein.

Balloon 1548 may have a property to accommodate and at least 1.5 mm increase in diameter from its nominal or formed diameter, such as diameter D2 as shown in FIG. 16. Thus, an embodiment of balloon 1548 (for instance a coronary artery embodiment) attached to cannula 1540, where cannula 1540 is a catheter having an outer diameter DC between 0.8 to 1.8 mm, and a nominal balloon diameter D2 for balloon 1548 may be 3.0 mm. In another instance (for instance a coronary artery embodiment), where cannula 1540 has the same outer diameter, balloon 1548 may have a nominal outer diameter D2 of 4.0 mm. For example, these embodiments may be for a coronary artery application and may use one of two 2 Pebax® balloons as a compliant occlusion balloon for a procedure. One balloon has a nominal/formed OD of 3.0 mm and the other has a nominal/formed OD of 4.0 mm. Both balloons are designed to be inflated 1.5 mm beyond their nominal OD without bursting. This gives one balloon a nominal range in OD of 3.0-4.5 mm and the other 4.0 mm to 5.5 mm. Both balloons are design to be mounted on the same cannula OD (e.g., outer diameter DC of cannula 1540). In some cases, that cannula OD is about 1.2 mm. Experimentation has found that a coronary artery requires about 0.5 mm overstretch (increase in ID over its apparent/measured ID by fluoroscopy) to create an effective occlusion. Thus, one balloon is designed to occlude coronary arteries with ID's of 2.5 to 4.0 mm and the other 3.5 to 5.0 mm. The overlap of the ranges by 0.5 mm is to allow for vessel ID measurement uncertainties, such that choosing the balloon covering the measured vessel ID most within its range will safely occlude a vessel in the 3.5 to 4.0 mm ID range that is incorrectly measured with an error of 0.5 mm. In actual fact, it is possible to initially inflate the balloons to a low pressure (0.5 ATM), so that neither balloon will damage (overstretch an unnecessary amount) an artery due to its initial inflation. For instance, the balloon may keep a fold in it as it is inflated (e.g., using the process of FIG. 11). Sometimes, the larger balloon may be chosen and may obtain a good safe occlusion either with the initial inflation or with very few subsequent incremental volume inflations. During a procedure, this may lead to time saving, which can be very important to reduce the length of the procedure. If the system uses a controlled volume for the initial inflation, then purposely choosing the over-sized balloon could result in vessel damage because the balloon would attain its nominal OD upon its initial inflation and thus force the vessel ID to that size. Because of this, a system/device that initially inflates the balloon to a controlled low pressure may be more forgiving and safe In one specific example, balloon 1548 may have a nominal diameter of D2 of 3.0 mm that may expand to have an inflated outer diameter of up to 3.75 mm before being permanently deformed. An alternative way of thinking of this is that balloon 1548 beginning with a nominal balloon diameter D2 of 3.0 mm may have an elastic recoil of about 0.75 mm and thus, if inflated up to 3.75 mm and deflated, it would return to its initial 3.00 mm diameter, however if inflated to 4.2 mm, it would only return to 3.45 mm. Similarly, for balloon 1548 having nominal diameter D2 of 4.0 mm, the balloon may have an elastic recoil of 1.0 mm such that when inflated to greater than 5.0 mm, the balloon will not return to its original 4.0 mm when deflated. Moreover, once the outer diameter of balloon 1548 is taken beyond a certain diameter, the "elastic limit diameter," the diameter of balloon 1548, may not return to the initial, minimal or nominal diameter D2 without folds in the balloon material. The behavior of compliant occlusion balloons can often be characterized in this manner.

Furthermore, in some embodiments, the initial controlled inflation pressure for balloon 1548 to inflate it to its nominal or formed OD may occur at between 0.2 atmospheres (ATM) and 2.0 ATM in pressure. For example, balloon 1548 may attain its nominal inflation volume VOL2 and OD D2 when inflated with 0.4 ATM, 0.5 ATM, 0.6 ATM, or 1.0 ATM in pressure by a device or system that performs the initial balloon inflation using a controlled low pressure. In some embodiments, where the device or system performs the initial balloon inflation using a controlled low pressure, the device may be manipulated to initially apply a larger pressure and then stabilize the pressure at a lower value. For instance, if the plunger relative to the syringe body is advanced at a rate that applies 1 ATM at the proximal end of the cannula/catheter during the initial filling of the balloon, the pressure in the balloon will be very low and there will be no danger of applying damaging pressures or balloon OD's to the vessel. Once the pressure in the balloon begins to rise, the rate of plunger advance relative to the syringe body required to keep the applied pressure a 1 ATM will be noticeably reduced. At that time, the rate of plunger advance relative to the syringe body can be even further reduced and adjusted to stabilize the applied pressure at 0.5 ATM. Thus, the pressure seen by the balloon may be limited to only 0.5 ATM with this technique. The advantage of this technique is that the time required to initially inflate the balloon to the desired controlled low pressure, in this example 0.5 ATM, is substantially reduced by the increased fluid flowrate produced by the higher pressure portion of the inflation procedure, in this example 1 ATM.

The increases in diameter, volume, and/or pressure described above may occur over a range of volumes starting at V1, V2, or V3 and continuing over ranges of volume, such as to V4, as described below in FIGS. 17-18.

Figure 17:
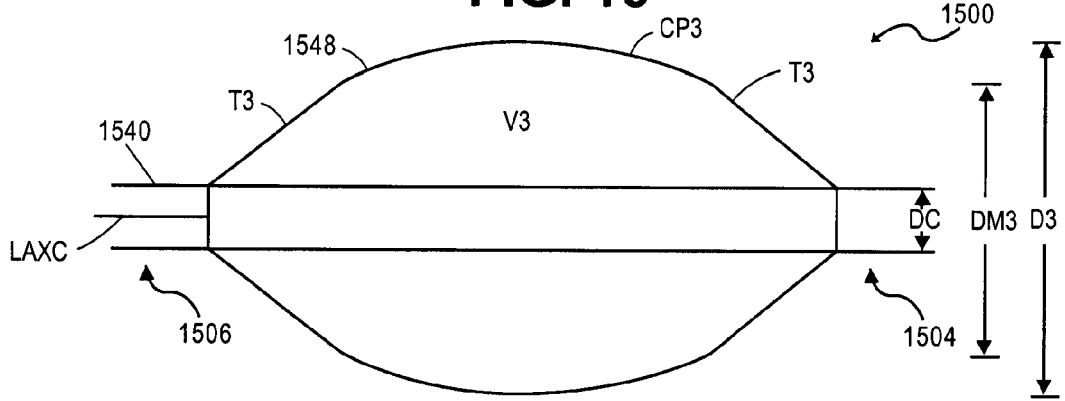
FIG. 17 is a schematic cross-sectional side view of the balloon of FIG. 16 inflated with a greater volume of fluid.
Figure 18:
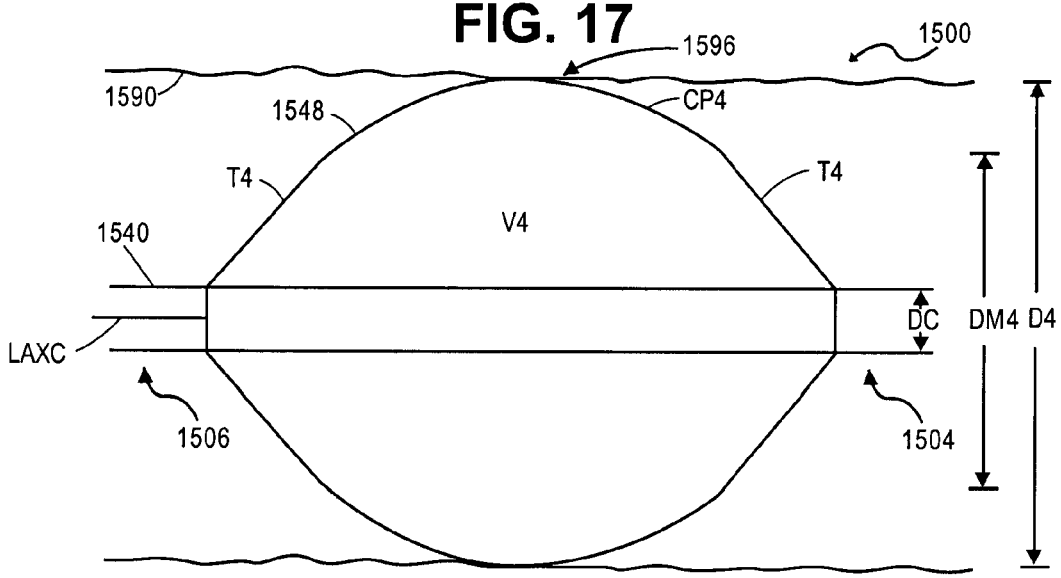
FIG. 18 is a cross-sectional side view of the balloon of FIG. 17 inflated with a greater volume of fluid and occluding a blood vessel at a region of interest.

FIG. 17 is a schematic cross-sectional side view of the balloon of FIG. 16 inflated with a greater volume of fluid. FIG. 17 shows balloon 1548 having outer diameter D3 when inflated with inflation volume V3. In FIG. 17, balloon 1548 is shown having outer diameter D3 and diameter DM3 where tapered ends T3 meet center portion CP3. Diameter DM3 is less than diameter D3.

The increase in volume from volume V2 to volume V3 may be one or more incremental equal increases in inflation volume as described herein. Thus, diameter D3 may be reached after one or more incremental equal or nearly equal increases in outer diameter of the balloon in response to the incremental equal increases in inflation volume.

Specifically, tapered ends T3 may define linear or curved increases in outer diameter greater than that of ends T2 with distance along length LB away from where balloon 1548 joins the surface cannula 1540. Also, center portion CP3 may define a more spherical or curved shape between tapered ends T3 with respect to a cross section along axis LAXC (e.g., as shown in FIG. 17) so that outer diameter D3 is greater than diameter DM. Specifically, center portion CP3 may bow into the curved shape because the thickness of the balloon material along portion CP3 is less than the thickness of the balloon material at tapered ends T3 and the lowest energy state of an inflating body is to inflate in an increasingly spherical manner. As a result of this curvature, the balloon volume changes as the balloon's occlusive OD (D2, D3, D4) is increased, becomes much more linear than that of other common occlusive balloon shapes, such as spherical balloons. Thus, this design (going from a straight cylinder with tapers shape to a more spherical shape in the balloon's designed OD range) a can be adapted to a controlled volume inflation-deflation device an efficient and safe manner. Balloon OD increments can be thus controlled in a narrower range (OD increment size is the Max. over-stretch of the vessel that may occur using a safe occlusion procedure, such as the method of FIG. 11). The closer balloon OD increments are to each other over the balloon OD range, the fewer injection volume increments are required.

Thus, balloon 1548 can be safely and conveniently inflated with incremental equal increases in inflation volume to occlude a blood vessel over a defined range of balloon OD's. For example, FIG. 18 is a cross-sectional side view of the balloon of FIG. 17 inflated with a greater volume of fluid and occluding a blood vessel at a region of interest. FIG. 18 shows balloon 1548 occluding blood vessel 1590 at region of interest 1596 and inflated with inflation volume V4. In FIG. 18, balloon 1548 is shown having outer diameter D4, such as a maximum outer diameter along center portion CP4 when the balloon is inflated with volume V4 or an outer diameter while the balloon occludes blood vessel 1590. The increase in volume from V3 to V4 may be one or more incremental equal increases in inflation volume as described herein (e.g., such as an increase as described above with respect to the difference between volume V2 and volume V3).

Balloon 1548 is shown having tapered ends T4, center portion CP4, and diameter DM4. As shown in FIG. 18, balloon 1548 defines diameter DM4 where tapered ends T4 meet center portion CP4. Diameter DM4 is less than diameter D4. Tapered ends T4 may define linear or curved increases in outer diameter greater than that of ends T3 with distance along length LB away from where balloon 1548 joins the surface of cannula 1540. Center portion CP4 may define spherical or curved shape with respect to axis LAXC similar to that described above with respect to center portion CP3, except center portion CP4 extends greater in outer diameter from diameter DM4, than diameter D3 extends from diameter DM3.

In some embodiments, diameter D4 is a diameter between 2 and 10 mm in diameter, such as a diameter of 2 mm, 3 mm, 3.5 mm, 4 mm, 4.5 mm, 5 mm, 5.5 mm, 6 mm, 7 mm, 8 mm, 9 mm, or 10 mm. Moreover, volume V4 may define a total volume, occlusion volume, or inflated volume for balloon 1548. Volume V4 may be a volume in the range of between 0.05 cc and 1.5 cc, such as a volume of 0.05, 0.1, 0.15, 0.2, 0.3, 0.4 0.5 cc, 0.6 cc, 0.7 cc, 0.8 cc, 0.9 cc, 1 cc, 1.1 cc, 1.2 cc, 1.3 cc, 1.4 cc, or 1.5 cc. For example, when V4 is approximately 0.12 cc of fluid, balloon 1548 may have outer diameter D4 of between 3.5 and 4.5 mm. Also, the difference between volume V4 and volume V2 may include one or more incremental equal volumes of inflation fluid, such as between 1 and 20 increments of fluid pushed into balloon 1548 by an inflation-deflation device (e.g., inflation-deflation device and/or structures described above with respect to FIGS. 1-10 and 12-14) and/or using processes described above with respect to FIG. 11 (e.g., such as described at blocks 1115, 1120 and 1125).

It is contemplated that balloon 1548 may be deflated to perfuse blood at a region of interest of a blood vessel. For example, after inflation to occlude the blood vessel as shown in FIG. 18, the volume of inflation fluid within balloon 1548 may be reduced to allow perfusion of blood within vessel 1590. Such deflation may include deflation as is described above with respect to balloon 348 and FIG. 3; and/or blocks 1130 or 1150 of FIG. 11. Moreover, after deflation, balloon 1548 may be reinflated to occlude a blood vessel, such as described above with respect to balloon 348 and FIG. 3; and/or block 1140 of FIG. 11. Thus, balloon 1548 may be inflated to occlude a blood vessel, deflated to allow perfusion, reinflated to occlude the blood vessel and left inflated while a treatment agent is infused into the blood vessel, and then deflated to allow perfusion. That process of inflation to occlude, infusion of a treatment agent to treat, and deflation to perfuse a blood vessel may be repeated as desired.

Specifically, design selection or "properties" of balloon 1548 may allow the balloon to revisit the shapes, contours, outer diameters, and volumes when being subsequently deflated, re-inflated, and/or re-deflated to occlude and/or perfuse blood flow in one or more regions of interest of one or more blood vessels. For example, balloon 1548 may or may not revisit the same outer diameter (e.g., diameter D2, D3, and/or D4) when inflated with the same volumes (e.g., volumes VOL2, VOL3, and/or VOL4) a second time, after being deflated. It may be appreciated that after initial inflation to occlude a blood vessel, when being deflated, or when being inflated and deflated for such a purpose, if balloon 1548 is a compliant balloon design (the balloon material is stretched beyond its elastic range at an inflated OD) may vary in shape, contour, outer diameter, and volume, especially if a smaller occlusive OD is attempted to be set in a smaller vessel after a larger occlusive OD has been attained in a larger vessel. Thus, in some balloon 1548 smaller vessels first to avoid the impact of balloon shape/OD changes at a low controlled initial inflation pressure in the event such a device or system is disconnected and then reconnected to the cannula/catheter of the balloon.

An important point about FIGS. 15-18 is that the tapered occlusion balloon design tends to even out the incremental OD increase of the balloon for equal increments of volume injected by a controlled volume inflation-deflation device into the balloon as the cylindrical portion of the balloon goes from a straight cylinder shape to a more spherical shape over a range of OD's. Thus, this design (going from a straight cylinder shape to a more spherical shape in the balloon's OD range) a can be adapted to a controlled volume inflation-deflation device in an efficient and safe manner. Balloon OD increments can be thus controlled in a narrower range (OD increment size is the Max. over-stretch of the vessel that may occur using a safe occlusion procedure). The closer balloon OD increments are to each other over the balloon OD range, the fewer volume injection increments are required. In this regard, the tapered occlusion balloon design may be much better than other common occlusion balloon designs, like spherical balloons. Another important point about tapered balloons is that they may lend themselves well to having balloons of different OD ranges be operated by the same inflation volume increment (same controlled volume inflation-deflation device) and still have very nearly equal (or substantially equal) balloon OD increments.

Figure 19:
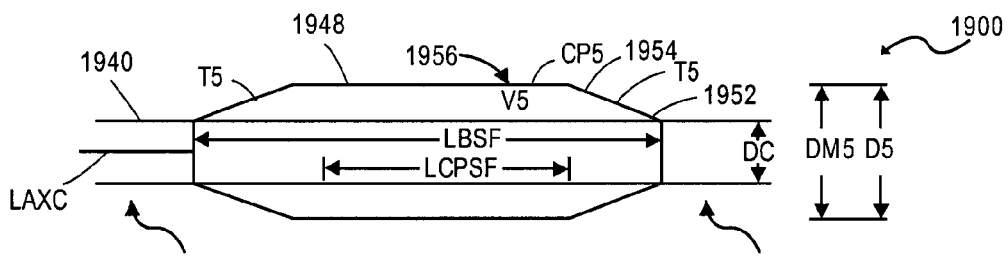
FIG. 19 is a cross-sectional side view of an occlusion balloon attached to a catheter inflated by a minimal volume of fluid (deflated).
Figure 20:
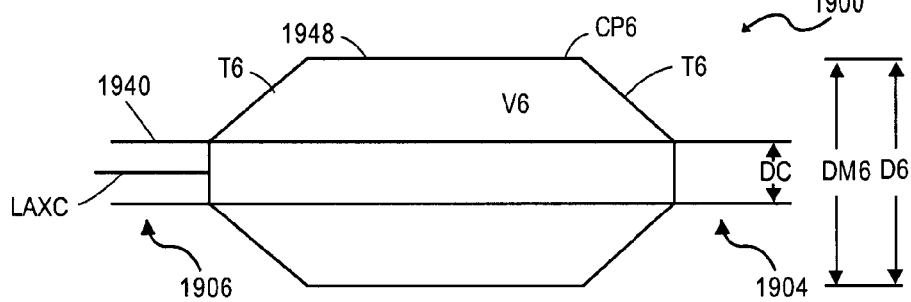
FIG. 20 is a schematic cross-sectional side view of the balloon of FIG. 19 inflated with a greater volume of fluid.
Figure 21:
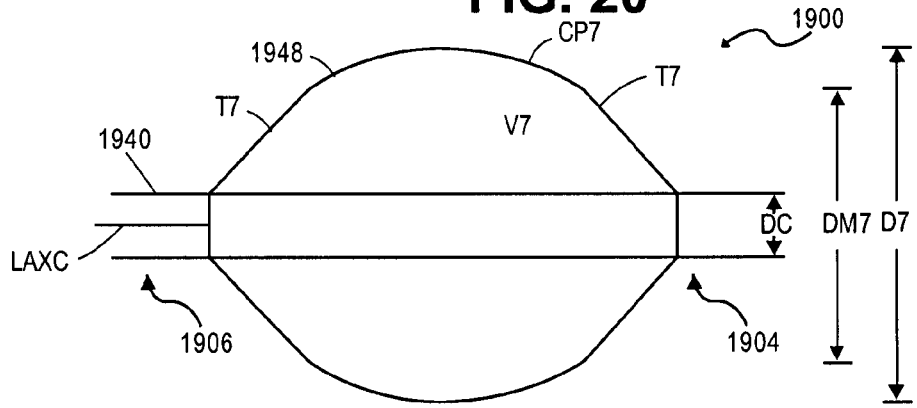
FIG. 21 is a schematic cross-sectional side view of the balloon of FIG. 20 inflated with a greater volume of fluid.
Figure 22:
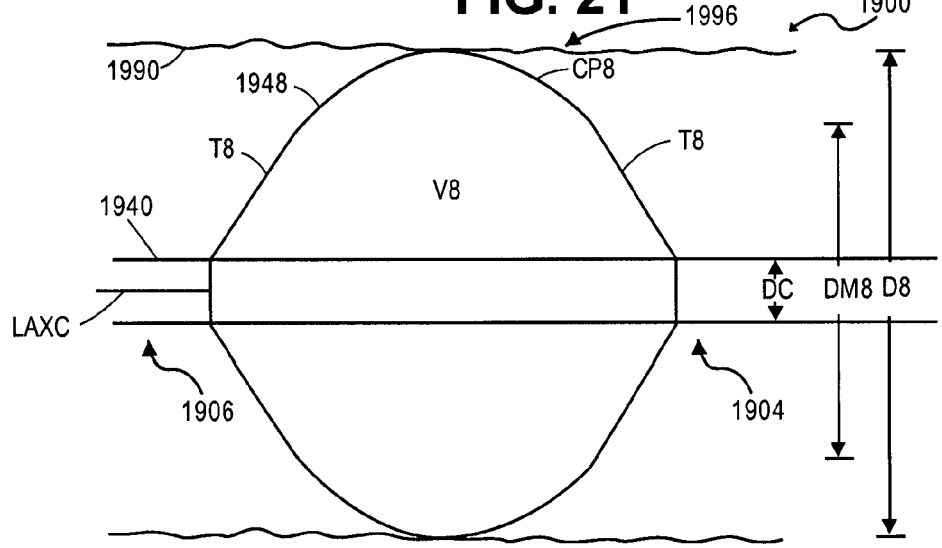
FIG. 22 is a cross-sectional side view of the balloon of FIG. 21 inflated with a greater volume of fluid and occluding a blood vessel at a region of interest.

As mentioned above for FIGS. 15-18 a tapered occlusion balloon design may lend to having balloons of different OD ranges be operated by the same inflation volume increment (same controlled volume inflation-deflation device) and still have very nearly equal balloon OD increments. For example, this may allow use of the same controlled inflation-deflation device to operate 2 different balloon designs, one with a formed/nominal OD of 3.0 mm and one with a formed/nominal OD of 4.0 mm and thus, safely, efficiently and conveniently occlude a wider range of vessel ID's. For example, FIGS. 19-22 are a cross-sectional side view of an occlusion balloon attached to a catheter inflated by a volume of fluid. Specifically, FIG. 19 is a cross-sectional side view of an occlusion balloon attached to a catheter inflated by a minimal volume of fluid (deflated). FIG. 20 is a schematic cross-sectional side view of the balloon of FIG. 19 inflated with a greater volume of fluid; FIG. 21 is a schematic cross-sectional side view of the balloon of FIG. 20 inflated with a greater volume of fluid; and FIG. 22 is a cross-sectional side view of the balloon of FIG. 21 inflated with a greater volume of fluid and occluding a blood vessel at a region of interest.

FIG. 19 shows apparatus 1900 including cannula 1940 having a dimension suitable for percutaneous advancement through a blood vessel, such as to a region of interest to treat the region of interest with a treatment agent infused from cannula 1940 or another cannula. Cannula 1940 has diameter DC, longitudinal axis LAXC, proximal end 1906 and distal end 1904. Balloon 1948 is axially attached to the exterior surface of cannula 1940 at or adjacent distal end 1904. FIG. 19 also shows balloon 1948 having inflation volume V5 and total length LBSF. In addition, balloon 1948 includes tapered ends T5 and center portion CP5. Center portion CP5 extends for length LCPSF of total length LBSF. Balloon 1948 has outer diameter DM5, which may be defined as the diameter at a location of balloon 1948 where tapered ends T5 meet center portion CP5. Balloon 1948 has diameter D5, such as a maximum diameter along center portion CP5 when inflated with volume V5.

Apparatus 1900, parts, features, functions, dimensions, design, and/or manufacture thereof may be similar to those corresponding for apparatus 1500, except that length LCPSF is shorter than length LCP (and thus, length LBSF is shorter than length LB). Also, D6 (the formed, beginning or nominal OD) is larger than D2, D7 is larger than D3, and D8 is larger than D4. In some cases, D1 can equal D5. Moreover, volume V5, V6, V7, and V8 may or may not equal V1, V2, V3, and/or V4 respectively. Moreover, although the above mentioned features of balloon 1948 may be different than those of balloon 1548, cannula 1940 may be a cannula similar to cannula 1540.

According to some embodiments, both balloon 1548 and 1948 can be designed to have nearly the same OD increase in response to the same incremental inflation volume. For instance, referring to FIGS. 15-22, V3-V2 may equal or nearly equal V7-V6, V4-V3 may equal or nearly equal V8-V7 and V4-V2 may equal or nearly equal V8-V6; D3-D2 may equal or nearly equal D7-D6, and/or D4-D3 may equal or nearly equal D8-D7 and/or D4-D2 may equal or nearly D8-D6. This effect is accomplished by shortening of the balloon length of the larger OD balloon, as discussed above.

Figure 23:
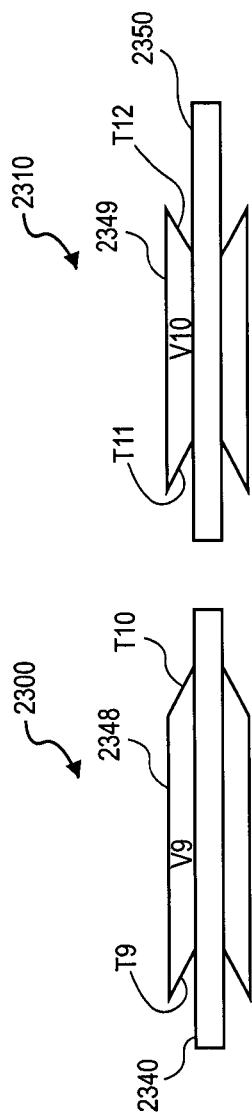
FIG. 23 is cross-sectional side views of occlusion balloons attached to a catheter inflated by a volume of fluid.

Also, according to embodiments, either or both balloon 1548 and 1948 can be designed to have one or both tapered ends (e.g., ends T1, T6, and the like) configured and/or attached to the cannula (e.g., cannula 1540 or 1940) such that the attachment point of the balloon to the cannula is toward the center of the balloon and not away from the center of the balloon as is shown in FIGS. 15-22. For example, FIG. 23 is cross-sectional side views of occlusion balloons attached to catheters and inflated by a volume of fluid. FIG. 23 shows apparatus 2300 including balloon 2348 having tapered ends T9 and T10 configured and/or attached to cannula 2340, and inflated by volume of fluid V9. Apparatus 2300, parts, features, functions, dimensions, design, and/or manufacture thereof may be similar to those corresponding for apparatus 1500 or 1900, above, other than the orientation of tapered end T9. Thus, cannula 2340 may be similar to cannula 1540 or 1940, end T10 may be similar to end T1 or T5, and volume V9 may be similar to volume V1 or V6. Also, balloon 2348 may function similarly to balloon 1548 and/or 1948 as described above, other than the orientation of tapered end T9. Specifically, end T9 may be configured and/or attached to cannula 2340 such that the attachment point of the balloon to the cannula is toward the center of the balloon, as is shown in FIG. 23, and not away from the center of the balloon, as is shown in FIGS. 15-22. The configuration of tapered end T9 shown in FIG. 23 (e.g., balloon tapered end orientation) may be chosen to limit the compression and/or extension forces that may be applied to the cannula between the balloon attachment points during balloon inflation.

Similarly, FIG. 23 shows apparatus 2310 including balloon 2349 having tapered ends T11 and T12 configured and/or attached to cannula 2340 or 2350, and inflated by volume of fluid V10. Apparatus 2310, parts, features, functions, dimensions, design, and/or manufacture thereof may be similar to those corresponding for apparatus 1500 or 1900, above, other than the orientation of tapered ends T11 and T12. Thus, cannula 2350 may be similar to cannula 1540 or 1940, and volume V10 may be similar to volume V1 or V6. Also, balloon 2349 may function similarly to balloon 1548 and/or 1948 as described above, other than the orientation of tapered ends T11 and T12. Specifically, ends T11 and T12 may be configured and/or attached to cannula 2350 such that the attachment point of the balloon to the cannula is toward the center of the balloon, as is shown in FIG. 23, and not away from the center of the balloon, as is shown in FIGS. 15-22. The configuration of tapered ends T11 and T12 shown in FIG. 23 (e.g., balloon tapered end orientation) may be chosen to limit the compression and/or extension forces that may be applied to the cannula between the balloon attachment points during balloon inflation.

In the foregoing specification, specific embodiments are described. For example, devices, structures, inflation-deflation devices, extension tubes, stopcocks, catheters, cannulas, balloons, occlusion devices, and processes described herein may be used to treat blood vessels of a human being, such as veins or arteries, including those of the human heart. However, various modifications and changes may be made thereto without departing from the broader spirit and scope of embodiments as set forth in the claims. The specification and drawings are, accordingly, to be regarded in an illustrative rather than a restrictive sense.

What is claimed is:

1. An apparatus comprising:
   a flexible tube having a length dimension for positioning between a syringe tube and an input adaptor of a catheter, the flexible tube consisting essentially of:
     a first end having a first connector adapted to attach and seal the flexible tube to an output of the syringe tube;
     a second end having a second connector to couple the flexible tube to the input adapter of the catheter;

an inner material defining a lumen having an inner diameter sufficient to communicate fluid between the syringe tube and the input adapter to cause a volume of fluid to inflate a balloon attached to the catheter to occlude a blood vessel at a region of interest;

an outer material surrounding and extruded over the inner material;

wherein the inner material has a modulus of elasticity greater than a modulus of elasticity of the outer material, and wherein the inner material thickness and the outer material thickness are chosen depending upon the modulus of the inner material and the modulus of the outer material to provide the flexible tube with a selected flexibility and low compliance, wherein the inner material and the outer material are miscible and are co-extruded, and wherein the inner diameter of the inner material is less than or equal to 0.035 inches, and the outer diameter of the outer material is greater than or equal to 0.13 inches.

2. The apparatus of claim 1, further comprising a stopcock having an input adapter attached and sealed to the second connector and an output adapter attached and sealed to the input adapter of the catheter, the stopcock having an inner diameter sufficient to communicate fluid between the syringe tube and the input adapter to cause a volume of fluid to inflate a balloon attached to the catheter to occlude a blood vessel at a region of interest.

3. The apparatus of claim 1, further comprising a third intermediate adhesive polymer attaching the inner material to the outer material.

4. The apparatus of claim 1, wherein the inner material is one of nylon and HDPE; wherein the outer material is one of a non-elastomeric polymer and LDPE;

wherein the outer material is miscible with inner material; and wherein the inner material has thickness less than a thickness of the outer material.

5. The apparatus of claim 1, wherein the inner material has a high modulus to provide low compliance and low volume change properties of the flexible tube; and the outer material has a low modulus to provide support to the inner material to provide kink resistance and to increase the flexible tube outer diameter to and outer diameter accepted by conventional extension tubing connectors, while maintaining an acceptable level of flexibility.

6. The apparatus of claim 1, wherein the inner material is bonded to the outer material by a bonding agent or due to their being miscible, to facilitate the attachment of the first connector to the first end and the second connector to the second end.

7. The apparatus of claim 1, wherein the flexible tube has a low compliance, such that it does not exhibit a substantial change in a volume of fluid within the inner diameter in response to (1) bends, curves, or movement of the tube, (2) grasping or holding the tube such as by a human hand, or (3) pressure changes of the fluid within the tube, when the flexible tube is used to inflate the balloon.

8. The apparatus of claim 1, comprising a syringe tube attached to the first connector, the syringe tube to provide a pressure of fluid to the input adapter to cause a volume of fluid to inflate a balloon attached to the catheter to occlude a blood vessel at a region of interest.

9. The apparatus of claim 1, wherein the second connector comprises a rotating male luer attached to the second end.

10. The apparatus of claim 1, further comprising a syringe tube attached to the first connector, and a catheter attached to the second connector, the syringe tube to provide a pressure of fluid to the input adapter to cause a volume of fluid to inflate a balloon attached to the catheter to occlude a blood vessel at a region of interest.

11. The apparatus of claim 1, wherein the inner material and the outer material are translucent materials.

12. A system comprising:

a syringe tube attached and sealed to a first connector on a first end of a flexible tube, the syringe tube to provide a pressure of fluid to the input adapter to cause a volume of fluid to inflate a balloon attached to the catheter to occlude a blood vessel at a region of interest;

a catheter attached and sealed to a second connector on a second end of the flexible tube, the catheter having an inner diameter sufficient to communicate fluid between the syringe tube and the input adapter to cause a volume of fluid to inflate a balloon attached to the catheter to occlude a blood vessel at a region of interest;

the flexible tube consisting essentially of:

an inner material defining a lumen having an inner diameter sufficient to communicate fluid between the syringe tube and the catheter to cause a volume of fluid to inflate a balloon attached to the catheter to occlude a blood vessel at a region of interest;

an outer material surrounding and extruded over the inner material;

wherein the inner material has a modulus of elasticity greater than a modulus of elasticity of the outer material, and wherein the inner material thickness and the outer material thickness are chosen depending upon the modulus of the inner material and the modulus of the outer material to provide the flexible tube with a selected flexibility and low compliance, wherein the inner material and the outer material are miscible and are co-extruded, and wherein the inner diameter of the inner material is less than or equal to 0.035 inches, and the outer diameter of the outer material is greater than or equal to 0.13 inches.

13. The apparatus of claim 12, further comprising a stopcock having an input adapter attached and sealed to the second connector and an output adapter attached and sealed to the catheter.

14. The apparatus of claim 13, wherein the stopcock is a two way stopcock and has another input adapter attached and sealed to an aspiration syringe.

15. The apparatus of claim 12, wherein the inner material and the outer material are translucent materials.

16. A system comprising:

a syringe tube coupled to a first connector on a first end of a flexible tube, the syringe tube to provide a pressure of fluid to the input adapter to cause a volume of fluid to inflate a balloon attached to the catheter to occlude a blood vessel at a region of interest;

a catheter coupled to a second end of the flexible tube, the catheter having an inner diameter sufficient to communicate fluid between the syringe tube and the input adapter to cause a volume of fluid to inflate a balloon attached to the catheter to occlude a blood vessel at a region of interest;

the flexible tube comprising:

an inner material defining a lumen having an inner diameter sufficient to communicate fluid between the syringe tube and the catheter to cause a volume of fluid to inflate a balloon attached to the catheter to occlude a blood vessel at a region of interest;

an outer material surrounding and co-extruded over the inner material;

wherein the inner material has a modulus of elasticity greater than a modulus of elasticity of the outer material, and wherein the inner material thickness and the outer material thickness are chosen depending upon the modulus of the inner material and the modulus of the outer material to provide the flexible tube with a selected flexibility and low compliance, wherein the inner material and the outer material are miscible and are co-extruded, and wherein the inner diameter of the inner material is less than or equal to 0.035 inches, and the outer diameter of the outer material is greater than or equal to 0.13 inches.

17. The apparatus of claim 16, further comprising a stopcock having an input adapter attached and sealed to the second connector and an output adapter attached and sealed to the catheter.

18. The apparatus of claim 17, wherein the stopcock is a two way stopcock and has another input adapter attached and sealed to an aspiration syringe.

19. The apparatus of claim 16, wherein the inner material and the outer material are translucent materials.

20. An apparatus comprising:
   a flexible tube having a length dimension for positioning between a syringe tube and an input adaptor of a catheter, the flexible tube comprising:
      a first end having a first connector adapted to attach and seal the flexible tube to an output of the syringe tube;
      a second end having a second connector to couple the flexible tube to the input adapter of the catheter;
      an inner material defining a lumen having an inner diameter sufficient to communicate fluid between the syringe tube and the input adapter to cause a volume of fluid to inflate a balloon attached to the catheter to occlude a blood vessel at a region of interest;
      an outer material surrounding and co-extruded over the inner material;
      wherein the inner material has a modulus of elasticity greater than a modulus of elasticity of the outer material, and wherein the inner material thickness and the outer material thickness are chosen depending upon the modulus of the inner material and the modulus of the outer material to provide the flexible tube with a selected flexibility and low compliance, wherein the inner material and the outer material are miscible and are co-extruded, and wherein the inner diameter of the inner material is less than or equal to 0.035 inches, and the outer diameter of the outer material is greater than or equal to 0.13 inches.

21. The apparatus of claim 20, further comprising a stopcock having an input adapter attached and sealed to the second connector and an output adapter attached and sealed to the input adapter of the catheter, the stopcock having an inner diameter sufficient to communicate fluid between the syringe tube and the input adapter to cause a volume of fluid to inflate a balloon attached to the catheter to occlude a blood vessel at a region of interest.

22. The apparatus of claim 20, wherein the inner material and the outer material are translucent materials.

* * * * *